(12) United States Patent
Julius et al.

(10) Patent No.: US 6,790,629 B2
(45) Date of Patent: Sep. 14, 2004

(54) NUCLEIC ACID SEQUENCES ENCODING CAPSAICIN RECEPTOR AND CAPSAICIN RECEPTOR-RELATED POLYPEPTIDES AND USES THEREOF

(75) Inventors: David J. Julius, San Francisco, CA (US); Michael J. Caterina, Mill Valley, CA (US); Anthony J. Brake, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 201 days.

(21) Appl. No.: 09/978,303

(22) Filed: Oct. 15, 2001

(65) Prior Publication Data

US 2003/0049728 A1 Mar. 13, 2003

Related U.S. Application Data

(63) Continuation of application No. 09/235,451, filed on Jan. 22, 1999, now Pat. No. 6,335,180, which is a continuation-in-part of application No. PCT/US98/17466, filed on Aug. 20, 1998, and a continuation-in-part of application No. 08/915,461, filed on Aug. 20, 1997, now abandoned.
(60) Provisional application No. 60/072,151, filed on Jan. 22, 1998.

(51) Int. Cl.[7] .................... G01N 33/53; G01N 33/567
(52) U.S. Cl. ...................................... 435/7.21; 435/7.1
(58) Field of Search ............................... 435/7.1, 7.21, 435/69.1; 436/501; 536/23.5

(56) References Cited

U.S. PATENT DOCUMENTS

| | | | |
|---|---|---|---|
| 5,074,977 A | 12/1991 | Cheung et al. | 204/153 |
| 5,232,684 A | 8/1993 | Blumberg et al. | |
| 5,234,566 A | 8/1993 | Osman et al. | 204/403 |
| 5,328,847 A | 7/1994 | Case et al. | 435/291 |
| 5,443,955 A | 8/1995 | Cornell et al. | 435/7.21 |
| 5,491,097 A | 2/1996 | Ribi et al. | 436/518 |
| 6,239,267 B1 | 5/2001 | Duckworth et al. | |
| 6,335,180 B1 | 1/2002 | Julius et al. | |

FOREIGN PATENT DOCUMENTS

| | | |
|---|---|---|
| EP | 0953638 | 3/1999 |
| EP | 0943 683 | 9/1999 |
| EP | 0953638 A1 | 11/1999 |
| EP | 1 160 254 | 5/2001 |
| WO | WO 99/37765 | 7/1999 |
| WO | WO 99/46377 | 9/1999 |
| WO | WO 00/29577 | 5/2000 |
| WO | WO 00/32766 | 6/2000 |
| WO | WO 00/63415 | 10/2000 |
| WO | WO 01/34805 | 5/2001 |
| WO | WO 01/68857 | 9/2001 |

OTHER PUBLICATIONS

Appendio and Szallasi, AEuphorbium: Modern Research on its Active Principle, Resiniferatoxin, Revives and Ancient Medicine,@ *Life Sciences*, 60(10): 681–696 (1997).
Bevan and Szolcsányl, ASensory Neuron–Specific Actions of Capsaicin: Mechanisms and applications,@ *Tips*, vol. 11 (Aug. 1990).
Bevan and Docherty, *Capsaicin in the Study of Pain*, Chapter 2: ACellular Mechanisms of the Action Capsaicin,@ pp. 27–44. Academic Press Ltd. (1993).
Fusco and Giacovazzo, APeppers and Pain,@ *Drugs*, 53(6): 909–914 (Jun. 1997).
Campbell, et al., *Capsaicin in the Study of Pain*, Chapter 12: AClinical Applications of Capsaicin and Its Analogues,@ pp. 255–273. Academic Press Ltd. (1993).
Caterina, et al., "The Capsaicin Receptor: A Heat–Activated Ion Channel in the Pain Pathway," *Nature* 389:816–824 (Oct. 23, 1997).
James, et al., Capsaicin in the Study of Pain, Chapter 5: AThe Capsaicin Receptor,@ pp. 83–104. Academic Press Ltd. (1993).
Koplas, et al, AThe Role of Calcium in the Desensitization of Capsaicin Responses in Rat Dorsal Root Ganglion Neurons,@ *Journal of Neuroscience*, 17(10): 3525–3537 (May 15, 1997).
Liu, et al., AThe Responses of Rat Trigeminal Ganglion Neurons to Capsaicin and Two Nonpungent Vanilloid Receptor Agonists, Olvanil and Glycerly Nonamide,@ *Journal of Neuroscience*, 17(11): 4101–4111 (Jun. 1, 1997).
Nagy, et al., "Cobalt Uptake Enables Identification of Capsaicin– and Bradykinin–Sensitive Supopulations of Rat Dorsal Root Ganglion Cells In Vitro," *Neuroscience* 56(1):241–246 (1993).

(List continued on next page.)

Primary Examiner—John D. Ulm
(74) Attorney, Agent, or Firm—Paula A. Borden; Carol L. Francis; Bozicevic, Field & Francis, LLP

(57) ABSTRACT

The present invention features vanilloid receptor polypeptides and vanilloid receptor-related polypeptides, specifically the capsaicin receptor subtypes VR1 and VR2 (VRRP-1), as well as the encoding polynucleotide sequences. In related aspects the invention features expression vectors and host cells comprising such polynucleotides. In other related aspects, the invention features transgenic animals having altered capsaicin receptor expression, due to, for example, the presence of an exogenous wild-type or modified capsaicin receptor-encoding polynucleotide sequence. The present invention also relates to antibodies that bind specifically to a capsaicin receptor polypeptide, and methods for producing these polypeptides. Further, the invention provides methods for using capsaicin receptor, including methods for screening candidate agents for activity as agonists or antagonists of capsaicin receptor activity, as well as assays to determine the amount of a capsaicin receptor-activating agent in a sample. In other related aspects, the invention provides methods for the use of the capsaicin receptor for the diagnosis and treatment of human disease and painful syndromes.

15 Claims, 12 Drawing Sheets

OTHER PUBLICATIONS

Rang, et al., Textbook of Pain, Chapter 3: ANociceptive Peripheral Neurons: Cellular Properties,@ pp. 57–78.

A. Maureen Rouhi, AChili Pepper Studies Paying off with Hot Birdseed and Better Analgesic,@ *Chemical and Engineering News*, pp. 30–31 (Mar. 4, 1996).

J. Szolesányi, *Capsaicin in the Study of Pain*, Chapter 1: AActions of Capsaicin on Sensory Receptors,@ pp. 1–26. Academic Press Ltd. (1993).

Towheed and Hochberg, AA Systematic Review of Randomized Controlled Trials of Pharma–cological Therapy in Osteoarthritis of the Knee, with an Emphasis on Trial Methodology,@ *Semin. Arthiritis Rheum.* 26(5): 755–770 (Apr. 1997).

Wood, et al., ACapsaicin–Induced Ion Fluxes Increase Cyclic GMP But Not Cyclic AMP Levels in Rat Sensory Neurons in Culture,@ *Journal of Neurochemistry*, 53(4): 1203–1211 (1989).

GenBank Accession No. H20025.
GenBank Accession No. AA236416.
GenBank Accession No. H51393.
GenBank Accession No. AA236417.
GenBank Accession No. H27879.
GenBank Accession No. H503364.
GenBank Accession No. N21167.
GenBank Accession No. AA461295.
GenBank Accession No. N26729.
GenBank Accession No. H21490.
GenBank Accession No. H49060.
GenBank Accession No. AA281349.
GenBank Accession No. W44731.
GenBank Accession No. N23395.
GenBank Accession No. W38665.
GenBank Accession No. AA357145.
GenBank Accession No. N24224.
GenBank Accession No. W92895.
GenBank Accession No. T12251.
GenBank Accession No. AA304033.
GenBank Accession No. N35179.
GenBank Accession No. AA281348.
GenBank Accession No. W82502.
GenBank Accession No. W53556.
GenBank Accession No. AA139413.
GenBank Accession No. AA76107.
GenBank Accession No. AA015295.
GenBank Accession No. AA274980.
GenBank Accession No. AA321554.

Szallasa, et al., "Characterization of a Peripheral Vanilloid (Capsaicin) Receptor in the Urinary Bladder of the Rat," *Life Sciences* 52(20):221–226 (1993).

Wardle, et al., "Pharmacological Characterization of the Vanilloid Receptor in the Rat Isolated Vas Deferens," *J. Pharm. Pharmacol.* 48:285–291 (1996).

Biro et al. (1997) "Recent Advances in Understanding of Vanilloid Receptors: A Therapeutic Target for Treatment of Pain and InFlammation in Skin," *Journal of Investigative Dermatology Symposium Proceedings*; vol. 2:56–60.

Szallasi (1994) "The Vanilloid (Capsaicin) Receptor: Receptor Types and Species Differences," *Gen. Pharmac.*, vol. 25(2):223–243.

```
M E Q R A S L D S E E S E S P P Q E N S C L D P P D R D P N C K P P P V K P H I F T T R S R    46
T R L F G K G D S E E A S P L D C P Y E E G G L A S C P I I T V S S V L T I Q R P G D G P A S    93
V R P S S Q D S V S A G E K P P R L Y D R R S I F D A V A Q S N C Q E L E S L L P F L Q R S K   140
K R L T D S E F K D P E T G K T C L L K A M L N L H N G Q N D T I A L L D V A R K T D S L K    187
Q F V N A S Y T D S Y Y K G Q T A L H I A I E R R N M T L V T L L V E N G A D V Q A A A N G D   234
F F K K T K G R P G F Y G E L P L S L A A C T N Q L A I V K F L L Q N S W Q P A D I S A R D    281
S V G N T V L H A L V E V A D N T V D N T K F V T S M Y N E I L I L G A K L H P T L K E E I T   329
N R K G L T P L A L A A S S G K I G V L A Y I L Q R E I H E P E C R H L S R K F T E W A Y G P   376
                TM1
V H S S L Y D L S C I D T C E K N S V L E V I A Y S S S E T P N R H D M L L V E P L N R L L Q   423
D K W D R F V K R I F Y F N F F Y Y C L Y M I I F T A A Y Y R P V E G L P P Y K L K N T V G     470
                  TM2
D Y F R V T G E I L S V S G G V Y F F F R G I Q Y F L Q R R P S L K S L F V D S Y S E I L F F V 518
     TM3                                                        TM4
Q S L F M L V S V V L Y F S Q R K E Y V A S M V F S L A M G W T N M L Y Y T R G F Q Q M G I    564
                              TM5
P H K C R G S A C K P G N S Y N S L Y S T C L E L F T I G M D L E F T E N Y D F K A V F         659
    TM6
I L L A Y V I L T Y I L L L N M L I A L M G E T V N K I A Q E S K N I W K L Q R A I T I L D T E 709
K S F L K C M R K A F R S G K L L Q V G F T P D G K D D Y R W C F R V D E V N W T T W N T      754
N V G I I N E D P G N C E G V K R T L S F S L R S G R V S G R N W K N F A L V P L L R D A S T  801
R D R H A T Q Q E E V Q L K H Y T G S L K P E D A E V F K D S M V P G E K     SEQ ID NO: 2    838
```

```
          636                                                        670
rat VR1         E L F K F T I G M G D L . . . . . E F T E N Y D F K A . V F I L L . A Y V I L T   (SEQ ID NO: 14)
human T12251    E L F K F T I G M G E L . . . . . A F Q E Q L H F R G . M V L L L . A Y V L L T   (SEQ ID NO: 15)
Caliphora z80230 S L F W A S F G L V D L V S F D L A G I K S F T R . M F G S Y S V I N             (SEQ ID NO: 16)
Drosophila TRP  S L F W A S F G L V D L V S F D L A G I K S T R . M F G S Y S V I N                (SEQ ID NO: 17)
Bovine x99792   S L F W S I F G L I N L Y Y T N V K A Q H E F T E . F V G A T M F G T Y N V I S   (SEQ ID NO: 18)
C. Elegans z72508 R T E I M T I G E F S V L Y R E W S A C D N F W N K W I G K L I F V I E T F V  (SEQ ID NO: 19)

671                                                        706
rat VR1         Y I L L L N M L I A L M G E T V N K I A Q E S K N I W K L Q R A I T I L           (SEQ ID NO: 14)
human T12251    Y I L L L N M L I A L M S E T V N S V A T D                                        (SEQ ID NO: 15)
Caliphora z80230 I I V L L N M L I A W S N S Y Q I I S E R A D Y E W K F A R S Q L W M           (SEQ ID NO: 16)
Drosophila TRP  I I V L L N M L I A W S N S Y Q I I S E R A D T E W K F A R S Q L W M             (SEQ ID NO: 17)
Bovine x99792   L V V L L N M L I A M M N N S Y Q L I A D H A D I E W K F A R T K L W M           (SEQ ID NO: 18)
C. Elegans z72508 S I L Q F N L L I A M M T R T Y E T I F L                                        (SEQ ID NO: 19)
```

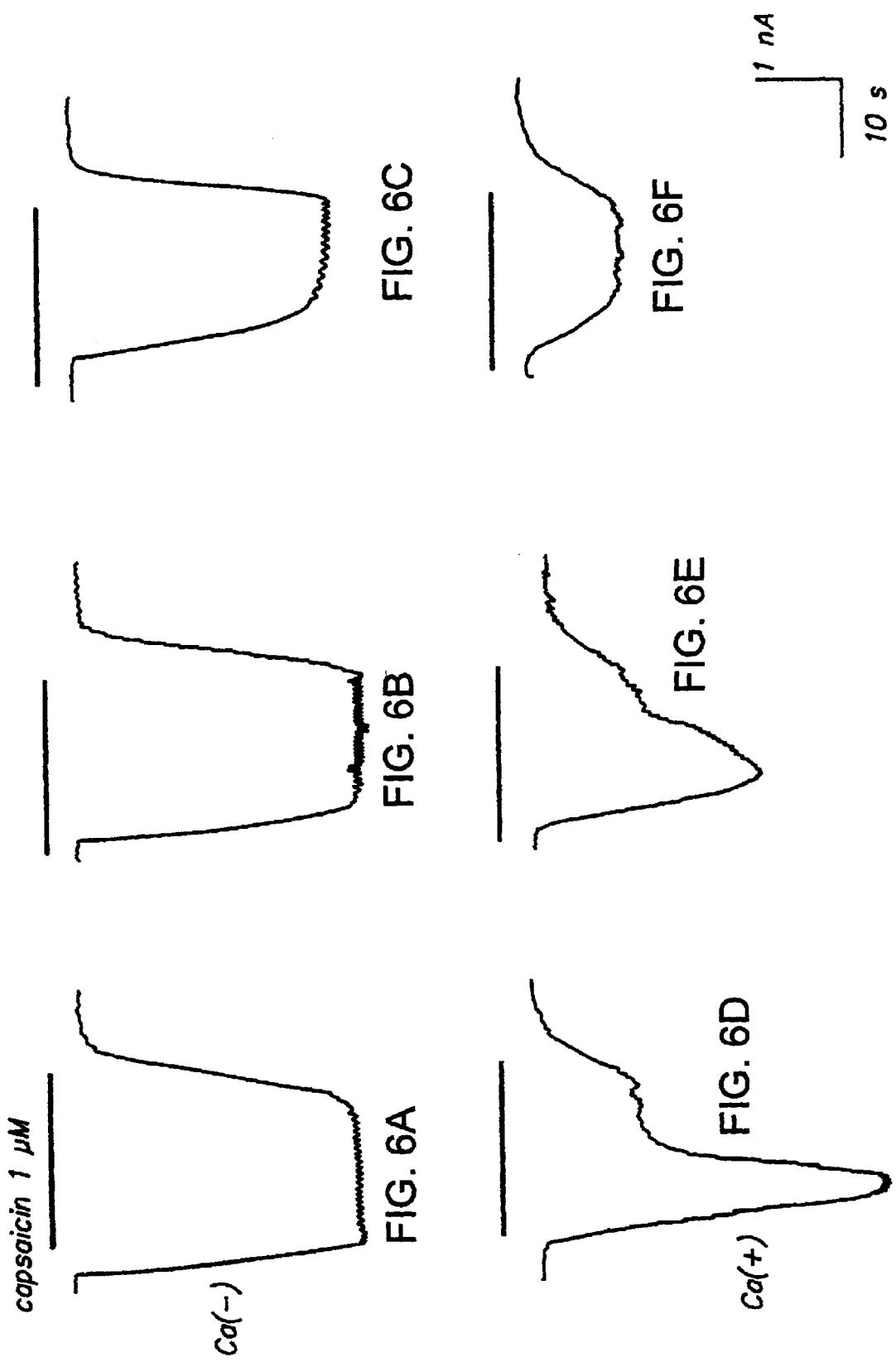

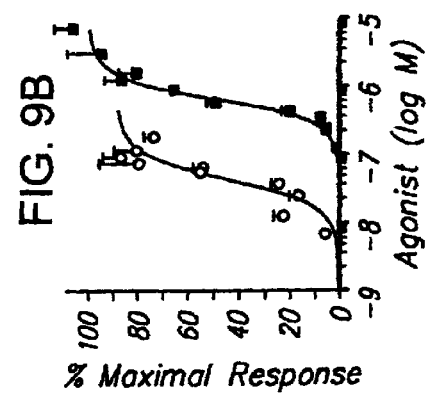
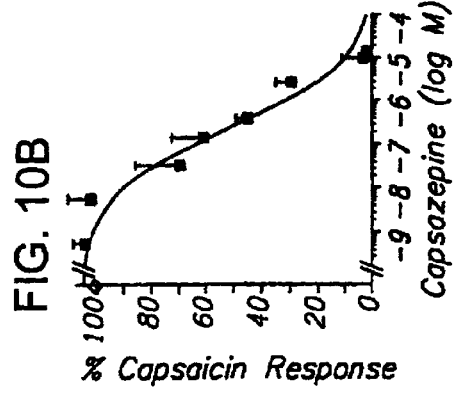
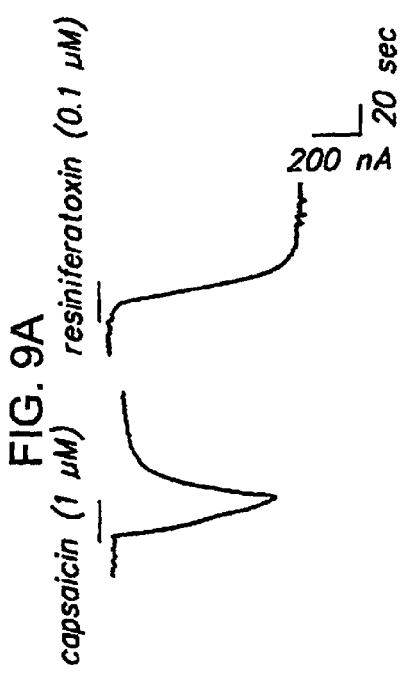
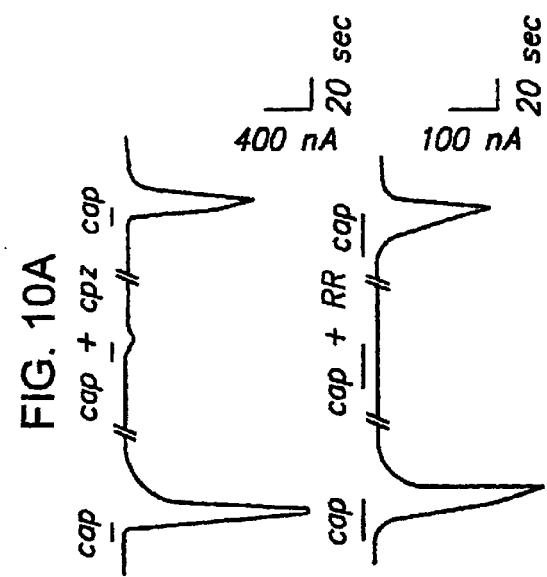

SEQUENCE LISTING

<160> NUMBER OF SEQ ID NOS: 48

<210> SEQ ID NO 1
<211> LENGTH: 2880
<212> TYPE: DNA
<213> ORGANISM: R. rattus

<400> SEQUENCE: 1

```
cagctccaag gcacttgctc catttggggt gtgcctgcac ctagctggtt gcaaattggg      60
ccacagagga tctggaaagg atggaacaac gggctagctt agactcagag gagtctgagt     120
ccccacccca agagaactcc tgcctggacc ctccagacag agaccctaac tgcaagccac     180
ctccagtcaa gccccacatc ttcactacca ggagtcgtac ccggcttttt gggaagggtg     240
actcggagga ggcctctccc ctggactgcc cttatgagga aggcgggctg gcttcctgcc     300
ctatcatcac tgtcagctct gttctaacta tccagaggcc tggggatgga cctgccagtg     360
tcaggccgtc atcccaggac tccgtctccg ctggtgagaa gcccccgagg ctctatgatc     420
gcaggagcat cttcgatgct gtggctcaga gtaactgcca ggagctggag agcctgctgc     480
ccttcctgca gaggagcaag aagcgcctga ctgacagcga gttcaaagac ccagagacag     540
gaaagacctg tctgctaaaa gccatgctca atctgcacaa tgggcagaat gacaccatcg     600
ctctgctcct ggacgttgcc cggaagacag acagcctgaa gcagtttgtc aatgccagct     660
acacagacag ctactacaag ggccagacag cactgcacat tgccattgaa cggcggaaca     720
tgacgctggt gaccctcttg gtggagaatg gagcagatgt ccaggctgcg gctaacgggg     780
acttcttcaa gaaaaccaaa gggaggcctg gcttctactt tggtgagctg cccctgtccc     840
tggctgcgtg caccaaccag ctggccattg tgaagttcct gctgcagaac tcctggcagc     900
ctgcagacat cagcgcccgg gactcagtgg gcaacacggt gcttcatgcc ctggtggagg     960
tggcagataa cacagttgac aacaccaagt tcgtgacaag catgtacaac gagatcttga    1020
tcctggggc caaactccac cccacgctga gctggaaga gatcaccaac aggaaggggc    1080
tcacgccact ggctctggct gctagcagtg ggaagatcgg ggtcttggcc tacattctcc    1140
agagggagat ccatgaaccc gagtgccgac acctatccag gaagttcacc gaatgggcct    1200
atgggccagt gcactcctcc ctttatgacc tgtcctgcat tgacacctgt gaaaagaact    1260
cggttctgga ggtgatcgct tacagcagca gtgagacccc taaccgtcat gacatgcttc    1320
tcgtggaacc cttgaaccga ctcctacagg acaagtggga cagatttgtc aagcgcatct    1380
tctacttcaa cttcttcgtc tactgcttgt atatgatcat cttcaccgcg gctgcctact    1440
atcggcctgt ggaaggcttg cccccctata agctgaaaaa caccgttggg gactatttcc    1500
gagtcaccgg agagatcttg tctgtgtcag gaggagtcta cttcttcttc cgagggattc    1560
aatatttcct gcagaggcga ccatccctca agagtttgtt tgtggacagc tacagtgaga    1620
tactttttctt tgtacagtcg ctgttcatgc tggtgtctgt ggtactgtac ttcagccaac    1680
gcaaggagta tgtggcttcc atggtgttct ccctggccat gggctggacc aacatgctct    1740
actatacccg aggattccag cagatgggca tctatgctgt catgattgag aagatgatcc    1800
```

-continued

```
tcagagacct gtgccggttt atgttcgtct acctcgtgtt cttgtttgga ttttccacag      1860
ctgtggtgac actgattgag gatgggaaga ataactctct gcctatggag tccacaccac      1920
acaagtgccg ggggtctgcc tgcaagccag gtaactctta caacagcctg tattccacat      1980
gtctggagct gttcaagttc accatcggca tgggcgacct ggagttcact gagaactacg      2040
acttcaaggc tgtcttcatc atcctgttac tggcctatgt gattctcacc tacatccttc      2100
tgctcaacat gctcattgct ctcatggtg agaccgtcaa caagattgca caagagagca      2160
agaacatctg gaagctgcag agagccatca ccatcctgga tacagagaag agcttcctga      2220
agtgcatgag gaaggccttc cgctctggca agctgctgca ggtggggttc actcctgacg      2280
gcaaggatga ctaccggtgg tgtttcaggg tggacgaggt aaactggact acctggaaca      2340
ccaatgtggg tatcatcaac gaggacccag gcaactgtga gggcgtcaag cgcaccctga      2400
gcttctccct gaggtcaggc cgagtttcag ggagaaactg gaagaacttt gccctggttc      2460
cccttctgag ggatgcaagc actcgagata gacatgccac ccagcaggaa gaagttcaac      2520
tgaagcatta tacgggatcc cttaagccag aggatgctga ggttttcaag gattccatgg      2580
tcccagggga gaaataatgg acactatgca gggatcaatg cggggtcttt gggtggtctg      2640
cttagggaac cagcagggtt gacgttatct gggtccactc tgtgcctgcc taggcacatt      2700
cctaggactt cggcgggcct gctgtgggaa ctgggaggtg tgtgggaatt gagatgtgta      2760
tccaaccatg atctccaaac atttggcttt caactcttta tggactttat taaacagagt      2820
gaatggcaaa tctctacttg gacacataaa aaaaaaaaa aaaaaaaaaa aaaaaaaaa       2880
```

<210> SEQ ID NO 2
<211> LENGTH: 838
<212> TYPE: PRT
<213> ORGANISM: R. rattus

<400> SEQUENCE: 2

```
Met Glu Gln Arg Ala Ser Leu Asp Ser Glu Ser Glu Ser Pro Pro
  1               5                   10                  15

Gln Glu Asn Ser Cys Leu Asp Pro Pro Asp Arg Asp Pro Asn Cys Lys
                 20                  25                  30

Pro Pro Val Lys Pro His Ile Phe Thr Thr Arg Ser Arg Thr Arg
             35                  40                  45

Leu Phe Gly Lys Gly Asp Ser Glu Glu Ala Ser Pro Leu Asp Cys Pro
         50                  55                  60

Tyr Glu Glu Gly Gly Leu Ala Ser Cys Pro Ile Ile Thr Val Ser Ser
 65                  70                  75                  80

Val Leu Thr Ile Gln Arg Pro Gly Asp Gly Pro Ala Ser Val Arg Pro
                 85                  90                  95

Ser Ser Gln Asp Ser Val Ser Ala Gly Glu Lys Pro Pro Arg Leu Tyr
                100                 105                 110

Asp Arg Arg Ser Ile Phe Asp Ala Val Ala Gln Ser Asn Cys Gln Glu
            115                 120                 125

Leu Glu Ser Leu Leu Pro Phe Leu Gln Arg Ser Lys Lys Arg Leu Thr
        130                 135                 140

Asp Ser Glu Phe Lys Asp Pro Glu Thr Gly Lys Thr Cys Leu Leu Lys
145                 150                 155                 160

Ala Met Leu Asn Leu His Asn Gly Gln Asn Asp Thr Ile Ala Leu Leu
                165                 170                 175

Leu Asp Val Ala Arg Lys Thr Asp Ser Leu Lys Gln Phe Val Asn Ala
            180                 185                 190
```

-continued

```
Ser Tyr Thr Asp Ser Tyr Tyr Lys Gly Gln Thr Ala Leu His Ile Ala
        195                 200                 205

Ile Glu Arg Arg Asn Met Thr Leu Val Thr Leu Leu Val Glu Asn Gly
    210                 215                 220

Ala Asp Val Gln Ala Ala Asn Gly Asp Phe Phe Lys Lys Thr Lys
225                 230                 235                 240

Gly Arg Pro Gly Phe Tyr Phe Gly Glu Leu Pro Leu Ser Leu Ala Ala
                245                 250                 255

Cys Thr Asn Gln Leu Ala Ile Val Lys Phe Leu Leu Gln Asn Ser Trp
            260                 265                 270

Gln Pro Ala Asp Ile Ser Ala Arg Asp Ser Val Gly Asn Thr Val Leu
        275                 280                 285

His Ala Leu Val Glu Val Ala Asp Asn Thr Val Asp Asn Thr Lys Phe
    290                 295                 300

Val Thr Ser Met Tyr Asn Glu Ile Leu Ile Leu Gly Ala Lys Leu His
305                 310                 315                 320

Pro Thr Leu Lys Leu Glu Glu Ile Thr Asn Arg Lys Gly Leu Thr Pro
                325                 330                 335

Leu Ala Leu Ala Ala Ser Ser Gly Lys Ile Gly Val Leu Ala Tyr Ile
            340                 345                 350

Leu Gln Arg Glu Ile His Glu Pro Glu Cys Arg His Leu Ser Arg Lys
        355                 360                 365

Phe Thr Glu Trp Ala Tyr Gly Pro Val His Ser Ser Leu Tyr Asp Leu
    370                 375                 380

Ser Cys Ile Asp Thr Cys Glu Lys Asn Ser Val Leu Glu Val Ile Ala
385                 390                 395                 400

Tyr Ser Ser Ser Glu Thr Pro Asn Arg His Asp Met Leu Leu Val Glu
                405                 410                 415

Pro Leu Asn Arg Leu Leu Gln Asp Lys Trp Asp Arg Phe Val Lys Arg
            420                 425                 430

Ile Phe Tyr Phe Asn Phe Phe Val Tyr Cys Leu Tyr Met Ile Ile Phe
        435                 440                 445

Thr Ala Ala Ala Tyr Tyr Arg Pro Val Glu Gly Leu Pro Pro Tyr Lys
    450                 455                 460

Leu Lys Asn Thr Val Gly Asp Tyr Phe Arg Val Thr Gly Glu Ile Leu
465                 470                 475                 480

Ser Val Ser Gly Gly Val Tyr Phe Phe Arg Gly Ile Gln Tyr Phe
                485                 490                 495

Leu Gln Arg Arg Pro Ser Leu Lys Ser Leu Phe Val Asp Ser Tyr Ser
            500                 505                 510

Glu Ile Leu Phe Phe Val Gln Ser Leu Phe Met Leu Val Ser Val Val
        515                 520                 525

Leu Tyr Phe Ser Gln Arg Lys Glu Tyr Val Ala Ser Met Val Phe Ser
    530                 535                 540

Leu Ala Met Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Leu Val Phe Leu Phe Gly Phe Ser
            580                 585                 590

Thr Ala Val Val Thr Leu Ile Glu Asp Gly Lys Asn Asn Ser Leu Pro
        595                 600                 605
```

```
Met Glu Ser Thr Pro His Lys Cys Arg Gly Ser Ala Cys Lys Pro Gly
    610                 615                 620

Asn Ser Tyr Asn Ser Leu Tyr Ser Thr Cys Leu Glu Leu Phe Lys Phe
625                 630                 635                 640

Thr Ile Gly Met Gly Asp Leu Glu Phe Thr Glu Asn Tyr Asp Phe Lys
            645                 650                 655

Ala Val Phe Ile Ile Leu Leu Ala Tyr Val Ile Leu Thr Tyr Ile
        660                 665                 670

Leu Leu Leu Asn Met Leu Ile Ala Leu Met Gly Glu Thr Val Asn Lys
            675                 680                 685

Ile Ala Gln Glu Ser Lys Asn Ile Trp Lys Leu Gln Arg Ala Ile Thr
    690                 695                 700

Ile Leu Asp Thr Glu Lys Ser Phe Leu Lys Cys Met Arg Lys Ala Phe
705                 710                 715                 720

Arg Ser Gly Lys Leu Leu Gln Val Gly Phe Thr Pro Asp Gly Lys Asp
                725                 730                 735

Asp Tyr Arg Trp Cys Phe Arg Val Asp Glu Val Asn Trp Thr Thr Trp
            740                 745                 750

Asn Thr Asn Val Gly Ile Ile Asn Glu Asp Pro Gly Asn Cys Glu Gly
        755                 760                 765

Val Lys Arg Thr Leu Ser Phe Ser Leu Arg Ser Gly Arg Val Ser Gly
    770                 775                 780

Arg Asn Trp Lys Asn Phe Ala Leu Val Pro Leu Leu Arg Asp Ala Ser
785                 790                 795                 800

Thr Arg Asp Arg His Ala Thr Gln Gln Glu Val Gln Leu Lys His
                805                 810                 815

Tyr Thr Gly Ser Leu Lys Pro Glu Asp Ala Glu Val Phe Lys Asp Ser
            820                 825                 830

Met Val Pro Gly Glu Lys
        835

<210> SEQ ID NO 3
<211> LENGTH: 2736
<212> TYPE: DNA
<213> ORGANISM: R. rattus

<400> SEQUENCE: 3
ggcgttaaac ctgctctgtc cactgtgtga gacgaacagg tggagggtgg acgacgcaga    60
gaaagctcgg agcgggccgc ggaggttccc acagccccat tactgtcagc gttgagccgc   120 accctccgg gccgcacttc ctctctcagt ccccgctgcc ggagagcccc gctaggctcg   180
gtgatcctag cctgcagttt gccgccgcta caccttggct tcagcctgcg ggtcccagc   240 caggcctgcc cctgcggtat gagagaggaa ccttaacatc tccatctcta cagaggtttc   300
agctgtaagg agcatcctcc tctctcagga tgacttcagc ctccagcccc ccagctttca   360
ggctggagac ttccgatgga gatgaagagg gcaatgctga ggtgaacaag gggaagcagg   420
aaccgccccc catggagtca ccattccaga gggaggaccg gaattcctcc cctcagatca   480 agtgaacct caacttcata agagacctc ctaaaaacac ttctgctccc agccagcagg   540
agccagatcg gtttgaccgt gaccgactct tcagtgtggt ctcccggggt gtccccgagg   600
aactgactgg actgctagaa tacctgcgct ggaacagcaa gtacctcact gactctgcat   660
acacagaagg ctccactgga aagacgtgcc tgatgaaggc tgtgctgaac cttcaggatg   720
gggtcaatgc ctgcatcatg ccgctgctgc agattgacaa ggattccggc aatcccaagc   780
```

-continued

```
ccctcgtcaa tgcccagtgc accgatgagt tctaccaagg ccacagtgcg ctgcacatcg      840
ccatagagaa gaggagcctg cagtgcgtga agctgctggt agagaatgga gcggatgttc      900
acctccgagc ctgtggccgc ttcttccaaa agcaccaagg aacttgtttc tattttggag      960
agctacctct ttctctggct gcgtgcacca agcagtggga tgtggtgacc tacctcctgg     1020
agaacccaca ccagccggcc agcctggagg ccaccgactc cctgggcaac acagtcctgc     1080
atgctctggt aatgattgca gataactcgc ctgagaacag tgccctggtg atccacatgt     1140
acgacgggct tctacaaatg ggggcgcgcc tctgccccac tgtgcagctt gaggaaatct     1200
ccaaccacca aggcctcaca ccctgaaac tagccgccaa ggaaggcaaa atcgagattt     1260
tcaggcacat tctgcagcgg gaattctcag accgtacca gccccttttcc cgaaagttta     1320 ctgagtggtg ttacggtcct gtgcgggtat cgctgtacga cctgtcctct gtggacagct     1380
gggaaaagaa ctcggtgctg agatcatcg cttttcattg caagagcccg aaccggcacc     1440
gcatggtggt tttagaacca ctgaacaagc ttctgcagga gaatgggat cggctcgtct     1500 caagattctt cttcaacttc gcctgctact tggtctacat gttcatcttc accgtcgttg     1560
cctaccacca gccttccctg gatcagccag ccatcccctc atcaaaagcg acttttgggg     1620
aatccatgct gctgctgggc acattctga tcctgcttgg gggtatttac ctcttactgg     1680
gccagctgtg gtactttgg cggcggcgcc tgtttatctg gatctcattc atggacagct     1740
actttgaaat cctctttctc cttcaggctc tgctcacagt gctgtcccag gtgctgcgct     1800
tcatggagac tgaatggtac ctaccccctgc tagtgttatc cctagtgctg gctggctgaa     1860 acctgctta ctacacacgg ggctttcagc acacaggcat ctacagtgtc atgatccaga     1920
aggtcatcct tcgagacctg ctccgtttcc tgctggtcta cctggtcttc cttttcggct     1980
ttgctgtagc cctagtaagc ttgagcagag aggcccgaag tcccaaagcc cctgaagata     2040
acaactccac agtgacggaa cagcccacg tgggccagga ggaggagcca gctccatatc     2100
ggagcattct ggatgcctcc ctagagctgt tcaagttcac cattggtatg ggggagctgg     2160 cttttccagga acagctgcgt tttcgtgggg tggtcctgct gttgctgttg gcctacgtcc     2220
ttctcaccta cgtcctgctg ctcaacatgc tcattgctct catgagcgaa actgtcaacc     2280
acgttgctga caacagctgg agcatctgga agttgcagaa agccatctct gtcttggaga     2340
tggagaatgg ttactggtgg tgccggagga agaaacatcg tgaagggagg ctgctgaaag     2400
tcggcaccag ggggggatggt acccctgatg agcgctggtg cttcagggtg gaggaagtaa     2460
attgggctgc ttgggagaag actcttccca ccttatctga ggatccatca gggccaggca     2520
tcactggtaa taaaaagaac ccaacctcta aaccggggaa gaacagtgcc tcagaggaag     2580
accatctgcc ccttcaggtc ctccagtccc cctgatggcc cagatgcagc agcaggctgg     2640
caggatggag tagggaatct tcccagccac accagaggct actgaatttt ggtggaaata     2700 taaatattttt ttttgcataa aaaaaaaaaa aaaaaa     2736
```

<210> SEQ ID NO 4
<211> LENGTH: 761
<212> TYPE: PRT
<213> ORGANISM: R. rattus

<400> SEQUENCE: 4

```
Met Thr Ser Ala Ser Ser Pro Pro Ala Phe Arg Leu Glu Thr Ser Asp
 1               5                  10                  15

Gly Asp Glu Glu Gly Asn Ala Glu Val Asn Lys Gly Lys Gln Glu Pro
            20                  25                  30
```

-continued

```
Pro Pro Met Glu Ser Pro Phe Gln Arg Glu Asp Arg Asn Ser Ser Pro
        35                  40                  45
Gln Ile Lys Val Asn Leu Asn Phe Ile Lys Arg Pro Pro Lys Asn Thr
    50                  55                  60
Ser Ala Pro Ser Gln Gln Glu Pro Asp Arg Phe Asp Arg Asp Arg Leu
65                  70                  75                  80
Phe Ser Val Val Ser Arg Gly Val Pro Glu Glu Leu Thr Gly Leu Leu
                85                  90                  95
Glu Tyr Leu Arg Trp Asn Ser Lys Tyr Leu Thr Asp Ser Ala Tyr Thr
            100                 105                 110
Glu Gly Ser Thr Gly Lys Thr Cys Leu Met Lys Ala Val Leu Asn Leu
        115                 120                 125
Gln Asp Gly Val Asn Ala Cys Ile Met Pro Leu Leu Gln Ile Asp Lys
    130                 135                 140
Asp Ser Gly Asn Pro Lys Pro Leu Val Asn Ala Gln Cys Thr Asp Glu
145                 150                 155                 160
Phe Tyr Gln Gly His Ser Ala Leu His Ile Ala Ile Glu Lys Arg Ser
                165                 170                 175
Leu Gln Cys Val Lys Leu Leu Val Glu Asn Gly Ala Asp Val His Leu
            180                 185                 190
Arg Ala Cys Gly Arg Phe Phe Gln Lys His Gln Gly Thr Cys Phe Tyr
        195                 200                 205
Phe Gly Glu Leu Pro Leu Ser Leu Ala Ala Cys Thr Lys Gln Trp Asp
    210                 215                 220
Val Val Thr Tyr Leu Leu Glu Asn Pro His Gln Pro Ala Ser Leu Glu
225                 230                 235                 240
Ala Thr Asp Ser Leu Gly Asn Thr Val Leu His Ala Leu Val Met Ile
                245                 250                 255
Ala Asp Asn Ser Pro Glu Asn Ser Ala Leu Val Ile His Met Tyr Asp
            260                 265                 270
Gly Leu Leu Gln Met Gly Ala Arg Leu Cys Pro Thr Val Gln Leu Glu
        275                 280                 285
Glu Ile Ser Asn His Gln Gly Leu Thr Pro Leu Lys Leu Ala Ala Lys
    290                 295                 300
Glu Gly Lys Ile Glu Ile Phe Arg His Ile Leu Gln Arg Glu Phe Ser
305                 310                 315                 320
Gly Pro Tyr Gln Pro Leu Ser Arg Lys Phe Thr Glu Trp Cys Tyr Gly
                325                 330                 335
Pro Val Arg Val Ser Leu Tyr Asp Leu Ser Ser Val Asp Ser Trp Glu
            340                 345                 350
Lys Asn Ser Val Leu Glu Ile Ile Ala Phe His Cys Lys Ser Pro Asn
        355                 360                 365
Arg His Arg Met Val Val Leu Glu Pro Leu Asn Lys Leu Leu Gln Glu
    370                 375                 380
Lys Trp Asp Arg Leu Val Ser Arg Phe Phe Asn Phe Ala Cys Tyr
385                 390                 395                 400
Leu Val Tyr Met Phe Ile Phe Thr Val Val Ala Tyr His Gln Pro Ser
                405                 410                 415
Leu Asp Gln Pro Ala Ile Pro Ser Ser Lys Ala Thr Phe Gly Glu Ser
            420                 425                 430
Met Leu Leu Leu Gly His Ile Leu Ile Leu Leu Gly Gly Ile Tyr Leu
        435                 440                 445
```

```
Leu Leu Gly Gln Leu Trp Tyr Phe Trp Arg Arg Arg Leu Phe Ile Trp
    450                 455                 460

Ile Ser Phe Met Asp Ser Tyr Phe Glu Ile Leu Phe Leu Leu Gln Ala
465                 470                 475                 480

Leu Leu Thr Val Leu Ser Gln Val Leu Arg Phe Met Glu Thr Glu Trp
                485                 490                 495

Tyr Leu Pro Leu Leu Val Leu Ser Leu Val Gly Trp Leu Asn Leu
            500                 505                 510

Leu Tyr Tyr Thr Arg Gly Phe Gln His Thr Gly Ile Tyr Ser Val Met
        515                 520                 525

Ile Gln Lys Val Ile Leu Arg Asp Leu Leu Arg Phe Leu Leu Val Tyr
    530                 535                 540

Leu Val Phe Leu Phe Gly Phe Ala Val Ala Leu Val Ser Leu Ser Arg
545                 550                 555                 560

Glu Ala Arg Ser Pro Lys Ala Pro Glu Asp Asn Asn Ser Thr Val Thr
                565                 570                 575

Glu Gln Pro Thr Val Gly Gln Glu Glu Pro Ala Pro Tyr Arg Ser
            580                 585                 590

Ile Leu Asp Ala Ser Leu Glu Leu Phe Lys Phe Thr Ile Gly Met Gly
    595                 600                 605

Glu Leu Ala Phe Gln Glu Gln Leu Arg Phe Arg Gly Val Val Leu Leu
    610                 615                 620

Leu Leu Leu Ala Tyr Val Leu Leu Thr Tyr Val Leu Leu Asn Met
625                 630                 635                 640

Leu Ile Ala Leu Met Ser Glu Thr Val Asn His Val Ala Asp Asn Ser
                645                 650                 655

Trp Ser Ile Trp Lys Leu Gln Lys Ala Ile Ser Val Leu Glu Met Glu
                660                 665                 670

Asn Gly Tyr Trp Trp Cys Arg Arg Lys Lys His Arg Glu Gly Arg Leu
            675                 680                 685

Leu Lys Val Gly Thr Arg Gly Asp Gly Thr Pro Asp Glu Arg Trp Cys
    690                 695                 700

Phe Arg Val Glu Glu Val Asn Trp Ala Ala Trp Glu Lys Thr Leu Pro
705                 710                 715                 720

Thr Leu Ser Glu Asp Pro Ser Gly Pro Gly Ile Thr Gly Asn Lys Lys
                725                 730                 735

Asn Pro Thr Ser Lys Pro Gly Lys Asn Ser Ala Ser Glu Glu Asp His
            740                 745                 750

Leu Pro Leu Gln Val Leu Gln Ser Pro
        755                 760

<210> SEQ ID NO 5
<211> LENGTH: 273
<212> TYPE: DNA
<213> ORGANISM: Homo sapiens
<220> FEATURE:
<221> NAME/KEY: misc_feature
<222> LOCATION: (1)...(273)
<223> OTHER INFORMATION: n = A,T,C or G

<400> SEQUENCE: 5
tgcggtctcc cngggtgtc cccgaggatc tggctggact tccnagagta cctgagcaag      60
accagcaagt acctcaccga ctcggaatac acagagggct ncnacaggta agacgtgcct    120
gatgaaggct gtgctgaacc ttaaggacgg ggtcaatgcc tgcattctgc cactgctgca    180
gatcgachgg gactctggca atcctcagcc cctggtaaat gcccagtgca cagatgacta    240
```
ttaccgaggc cacagcnctc tgcacatcgc cat 273

<210> SEQ ID NO 6
<211> LENGTH: 768
<212> TYPE: DNA
<213> ORGANISM: Homo sapiens
<220> FEATURE:
<221> NAME/KEY: misc_feature
<222> LOCATION: (1)...(768)
<223> OTHER INFORMATION: n = A,T,C or G

<400> SEQUENCE: 6
tcggtgagct accoctctct ttggccgctt gcaccaagca gtgggatgtg gtaagctacc      60
tcctggagaa cccacaccag cccgccagcc tgcagnncac tgactcccag ggcaacacag     120
tcctgcatgc cctagtgatg atctcggaca actcagctga aacattgca ctggtgacca     180 gcatgtatga tgggctcctc caagctgggg cccgncctct gccctaccgt gcnagcttga    240
ggacatccgc aacctgcagg atctcacgcc tctgnaannt ggccgccaag gagggcaaga    300
tcgrrwttty maggcacatc ctnnsmagcg ggrrktttca ggactgnagc caccttttnnc   360 ccgaaagttc accgagtggt ngctannkgg gcctgtccgg gntgtcgctg tnatgacctg    420
gnnyttctnt ggacagctgt naggagaact cagtgctgga gatcattgcc tttcattngc    480
aaragcccgn accgacaccg aatggtcgtt ttggagcccc tgaacaaact gctgcaggcn    540
gaaatgggat ctgctcatcc ccaagttctt cttaaacttc ctgtgtaatc tgatntacat    600
gttcatcttc amckctgttg cctaccatca gcctacccng aagaagcagg ccgcccctca    660
cctgaaagcg gaggttggaa actccatgct gctgacgggc acatcctta tcctgctagg    720 ggggatctac ctcctcgtgg ggcaaaagtg gaaattttgg gggggaat                 768

<210> SEQ ID NO 7
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 7
tgtttcctgg ccatcgagtg gtacctgccc ctgcttgtgt ctgcgctggt gctgggctgg     60
ctgaacctgc tttactatac acgtggcttc cagcacacag gcatctacag tgtcatgatc    120
cagaagccct ggtgagcctg agccaggatt ggcgccccga agctcctaca ggccccaatg    180
ccacagagtc agtgcagccc atggagggac aggaggacga gggcaacggg gcccagtaca    240
ggggtatcct ggwagcctcc ttggagctct tcaaattcac catcggcatg ggcgagctgg    300
ccttccaggn gcagctgcac ttccgcggca tnggtgctgc tgctgctnct ggcctacgtn    360
ctgctcacct acatcctgct gctcaacatg ctcatcgccc tcatngagcg agaccgtcaa    420
cankktcgcc actgacagct ggagcatctg gaagctgcag aaagncatct nntgtcctgg    480
agatggagaa tggctattgg tggtgcanga agaagcagcg ggcaggtgtg atgctgancg    540
ttggcactaa gccagatggc agcccsgatg agcgctggtg cttcagggtn gaggaggtga    600
actgggcttc atngggagca gacgctgcct acgctgtgtg aggacccgtc                650

<210> SEQ ID NO 8
<211> LENGTH: 317
<212> TYPE: DNA

<213> ORGANISM: Homo sapiens

<400> SEQUENCE: 8

```
gagcttctcc ctgcggtcaa gcagagtttc aggcagacac tggaagaact ttgccctggt    60
cccccttttta agagaggcaa gtctcgaata ggcagtctgc tcagcccgag gaagtttatc   120
tgcgacagtt ttcagggtct ctaaagccag aggacgctga ggtcttcaag agtcctgccg   180
cttccgggga gaagtgagga cgtcacgcag acagcactgt caacactggg ccttaggaga   240
ccccgttgcc acgggggggct ctgagggaac acagtgcttt ttcagcagcc ttgctggtct   300
ttgctgccca gcatgtt                                                  317
```

<210> SEQ ID NO 9
<211> LENGTH: 65
<212> TYPE: PRT
<213> ORGANISM: Homo sapiens
<220> FEATURE:
<221> NAME/KEY: VARIANT
<222> LOCATION: (1)...(65)
<223> OTHER INFORMATION: Xaa = Any Amino Acid

<400> SEQUENCE: 9

```
Ser Phe Ser Leu Arg Ser Ser Arg Val Ser Gly Arg His Trp Lys Asn
 1               5                  10                  15
Phe Ala Leu Val Pro Leu Leu Arg Glu Ala Ser Xaa Arg Xaa Arg Gln
            20                  25                  30
Ser Ala Gln Pro Glu Glu Val Tyr Leu Arg Gln Phe Ser Gly Ser Leu
        35                  40                  45
Lys Pro Glu Asp Ala Glu Val Phe Lys Ser Pro Ala Ala Ser Gly Glu
    50                  55                  60
Lys
65
```

<210> SEQ ID NO 10
<211> LENGTH: 471
<212> TYPE: DNA
<213> ORGANISM: M. musculus
<220> FEATURE:
<221> NAME/KEY: misc_feature
<222> LOCATION: (1)...(471)
<223> OTHER INFORMATION: n = A,T,C or G

<400> SEQUENCE: 10

```
cctgcagaag agcancangc gcctgannga cagcgagttc aaagacccag agacgggaaa    60
gacctgtctg ctcaaagcca tgctcaatct gcacaatggg cagaacgaca ccattgctct   120
gctcctggac attgcccgga agacagatag cctgaagcga tttgtcaatg ccagctacac   180
agacagctac tacaagggcc agacagcatt acacattgcc attgaaaggc ggaacatggc   240
nctggtgacc ctcttggtgg agaatggagc agatgtccag gctgctgctg acggggactt   300
cttcnanaaa accaanggga ggcctggctt ctactttggt gagctgcccc tgtccctggc   360
tgcgtgcacc aaccagctgg ccattgtgaa attcctgctg cagaactcct gggcagcctg   420
cagacatcag tggcncggga ttcngtgggc aacacngtgc tgcacnccct t            471
```

<210> SEQ ID NO 11
<211> LENGTH: 450
<212> TYPE: DNA
<213> ORGANISM: M. musculus

<400> SEQUENCE: 11

```
caagtgtcgg ggatctgcct tgcagggcca agttaattct ttacaacagc ctgtattcca      60
catgtctgga gctgttcaag ttcaccatcg gcatgggtga cctggagttc accgagaact     120
atgacttcaa ggctgtcttt catcatcctg ttactggcct atgtgattct cacctacatc     180
ctcctgctca acatgctcat tgctctcatg ggcgagactg tcaacaagat tgcacaagag     240
agcaagaaca tctggaagct gcagcgagcc atcaccatcc tggatacaga gaagagtttc     300
ctgaagtgca tgaggaaggc cttccgctcc ggcaagctgc tgcaggtggg gttcacgccg     360
gacggcaagg atgacttccg gtggtgcttc agggtggatg aggtgaactg gactacctgg     420
aacaccaacg tgggcatcat caacgaggac                                     450
```

```
<210> SEQ ID NO 12
<211> LENGTH: 18
<212> TYPE: DNA
<213> ORGANISM: R. rattus

<400> SEQUENCE: 12
gaccagcaag tacctcac                                                   18

<210> SEQ ID NO 13
<211> LENGTH: 49
<212> TYPE: DNA
<213> ORGANISM: R. rattus

<400> SEQUENCE: 13
ctcccatgca gcccagttta cttcctccac cctgaagcac cagcgctca                 49

<210> SEQ ID NO 14
<211> LENGTH: 71
<212> TYPE: PRT
<213> ORGANISM: R. rattus

<400> SEQUENCE: 14

Glu Leu Phe Lys Phe Thr Ile Gly Met Gly Asp Leu Glu Phe Thr Glu
  1               5                  10                  15

Asn Tyr Asp Phe Lys Ala Val Phe Ile Ile Leu Leu Ala Tyr Val
             20                  25                  30

Ile Leu Thr Tyr Ile Leu Leu Leu Asn Met Leu Ile Ala Leu Met Gly
         35                  40                  45

Glu Thr Val Asn Lys Ile Ala Gln Glu Ser Lys Asn Ile Trp Lys Leu
     50                  55                  60

Gln Arg Ala Ile Thr Ile Leu
 65                  70

<210> SEQ ID NO 15
<211> LENGTH: 57
<212> TYPE: PRT
<213> ORGANISM: Homo sapiens

<400> SEQUENCE: 15

Glu Leu Phe Lys Phe Thr Ile Gly Met Gly Glu Leu Ala Phe Gln Glu
  1               5                  10                  15

Gln Leu His Phe Arg Gly Met Val Leu Leu Leu Leu Ala Tyr Val
             20                  25                  30

Leu Leu Thr Tyr Ile Leu Leu Leu Asn Met Leu Ile Ala Leu Met Ser
         35                  40                  45

Glu Thr Val Asn Ser Val Ala Thr Asp
     50                  55
```

```
<210> SEQ ID NO 16
<211> LENGTH: 75
<212> TYPE: PRT
<213> ORGANISM: Caliphora

<400> SEQUENCE: 16

Ser Leu Phe Trp Ala Ser Phe Gly Leu Val Asp Leu Val Ser Phe Asp
 1               5                  10                  15

Leu Ala Gly Ile Lys Ser Phe Thr Arg Phe Trp Ala Leu Leu Met Phe
            20                  25                  30

Gly Ser Tyr Ser Val Ile Asn Ile Ile Val Leu Leu Asn Met Leu Ile
        35                  40                  45

Ala Met Met Ser Asn Ser Tyr Gln Ile Ile Ser Glu Arg Ala Asp Val
    50                  55                  60

Glu Trp Lys Phe Ala Arg Ser Gln Leu Trp Met
65                  70                  75

<210> SEQ ID NO 17
<211> LENGTH: 75
<212> TYPE: PRT
<213> ORGANISM: D. melanogaster

<400> SEQUENCE: 17

Ser Leu Phe Trp Ala Ser Phe Gly Leu Val Asp Leu Val Ser Phe Asp
 1               5                  10                  15

Leu Ala Gly Ile Lys Ser Phe Thr Arg Phe Trp Ala Leu Leu Met Phe
            20                  25                  30

Gly Ser Tyr Ser Val Ile Asn Ile Ile Val Leu Leu Asn Met Leu Ile
        35                  40                  45

Ala Met Met Ser Asn Ser Tyr Gln Ile Ile Ser Glu Arg Ala Asp Val
    50                  55                  60

Glu Trp Lys Phe Ala Arg Ser Gln Leu Trp Met
65                  70                  75

<210> SEQ ID NO 18
<211> LENGTH: 75
<212> TYPE: PRT
<213> ORGANISM: B. taurus

<400> SEQUENCE: 18

Ser Leu Phe Trp Ser Ile Phe Gly Leu Ile Asn Leu Tyr Val Thr Asn
 1               5                  10                  15

Val Lys Ala Gln His Glu Phe Thr Glu Phe Val Gly Ala Thr Met Phe
            20                  25                  30

Gly Thr Tyr Asn Val Ile Ser Leu Val Val Leu Leu Asn Met Leu Ile
        35                  40                  45

Ala Met Met Asn Asn Ser Tyr Gln Leu Ile Ala Asp His Ala Asp Ile
    50                  55                  60

Glu Trp Lys Phe Ala Arg Thr Lys Leu Trp Met
65                  70                  75

<210> SEQ ID NO 19
<211> LENGTH: 61
<212> TYPE: PRT
<213> ORGANISM: C. elegans

<400> SEQUENCE: 19

Arg Thr Phe Ile Met Thr Ile Gly Glu Phe Ser Val Leu Tyr Arg Glu
 1               5                  10                  15
```

Met Ser Ala Cys Asp Asn Phe Trp Met Lys Trp Ile Gly Lys Leu Ile
            20                  25                  30

Phe Val Ile Phe Glu Thr Phe Val Ser Ile Leu Gln Phe Asn Leu Leu
            35                  40                  45

Ile Ala Met Met Thr Arg Thr Tyr Glu Thr Ile Phe Leu
            50                  55                  60

<210> SEQ ID NO 20
<211> LENGTH: 350
<212> TYPE: DNA
<213> ORGANISM: Homo sapiens
<220> FEATURE:
<221> NAME/KEY: misc_feature
<222> LOCATION: (1)...(350)
<223> OTHER INFORMATION: n = A,T,C or G

<400> SEQUENCE: 20
gagaggtcct ggctggacnn ngcagcctcc tcctcctagg atgacctcac cctccagctc      60
tccagttttc aggttggaga cattagatgg aggccaagaa gatggctctg aggcggacag     120
aggaaagctg gattttggga gcgggctgcc tcccatggga tcacagttcc agggcgagga     180
ccggaaattc gccccctcaga taagagtcaa cctcaactac cgaaagggaa caggtgccag     240
tcagccggat ccaaaccgat tgaccgaga tcggctcttc aatgcggtct cccggggtgt     300
ccccgaggat ctggctggac ttccagagta cctgagcaag accagcaagt                350

<210> SEQ ID NO 21
<211> LENGTH: 764
<212> TYPE: DNA
<213> ORGANISM: Homo sapiens

<400> SEQUENCE: 21
tcggtgagct acccctctct ttggccgctt gcaccaagca gtgggatgtg gtaagctacc      60
tcctggagaa cccacaccag cccgccagcc tgcaggccac tgactcccag ggcaacacag     120
tcctgcatgc cctagtgatg atctcggaca actcagctga gaacattgca ctggtgacca     180
gcatgtatga tgggctcctc aagctggggg ccgcctctg ccctaccgtg cagcttgagg     240
acatccgcaa cctgcaggat ctcacgcctc tgaagctggc cgccaaggag ggcaagatcg     300
rratyttcaa ggcacatcct tgcaagcggg aagttttcag gactgaagcc acctttccc     360
cgaaagttca ccgagtggtg gctaatgggc cctgtccggg ttgtcgctgt aatgacctgg     420
gctttctgtg gacagctgtg aggagaactc agtgctggrr atcattgcct tcatttgca     480
aragcccgac cgacaccgaa tggtcgtttt ggagcccctg aacaaactgc tgcaggcgaa     540
atgggatctg ctcatcccca gttcttctt aaacttcctg tgtaatctga ttacatgttc     600
atcttcaccg ctgttgccta ccatcagcct accctgaaga agcaggccgc ccctcacctg     660
aaagcggagg ttggaaactc catgctgctg acgggccaca tccttatcct gctagggggg     720
atctacctcc tcgtggggca aaagtggaaa ttttgggggg gaat                       764

<210> SEQ ID NO 22
<211> LENGTH: 884
<212> TYPE: DNA
<213> ORGANISM: Homo sapiens

<400> SEQUENCE: 22
tgtttcctgg ccatcgagtg gtacctgccc ctgcttgtgt ctgcgctggt gctgggctgg      60
ctgaacctgc tttactatac acgtggcttc cagcacacag gcatctacag tgtcatgatc     120

-continued

```
cagaagccct ggtgagcctg agccaggatt ggcgccccga agctcctaca ggccccaatg    180
ccacagagtc agtgcagccc atggagggac aggaggacga gggcaacggg gcccagtaca    240
ggggtatcct ggwagcctcc ttggagctct tcaaattcac catcggcatg ggcgagctgg    300
ccttccagga gcagctgcac ttccgcggca tggtgctgct gctgctgctg gcctacgtgc    360
tgctcaccta catcctgctg ctcaacatgc tcatcgccct cwtgagcgag accgtcaaca    420
gtgtcgccac tgacagctgg agcatctgga agctgcagaa agccatctct gtcctggaga    480
tggagaatgg ctattggtgg tgcaggaaga agcagcgggc aggtgtgatg ctgaccgttg    540
gcactaagcc agatggcagc ccsgatgagc gctggtgctt cagggtggag gaggtgaact    600
gggcttcatg ggagcagacg ctgcctacgc tgtgtgagga cccgtcaggg gcaggtgtcc    660
ctcgaactct cgagaaccct gtcctggctt cccctcccaa ggaggatgag gatggtgcct    720
ctgaggaaaa ctatgtgccc gtccagctcc tccagtccaa ctgatggccc agatgcagca    780
ggaggccaga ggacagagca gaggatcttt ccaaccacat ctgctggctc tggggtccca    840
gtgaattctg gtggcaaata tatattttca ctaammwmaa aaac                    884
```

<210> SEQ ID NO 23
<211> LENGTH: 727
<212> TYPE: PRT
<213> ORGANISM: Homo sapiens
<220> FEATURE:
<221> NAME/KEY: VARIANT
<222> LOCATION: (1)...(727)
<223> OTHER INFORMATION: Xaa = Any Amino Acid

<400> SEQUENCE: 23

```
Met Thr Ser Pro Ser Ser Pro Val Phe Arg Leu Glu Thr Leu Asp
 1               5                  10                  15

Gly Gly Gln Glu Asp Gly Ser Glu Ala Asp Arg Gly Lys Leu Asp Phe
                20                  25                  30

Gly Ser Gly Leu Pro Pro Met Glu Ser Gln Phe Gln Gly Glu Asp Arg
        35                  40                  45

Lys Phe Ala Pro Gln Ile Arg Val Asn Leu Asn Tyr Arg Lys Gly Thr
    50                  55                  60

Gly Ala Ser Gln Pro Asp Pro Asn Arg Phe Asp Arg Asp Arg Leu Phe
65                  70                  75                  80

Asn Ala Val Ser Arg Gly Val Pro Glu Asp Leu Ala Gly Leu Pro Glu
                85                  90                  95

Tyr Leu Ser Lys Thr Ser Lys Tyr Leu Thr Asp Ser Glu Tyr Thr Glu
            100                 105                 110

Gly Ser Thr Gly Lys Thr Cys Leu Met Lys Ala Val Leu Asn Leu Lys
        115                 120                 125

Asp Gly Val Asn Ala Cys Ile Leu Pro Leu Leu Gln Ile Asp Arg Asp
    130                 135                 140

Ser Gly Asn Pro Gln Pro Leu Val Asn Ala Gln Cys Thr Asp Asp Tyr
145                 150                 155                 160

Tyr Arg Gly His Ser Ala Leu His Ile Ala Ile Glu Lys Arg Ser Leu
                165                 170                 175

Gln Cys Val Lys Leu Leu Val Glu Asn Gly Ala Asn Val His Ala Arg
            180                 185                 190

Ala Xaa Xaa Xaa Xaa Xaa Xaa Xaa Xaa Xaa Xaa Xaa Xaa Xaa
        195                 200                 205

Gly Glu Leu Pro Leu Ser Leu Ala Ala Cys Thr Lys Gln Trp Asp Val
```

-continued

```
            210                 215                 220
Val Ser Tyr Leu Leu Glu Asn Pro His Gln Pro Ala Ser Leu Gln Ala
225                 230                 235                 240

Thr Asp Ser Gln Gly Asn Thr Val Leu His Ala Leu Val Met Ile Ser
                245                 250                 255

Asp Asn Ser Ala Glu Asn Ile Ala Leu Val Thr Ser Met Tyr Asp Gly
                260                 265                 270

Leu Leu Gln Ala Gly Ala Arg Leu Cys Pro Thr Val Gln Leu Glu Asp
                275                 280                 285

Ile Arg Asn Leu Gln Asp Leu Thr Pro Leu Lys Leu Ala Ala Lys Glu
290                 295                 300

Gly Lys Ile Xaa Ile Phe Xaa Arg His Ile Leu Ala Ser Gly Lys Phe
305                 310                 315                 320

Ser Gly Leu Lys Pro Pro Phe Pro Arg Lys Phe Thr Glu Trp Trp Leu
                325                 330                 335

Met Gly Pro Val Arg Val Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa Xaa
                355                 360                 365

Pro Asp Arg His Arg Met Val Val Leu Glu Pro Leu Asn Lys Leu Leu
                370                 375                 380

Gln Ala Lys Trp Asp Leu Leu Ile Pro Lys Phe Phe Leu Asn Phe Leu
385                 390                 395                 400

Cys Asn Leu Xaa Tyr Met Phe Ile Phe Thr Ala Val Ala Tyr His Gln
                405                 410                 415

Pro Thr Leu Lys Lys Gln Ala Ala Pro His Leu Lys Ala Glu Val Gly
                420                 425                 430

Asn Ser Met Leu Leu Thr Gly His Ile Leu Ile Leu Leu Gly Gly Ile
                435                 440                 445

Tyr Leu Leu Val Gly Gln Lys Trp Lys Phe Trp Xaa Xaa Xaa Xaa Xaa
                450                 455                 460

Xaa Xaa Xaa Xaa Xaa Xaa Xaa Xaa Xaa Xaa Phe Pro Gly His Arg Val
465                 470                 475                 480

Val Pro Ala Pro Ala Cys Val Cys Ala Gly Ala Gly Leu Ala Glu Pro
                485                 490                 495

Ala Leu Leu Tyr Thr Trp Leu Pro Ala His Arg His Leu Gln Cys His
                500                 505                 510

Asp Pro Glu Ala Leu Val Ser Leu Ser Gln Asp Trp Arg Pro Glu Ala
                515                 520                 525

Pro Thr Gly Pro Asn Ala Thr Glu Ser Val Gln Pro Met Glu Gly Gln
                530                 535                 540

Glu Asp Glu Gly Asn Gly Ala Gln Tyr Arg Gly Ile Leu Xaa Ala Ser
545                 550                 555                 560

Leu Glu Leu Phe Lys Phe Thr Ile Gly Met Gly Glu Leu Ala Phe Gln
                565                 570                 575

Glu Gln Leu His Phe Arg Gly Met Val Leu Leu Leu Leu Ala Tyr
                580                 585                 590

Val Leu Leu Thr Tyr Ile Leu Leu Asn Met Leu Ile Ala Leu Xaa
                595                 600                 605

Ser Glu Thr Val Asn Ser Val Ala Thr Asp Ser Trp Ser Ile Trp Lys
                610                 615                 620

Leu Gln Lys Ala Ile Ser Val Leu Glu Met Glu Asn Gly Tyr Trp Trp
625                 630                 635                 640
```

```
Cys Arg Lys Lys Gln Arg Ala Gly Val Met Leu Thr Val Gly Thr Lys
                645                 650                 655
Pro Asp Gly Ser Pro Asp Glu Arg Trp Cys Phe Arg Val Glu Glu Val
            660                 665                 670
Asn Trp Ala Ser Trp Glu Gln Thr Leu Pro Thr Leu Cys Glu Asp Pro
        675                 680                 685
Ser Gly Ala Gly Val Pro Arg Thr Leu Glu Asn Pro Val Leu Ala Ser
    690                 695                 700
Pro Pro Lys Glu Asp Glu Asp Gly Ala Ser Glu Glu Asn Tyr Val Pro
705                 710                 715                 720
Val Gln Leu Leu Gln Ser Asn
                725

<210> SEQ ID NO 24
<211> LENGTH: 2845
<212> TYPE: DNA
<213> ORGANISM: chicken

<400> SEQUENCE: 24
ttcctataga acagagggag tttgctgaga ctggactatt ctgcagaaga caggatattt      60
ttgcaatatt tggtgatcgg acggagggac acagaaaact gaaaggctg cttgttcatc     120
atgtcttcca ttcttgagaa gatgaagaaa tttggcagtt ctgacataga agaatctgaa     180
gtgacagatg aacacacgga tggggaagac tcagcactgg aaacagctga caacctccag     240
ggtacattca gcaacaaggt gcagccatcc aaaagcaaca tctttgcaag acgtggacgg     300
tttgtgatgg gggattgtga caaggacatg gctccaatgg actccttta ccagatggat     360
cacctgatgg caccttctgt catcaaattt catgccaata tggagagggg gaaacttcac     420
aagctcctgt caacagactc catcacaggc tgctctgaaa agctttcaa attttatgac     480
cgcagaagga tctttgatgc tgtagcccga ggcagcacaa aggacctgga tgatctgctg     540
ctctatctaa ataggacctt gaagcatctc acagatgatg aattcaaaga accagaaact     600
gggaaaacct gcttactgaa agccatgctg aatctacatg atgggaaaaa tgataccatt     660
cccttgctgc tggatattgc aaagaaaact ggaactctga agagtttgt aaatgcagaa     720
tatactgaca actattacaa aggccagact gcactccaca ttgccattga gagaggaac     780
atgtacctgg taaaactctt ggtccagaat ggagcagatg ttcatgcaag agcatgtggg     840
gagttcttca ggaaaatcaa agggaaacct ggttttttat ttggagagct gccctgtcc     900
ctggctgcct gcaccaatca gctctgcatt gtgaaatttc tccttgagaa ccctaccag     960
gctgctgaca ttgctgctga ggactccatg gcaatatgg ttctgcatac tctggtggag    1020
attgcagata atactaagga taataccaag ttcgttacga agatgtacaa taacatattg    1080
atccttggtg ccaaaataaa tcctatcctg aagttggaag aactcaccaa caaaaaggg    1140
ctgactccat taacgttggc agccaaaaca gggaagatag ggattttcgc ttacatcctc    1200
agacgagaga tcaaagatcc tgaatgcaga cacttgtcta ggaagttcac tgaatgggct    1260
tatggaccctg tccattcatc tctttatgac ctgtcctgca tagacacatg tgagaaaat    1320
tcagtgcttg aaattattgc ctacagtagt gaaacaccaa atcgtcatga atgctgctg    1380
gtagagcccc ttaacaggct actgcaagac aagtgggacc gatttgtcaa gcacttattt    1440
tacttcaact tctttgtata tgcaattcat atcagcatcc tcaccacagc tgcctactac    1500
agacctgtgc agaaggggga caagcctccc ttcgcttttg gtcacagcac tgggaatat    1560
```

-continued

```
tttcgagtga ctggagagat actgagtgta ttgggaggac tgtattttt  tttcagaggg    1620 atacagtatt ttgtgcagag gcgcccatca ttgaagacgc tgatagttga cagttacagt    1680
gaagttcttt tcttcgttca ctctttgctc ctcctgagct ctgtggtgct gtacttctgt    1740
ggccaggaac tgtatgtggc ttccatggtc ttctccttgg ctctgggctg ggctaacatg    1800
ctatactaca cccgtggctt ccagcagatg ggcatttact ctgtcatgat tgcaaagatg    1860
atcctaagag acttatgtcg cttcatgttt gtctatctag tattcctctt gggattttcc    1920
acagctgtgg tgactttaat tgaagatgac aatgaggggc aggacacaaa tagctctgaa    1980
tatgcccgat gcagccatac gaaacgaggc cgcacatcct ataacagtct gtattatacc    2040
tgcttggaac ttttcaagtt cactattggg atgggagacc tggagtttac agagaactac    2100
aggttcaagt ctgtgtttgt catccttttg gttctctatg tcatccttac gtacatcctc    2160
ctgctcaata tgcttattgc actgatggga gaaactgtga gcaaaattgc acaggagagc    2220
aagagcatct ggaaactcca gaggcccatc acgatcttgg atattgaaaa cagctacttg    2280
aactgtttga ggcgctcatt ccgatctgga aaaagagtct tggtgggaat cacacctgat    2340
ggccaagatg attacagatg gtgctttaga gttgatgaag tgaactggtc cacgtggaat    2400
acaaatttgg gcataatcaa cgaagatcct gggtgctctg gtgacctcaa acgaaatccc    2460
agttactgta ttaagcctgg tagagtttca gggaaaaatt ggaaaacttt ggttccactt    2520
ttaagagatg gaagcaggag agaagaaaca ccaaaactac cagaagaaat caaattaaaa    2580
cccattttgg aaccttatta tgagccagag gattgtgaga cattgaagga atcgcttcca    2640
aagtcagtct gatcttttgt ttttaagaag gttaattcta gttgtttgtg ttggttctta    2700
caaggaggac aattaaaacg cttccttcat aagagcgggg attttatggaa aaaggccaaa    2760 gaagctagga aatgactgtg tgcaaggatt cattaagtat cttgaataaa ctacttgttg    2820
tttaaaaaaa aaaaaaaaaa aaaaa                                          2845
```

<210> SEQ ID NO 25
<211> LENGTH: 843
<212> TYPE: PRT
<213> ORGANISM: chicken

<400> SEQUENCE: 25

```
Met Ser Ser Ile Leu Glu Lys Met Lys Lys Phe Gly Ser Ser Asp Ile
 1               5                  10                  15

Glu Glu Ser Glu Val Thr Asp Glu His Thr Asp Gly Glu Asp Ser Ala
            20                  25                  30

Leu Glu Thr Ala Asp Asn Leu Gln Gly Thr Phe Ser Asn Lys Val Gln
        35                  40                  45

Pro Ser Lys Ser Asn Ile Phe Ala Arg Arg Gly Arg Phe Val Met Gly
    50                  55                  60

Asp Cys Asp Lys Asp Met Ala Pro Met Asp Ser Phe Tyr Gln Met Asp
65                  70                  75                  80

His Leu Met Ala Pro Ser Val Ile Lys Phe His Ala Asn Met Glu Arg
                85                  90                  95

Gly Lys Leu His Lys Leu Leu Ser Thr Asp Ser Ile Thr Gly Cys Ser
            100                 105                 110

Glu Lys Ala Phe Lys Phe Tyr Asp Arg Arg Ile Phe Asp Ala Val
        115                 120                 125

Ala Arg Gly Ser Thr Lys Asp Leu Asp Asp Leu Leu Leu Tyr Leu Asn
    130                 135                 140
```

-continued

```
Arg Thr Leu Lys His Leu Thr Asp Asp Glu Phe Lys Glu Pro Glu Thr
145                 150                 155                 160

Gly Lys Thr Cys Leu Leu Lys Ala Met Leu Asn Leu His Asp Gly Lys
                165                 170                 175

Asn Asp Thr Ile Pro Leu Leu Asp Ile Ala Lys Lys Thr Gly Thr
            180                 185                 190

Leu Lys Glu Phe Val Asn Ala Glu Tyr Thr Asp Asn Tyr Tyr Lys Gly
        195                 200                 205

Gln Thr Ala Leu His Ile Ala Ile Glu Arg Arg Asn Met Tyr Leu Val
    210                 215                 220

Lys Leu Leu Val Gln Asn Gly Ala Asp Val His Ala Arg Ala Cys Gly
225                 230                 235                 240

Glu Phe Phe Arg Lys Ile Lys Gly Lys Pro Gly Phe Tyr Phe Gly Glu
                245                 250                 255

Leu Pro Leu Ser Leu Ala Ala Cys Thr Asn Gln Leu Cys Ile Val Lys
            260                 265                 270

Phe Leu Leu Glu Asn Pro Tyr Gln Ala Ala Asp Ile Ala Ala Glu Asp
        275                 280                 285

Ser Met Gly Asn Met Val Leu His Thr Leu Val Glu Ile Ala Asp Asn
    290                 295                 300

Thr Lys Asp Asn Thr Lys Phe Val Thr Lys Met Tyr Asn Asn Ile Leu
305                 310                 315                 320

Ile Leu Gly Ala Lys Ile Asn Pro Ile Leu Lys Leu Glu Glu Leu Thr
                325                 330                 335

Asn Lys Lys Gly Leu Thr Pro Leu Thr Leu Ala Ala Lys Thr Gly Lys
            340                 345                 350

Ile Gly Ile Phe Ala Tyr Ile Leu Arg Arg Glu Ile Lys Asp Pro Glu
        355                 360                 365

Cys Arg His Leu Ser Arg Lys Phe Thr Glu Trp Ala Tyr Gly Pro Val
370                 375                 380

His Ser Ser Leu Tyr Asp Leu Ser Cys Ile Asp Thr Cys Glu Lys Asn
385                 390                 395                 400

Ser Val Leu Glu Ile Ile Ala Tyr Ser Ser Glu Thr Pro Asn Arg His
                405                 410                 415

Glu Met Leu Leu Val Glu Pro Leu Asn Arg Leu Leu Gln Asp Lys Trp
            420                 425                 430

Asp Arg Phe Val Lys His Leu Phe Tyr Phe Asn Phe Val Tyr Ala
        435                 440                 445

Ile His Ile Ser Ile Leu Thr Thr Ala Ala Tyr Tyr Arg Pro Val Gln
    450                 455                 460

Lys Gly Asp Lys Pro Pro Phe Ala Phe Gly His Ser Thr Gly Glu Tyr
465                 470                 475                 480

Phe Arg Val Thr Gly Glu Ile Leu Ser Val Leu Gly Gly Leu Tyr Phe
                485                 490                 495

Phe Phe Arg Gly Ile Gln Tyr Phe Val Gln Arg Arg Pro Ser Leu Lys
            500                 505                 510

Thr Leu Ile Val Asp Ser Tyr Ser Glu Val Leu Phe Phe Val His Ser
        515                 520                 525

Leu Leu Leu Leu Ser Ser Val Val Leu Tyr Phe Cys Gly Gln Glu Leu
    530                 535                 540

Tyr Val Ala Ser Met Val Phe Ser Leu Ala Leu Gly Trp Ala Asn Met
545                 550                 555                 560

Leu Tyr Tyr Thr Arg Gly Phe Gln Gln Met Gly Ile Tyr Ser Val Met
```

```
                    565                 570                 575
Ile Ala Lys Met Ile Leu Arg Asp Leu Cys Arg Phe Met Phe Val Tyr
                580                 585                 590
Leu Val Phe Leu Leu Gly Phe Ser Thr Ala Val Val Thr Leu Ile Glu
                595                 600                 605
Asp Asp Asn Glu Gly Gln Asp Thr Asn Ser Ser Glu Tyr Ala Arg Cys
                610                 615                 620
Ser His Thr Lys Arg Gly Arg Thr Ser Tyr Asn Ser Leu Tyr Tyr Thr
625                 630                 635                 640
Cys Leu Glu Leu Phe Lys Phe Thr Ile Gly Met Gly Asp Leu Glu Phe
                645                 650                 655
Thr Glu Asn Tyr Arg Phe Lys Ser Val Phe Ile Leu Leu Val Leu
                660                 665                 670
Tyr Val Ile Leu Thr Tyr Ile Leu Leu Asn Met Leu Ile Ala Leu
                675                 680                 685
Met Gly Glu Thr Val Ser Lys Ile Ala Gln Glu Ser Lys Ser Ile Trp
                690                 695                 700
Lys Leu Gln Arg Pro Ile Thr Ile Leu Asp Ile Glu Asn Ser Tyr Leu
705                 710                 715                 720
Asn Cys Leu Arg Arg Ser Phe Arg Ser Gly Lys Arg Val Leu Val Gly
                725                 730                 735
Ile Thr Pro Asp Gly Gln Asp Asp Tyr Arg Trp Cys Phe Arg Val Asp
                740                 745                 750
Glu Val Asn Trp Ser Thr Trp Asn Thr Asn Leu Gly Ile Ile Asn Glu
                755                 760                 765
Asp Pro Gly Cys Ser Gly Asp Leu Lys Arg Asn Pro Ser Tyr Cys Ile
770                 775                 780
Lys Pro Gly Arg Val Ser Gly Lys Asn Trp Lys Thr Leu Val Pro Leu
785                 790                 795                 800
Leu Arg Asp Gly Ser Arg Arg Glu Glu Thr Pro Lys Leu Pro Glu Glu
                805                 810                 815
Ile Lys Leu Lys Pro Ile Leu Glu Pro Tyr Tyr Glu Pro Glu Asp Cys
                820                 825                 830
Glu Thr Leu Lys Glu Ser Leu Pro Lys Ser Val
                835                 840

<210> SEQ ID NO 26
<211> LENGTH: 135
<212> TYPE: DNA
<213> ORGANISM: Homo sapiens

<400> SEQUENCE: 26
ttcaagttta cgatcgggat gggcgacctg gagttcactg agaactatga cttcaaggct      60
gtcttcatca tcctgctgct ggcctatgta attctcacct acatcctcct gctcaacatg     120
tttatcgctc tcatg                                                      135

<210> SEQ ID NO 27
<211> LENGTH: 32
<212> TYPE: DNA
<213> ORGANISM: Artificial Sequence
<220> FEATURE:
<223> OTHER INFORMATION: consensus

<400> SEQUENCE: 27
tttcaaagtt tcacgatcat atcgggatca tg                                    32
```

```
<210> SEQ ID NO 28
<211> LENGTH: 35
<212> TYPE: DNA
<213> ORGANISM: Artificial Sequence
<220> FEATURE:
<223> OTHER INFORMATION: consensus

<400> SEQUENCE: 28
catgatcaga gatcgcgata tgatcagaca tagtt                                  35

<210> SEQ ID NO 29
<211> LENGTH: 135
<212> TYPE: DNA
<213> ORGANISM: chicken

<400> SEQUENCE: 29
ttcaagttca cgattgggat gggtgacctg gattttcatg aacatgccag attcagatac       60
tttgtcatgc ttctgctgct gcttttgtg atcctcacct acatccttt gctcaacatg        120 cttatagccc ttata                                                       135

<210> SEQ ID NO 30
<211> LENGTH: 135
<212> TYPE: DNA
<213> ORGANISM: chicken

<400> SEQUENCE: 30
ttcaagttca ctattgggat gggagacctg gagtttacag agaactacag gttcaagtct       60
gtgtttgtca tcctttggt tctctatgtc atccttacgt acatcctcct gctcaatatg       120
cttatagccc taatg                                                       135

<210> SEQ ID NO 31
<211> LENGTH: 28
<212> TYPE: DNA
<213> ORGANISM: Homo sapiens

<400> SEQUENCE: 31 tatcttcaa tctttctttc gtgatcta                                           28

<210> SEQ ID NO 32
<211> LENGTH: 17
<212> TYPE: DNA
<213> ORGANISM: Homo sapiens

<400> SEQUENCE: 32
aaaaggggga ccagggc                                                      17

<210> SEQ ID NO 33
<211> LENGTH: 2544
<212> TYPE: DNA
<213> ORGANISM: Homo sapiens

<400> SEQUENCE: 33
ggatccagca aggatgaaga aatggagcag cacagacttg ggggcagctg cggacccact       60
ccaaaaggac acctgcccag acccctgga tggagaccct aactccaggc cacctccagc       120
caagccccag ctctccacgg ccaagagccg cacccggctc tttgggaagg gtgactcgga      180
ggaggctttc ccggtggatt gccctcacga ggaaggtgag ctggactcct gcccgaccat      240
cacagtcagc cctgttatca ccatccagag gccaggagag ggcccaccg gtgccaggct      300 gctgtcccag gactctgtcg ccgccagcac cgagaagacc ctcaggctct atgatcgcag     360
```

```
gagtatcttt gaagccgttg ctcagaataa ctgccaggat ctggagagcc tgctgctctt    420
cctgcagaag agcaagaagc acctcacaga caacgagttc aaagaccctg agacagggaa    480
gacctgtctg ctgaaagcca tgctcaacct gcacgacgga cagaacacca ccatccccct    540
gctcctggag atcgcgcggc aaacggacag cctgaaggag cttgtcaacg ccagctacac    600
ggacagctac tacaagggcc agacagcact gcacatcgcc atcgagagac aacatggc     660
cctggtgacc ctcctggtgg agaacggagc agacgtccag gctgcggccc atggggactt    720
ctttaagaaa accaaaggc ggcctggatt ctacttcggt gaactgcccc tgtccctggc     780
cgcgtgcacc aaccagctgg gcatcgtgaa gttcctgctg cagaactcct ggcagacggc    840
cgacatcagc gccagggact cggtgggcaa cacggtgctg cacgccctgg tggaggtggc    900
cgacaacacg gccgacaaca cgaagtttgt gacgagcatg tacaatgaga ttctgatcct    960
ggggggccaaa ctgcacccga cgctgaagct ggaggagctc accaacaaga agggaatgac    1020
gccgctggct ctggcagctg ggaccgggaa gatcgggtc ttggcctata ttctccagcg     1080
ggagatccag gagcccgagt gcaggcacct gtccaggaag ttcaccgagt gggcctacgg    1140
gcccgtgcac tcctcgctgt acgacctgtc ctgcatcgac acctgcgaga gaactcggt    1200
gctggaggtg atcgcctaca gcagcagcga gcccctaat cgccacgaca tgctcttggt     1260
ggagccgctg aaccgactcc tgcaggacaa gtgggacaga ttcgtcaagc gcatcttcta    1320
cttcaacttc ctggtctact gcctgtacat gatcatcttc accatggctg cctactacag    1380
gcccgtggat ggcttgcctc cctttaagat ggaaaaaact ggagactatt tccgagttac    1440
tggagagatc ctgtctgtgt taggaggagt ctacttcttt ttccgaggga ttcagtattt    1500
cctgcagagg cggccgtcga tgaagaccct gtttgtggac agctacagtg agatgctttt    1560
ctttctgcag tcactgttca tgctggccac cgtggtgctg tacttcagcc acctcaagga    1620
gtatgtggct tccatggtat tctccctggc cttgggctgg accaacatgc tctactacac    1680
ccgcggtttc cagcagatgg gcatctatgc cgtcatgata gagaagatga tcctgagaga    1740
cctgtgccgt tcatgttttg tctacgtcgt cttcttgttc gggttttcca cagcggtggt    1800
gacgctgatt gaagacggga agaatgactc cctgccgtct gagtccacgt cgcacaggtg    1860
gcgggggcct gcctgcaggc cccccgatag ctcctacaac agcctgtact ccacctgcct    1920
ggagctgttc aagttcacca tcggcatggg cgacctggag ttcactgaga actatgactt    1980
caaggctgtc ttcatcatcc tgctgctggc ctatgtaatt ctcacctaca tcctcctgct    2040
caacatgctc atcgccctca tgggtgagac tgtcaacaag atcgcacagg agagcaagaa    2100
catctggaag ctgcagagag ccatcaccat cctggacacg gagaagagct tccttaagtg    2160
catgaggaag gccttccgct caggcaagct gctgcaggtg gggtacacac tgatggcaa    2220
ggacgactac cggtggtgct tcagggtgga cgaggtgaac tggaccacct ggaacaccaa    2280
cgtgggcatc atcaacgaag acccgggcaa ctgtgagggc gtcaagcgca ccctgagctt    2340
ctcccctgcgg tcaagcagag tttcaggcag acactggaag aactttgccc tggtcccccct    2400
tttaagagag gcaagtgctc gagataggca gtctgctcag cccgaggaag tttatctgcg    2460
acagttttca gggtctctga agccagagga cgctgaggtc ttcaagagtc ctgccgcttc    2520
cggggagaag tgaaagccga attc                                            2544
```

<210> SEQ ID NO 34
<211> LENGTH: 839
<212> TYPE: PRT

-continued

<213> ORGANISM: Homo sapiens

<400> SEQUENCE: 34

```
Met Lys Lys Trp Ser Ser Thr Asp Leu Gly Ala Ala Asp Pro Leu
 1               5                  10                  15

Gln Lys Asp Thr Cys Pro Asp Pro Leu Asp Gly Asp Pro Asn Ser Arg
            20                  25                  30

Pro Pro Pro Ala Lys Pro Gln Leu Ser Thr Ala Lys Ser Arg Thr Arg
        35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
            115                 120                 125

Asp Leu Glu Ser Leu Leu Leu Phe Leu Gln Lys Ser Lys Lys His Leu
        130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
                180                 185                 190

Ala Ser Tyr Thr Asp Ser Tyr Tyr Lys Gly Gln Thr Ala Leu His Ile
            195                 200                 205

Ala Ile Glu Arg Arg Asn Met Ala Leu Val Thr Leu Leu Val Glu Asn
        210                 215                 220

Gly Ala Asp Val Gln Ala Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
290                 295                 300

Phe Val Thr Ser Met Tyr Asn Glu Ile Leu Ile Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
        355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400
```

-continued

```
Ala Tyr Ser Ser Ser Glu Thr Pro Asn Arg His Asp Met Leu Leu Val
            405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
            435                 440                 445

Phe Thr Met Ala Ala Tyr Tyr Arg Pro Val Asp Gly Leu Pro Pro Phe
            450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Arg Gly Ile Gln Tyr Phe
            485                 490                 495

Leu Gln Arg Arg Pro Ser Met Lys Thr Leu Phe Val Asp Ser Tyr Ser
            500                 505                 510

Glu Met Leu Phe Phe Leu Gln Ser Leu Phe Met Leu Ala Thr Val Val
            515                 520                 525

Leu Tyr Phe Ser His Leu Lys Glu Tyr Val Ala Ser Met Val Phe Ser
            530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
            565                 570                 575

Leu Cys Arg Phe Met Phe Val Tyr Val Val Phe Leu Phe Gly Phe Ser
            580                 585                 590

Thr Ala Val Val Thr Leu Ile Glu Asp Gly Lys Asn Asp Ser Leu Pro
            595                 600                 605

Ser Glu Ser Thr Ser His Arg Trp Arg Gly Pro Ala Cys Arg Pro Pro
610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
            645                 650                 655

Lys Ala Val Phe Ile Ile Leu Leu Leu Ala Tyr Val Ile Leu Thr Tyr
            660                 665                 670

Ile Leu Leu Leu Asn Met Leu Ile Ala Leu Met Gly Glu Thr Val Asn
            675                 680                 685

Lys Ile Ala Gln Glu Ser Lys Asn Ile Trp Lys Leu Gln Arg Ala Ile
            690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
            725                 730                 735

Asp Asp Tyr Arg Trp Cys Phe Arg Val Asp Glu Val Asn Trp Thr Thr
            740                 745                 750

Trp Asn Thr Asn Val Gly Ile Ile Asn Glu Asp Pro Gly Asn Cys Glu
            755                 760                 765

Gly Val Lys Arg Thr Leu Ser Phe Ser Leu Arg Ser Ser Arg Val Ser
            770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
            805                 810                 815

Gln Phe Ser Gly Ser Leu Lys Pro Glu Asp Ala Glu Val Phe Lys Ser
```

Pro Ala Ala Ser Gly Glu Lys
        835

<210> SEQ ID NO 35
<211> LENGTH: 2380
<212> TYPE: DNA
<213> ORGANISM: Homo sapiens

<400> SEQUENCE: 35

| | | | | | |
|---|---|---|---|---|---|
| cagcctcctc | ctcctaggat | gacctcaccc | tccagctctc | cagttttcag | gttggagaca | 60 |
| ttagatggag | gccaagaaga | tggctctgag | gcggacagag | gaaagctgga | ttttgggagc | 120 |
| gggctgcctc | ccatggagtc | acagttccag | ggcgaggacc | ggaaattcgc | ccctcagata | 180 |
| agagtcaacc | tcaactaccg | aaagggaaca | ggtgccagtc | agccggatcc | aaaccgattt | 240 |
| gaccgagatc | ggctcttcaa | tgcggtctcc | cggggtgtcc | ccgaggatct | ggctggactt | 300 |
| ccagagtacc | tgagcaagac | cagcaagtac | ctcaccgact | cggaatacac | agagggctcc | 360 |
| acaggtaaga | cgtgcctgat | gaaggctgtg | ctgaacctta | aggacggagt | caatgcctgc | 420 |
| attctgccac | tgctgcagat | cgacaggggac | tctggcaatc | ctcagccccct | ggtaaatgcc | 480 |
| cagtgcacag | atgactatta | ccgaggccac | agcgctctgc | acatcgccat | tgagaagagg | 540 |
| agtctgcagt | gtgtgaagct | cctggtggag | aatgggggcca | atgtgcatgc | ccgggcctgc | 600 |
| ggccgcttct | tccagaaggg | ccaagggact | tgcttttatt | tcggtgagct | acccctctct | 660 |
| ttggccgctt | gcaccaagca | gtgggatgtg | gtaagctacc | tcctggagaa | cccacaccag | 720 |
| cccgccagcc | tgcaggccac | tgactcccag | ggcaacacag | tcctgcatgc | cctagtgatg | 780 |
| atctcggaca | actcagctga | gaacattgca | ctggtgacca | gcatgtatga | tgggctcctc | 840 |
| caagctgggg | cccgcctctg | ccctaccgtg | cagcttgagg | acatccgcaa | cctgcaggat | 900 |
| ctcacgcctc | tgaagctggc | cgccaaggag | ggcaagatcg | agattttcag | gcacatcctg | 960 |
| cagcgggagt | tttcaggact | gagccacctt | tcccgaaagt | tcaccgagtg | gtgctatggg | 1020 |
| cctgtccggg | tgtcgctgta | tgacctggct | tctgtggaca | gctgtgagga | gaactcagtg | 1080 |
| ctggagatca | ttgcctttca | ttgcaagagc | ccgcaccgac | accgaatggt | cgttttggag | 1140 |
| cccctgaaca | aactgctgca | ggcgaaatgg | gatctgctca | tccccaagtt | cttcttaaac | 1200 |
| ttcctgtgta | atctgatcta | catgttcatc | ttcaccgctg | ttgcctacca | tcagcctacc | 1260 |
| ctgaagaagc | aggccgcccc | tcacctgaaa | gcggaggttg | gaaactccat | gctgctgacg | 1320 |
| ggccacatcc | ttatcctgct | aggggggatc | tacctcctcg | tgggccagct | gtggtacttc | 1380 |
| tggcggcgcc | acgtgttcat | ctggatctcg | ttcatagaca | gctactttga | aatcctcttc | 1440 |
| ctgttccagg | ccctgctcac | agtggtgtcc | caggtgctgt | gtttcctggc | catcgagtgg | 1500 |
| tacctgcccc | tgcttgtgtc | tgcgctggtg | ctgggctggc | tgaacctgct | ttactataca | 1560 |
| cgtggcttcc | agcacacagg | catctacagt | gtcatgatcc | agaaggtcat | cctgcgggac | 1620 |
| ctgctgcgct | tccttctgat | ctacttagtc | ttccttttcg | gcttcgctgt | agccctggtg | 1680 |
| agcctgagcc | aggaggcttg | gcgccccgaa | gctcctacag | gccccaatgc | cacagagtca | 1740 |
| gtgcagccca | tggagggaca | ggaggacgag | ggcaacgggg | cccagtacag | gggtatcctg | 1800 |
| gaagcctcct | tggagctctt | caaattcacc | atcggcatgg | gcgagctggc | cttccaggag | 1860 |
| cagctgcact | tccgcggcat | ggtgctgctg | ctgctgctgg | cctacgtgct | gctcacctac | 1920 |
| atcctgctgc | tcaacatgct | catcgccctc | atgagcgaga | ccgtcaacag | tgtcgccact | 1980 |

-continued

```
gacagctgga gcatctggaa gctgcagaaa gccatctctg tcctggagat ggagaatggc   2040
tattggtggt gcaggaagaa gcagcgggca ggtgtgatgc tgaccgttgg cactaagcca   2100
gatggcagcc ccgatgagcg ctggtgcttc agggtggagg aggtgaactg ggcttcatgg   2160
gagcagacgc tgcctacgct gtgtgaggac ccgtcagggg caggtgtccc tcgaactctc   2220
gagaaccctg tcctggcttc ccctcccaag gaggatgagg atggtgcctc tgaggaaaac   2280
tatgtgcccg tccagctcct ccagtccaac tgatggccca gatgcagcag gaggccagag   2340
gacagagcag aggatctttc caaccacatc tgctggctct                         2380
```

<210> SEQ ID NO 36
<211> LENGTH: 764
<212> TYPE: PRT
<213> ORGANISM: Homo sapiens

<400> SEQUENCE: 36

```
Met Thr Ser Pro Ser Ser Pro Val Phe Arg Leu Glu Thr Leu Asp
 1               5                  10                  15

Gly Gly Gln Glu Asp Gly Ser Glu Ala Asp Arg Gly Lys Leu Asp Phe
                20                  25                  30

Gly Ser Gly Leu Pro Pro Met Glu Ser Gln Phe Gln Gly Glu Asp Arg
            35                  40                  45

Lys Phe Ala Pro Gln Ile Arg Val Asn Leu Asn Tyr Arg Lys Gly Thr
        50                  55                  60

Gly Ala Ser Gln Pro Asp Pro Asn Arg Phe Asp Arg Asp Arg Leu Phe
    65                  70                  75                  80

Asn Ala Val Ser Arg Gly Val Pro Glu Asp Leu Ala Gly Leu Pro Glu
                85                  90                  95

Tyr Leu Ser Lys Thr Ser Lys Tyr Leu Thr Asp Ser Glu Tyr Thr Glu
                100                 105                 110

Gly Ser Thr Gly Lys Thr Cys Leu Met Lys Ala Val Leu Asn Leu Lys
            115                 120                 125

Asp Gly Val Asn Ala Cys Ile Leu Pro Leu Leu Gln Ile Asp Arg Asp
        130                 135                 140

Ser Gly Asn Pro Gln Pro Leu Val Asn Ala Gln Cys Thr Asp Asp Tyr
    145                 150                 155                 160

Tyr Arg Gly His Ser Ala Leu His Ile Ala Ile Glu Lys Arg Ser Leu
                165                 170                 175

Gln Cys Val Lys Leu Leu Val Glu Asn Gly Ala Asn Val His Ala Arg
            180                 185                 190

Ala Cys Gly Arg Phe Phe Gln Lys Gly Gln Gly Thr Cys Phe Tyr Phe
        195                 200                 205

Gly Glu Leu Pro Leu Ser Leu Ala Ala Cys Thr Lys Gln Trp Asp Val
    210                 215                 220

Val Ser Tyr Leu Leu Glu Asn Pro His Gln Pro Ala Ser Leu Gln Ala
225                 230                 235                 240

Thr Asp Ser Gln Gly Asn Thr Val Leu His Ala Leu Val Met Ile Ser
                245                 250                 255

Asp Asn Ser Ala Glu Asn Ile Ala Leu Val Thr Ser Met Tyr Asp Gly
            260                 265                 270

Leu Leu Gln Ala Gly Ala Arg Leu Cys Pro Thr Val Gln Leu Glu Asp
        275                 280                 285

Ile Arg Asn Leu Gln Asp Leu Thr Pro Leu Lys Leu Ala Ala Lys Glu
    290                 295                 300
```

```
Gly Lys Ile Glu Ile Phe Arg His Ile Leu Gln Arg Glu Phe Ser Gly
305                 310                 315                 320

Leu Ser His Leu Ser Arg Lys Phe Thr Glu Trp Cys Tyr Gly Pro Val
            325                 330                 335

Arg Val Ser Leu Tyr Asp Leu Ala Ser Val Asp Ser Cys Glu Glu Asn
            340                 345                 350

Ser Val Leu Glu Ile Ile Ala Phe His Cys Lys Ser Pro His Arg His
            355                 360                 365

Arg Met Val Val Leu Glu Pro Leu Asn Lys Leu Leu Gln Ala Lys Trp
    370                 375                 380

Asp Leu Leu Ile Pro Lys Phe Phe Leu Asn Phe Leu Cys Asn Leu Ile
385                 390                 395                 400

Tyr Met Phe Ile Phe Thr Ala Val Ala Tyr His Gln Pro Thr Leu Lys
                405                 410                 415

Lys Gln Ala Ala Pro His Leu Lys Ala Glu Val Gly Asn Ser Met Leu
            420                 425                 430

Leu Thr Gly His Ile Leu Ile Leu Leu Gly Gly Ile Tyr Leu Leu Val
            435                 440                 445

Gly Gln Leu Trp Tyr Phe Trp Arg Arg His Val Phe Ile Trp Ile Ser
    450                 455                 460

Phe Ile Asp Ser Tyr Phe Glu Ile Leu Phe Leu Phe Gln Ala Leu Leu
465                 470                 475                 480

Thr Val Val Ser Gln Val Leu Cys Phe Leu Ala Ile Glu Trp Tyr Leu
                485                 490                 495

Pro Leu Leu Val Ser Ala Leu Val Leu Gly Trp Leu Asn Leu Leu Tyr
            500                 505                 510

Tyr Thr Arg Gly Phe Gln His Thr Gly Ile Tyr Ser Val Met Ile Gln
            515                 520                 525

Lys Val Ile Leu Arg Asp Leu Leu Arg Phe Leu Leu Ile Tyr Leu Val
    530                 535                 540

Phe Leu Phe Gly Phe Ala Val Ala Leu Val Ser Leu Ser Gln Glu Ala
545                 550                 555                 560

Trp Arg Pro Glu Ala Pro Thr Gly Pro Asn Ala Thr Glu Ser Val Gln
                565                 570                 575

Pro Met Glu Gly Gln Glu Asp Glu Gly Asn Gly Ala Gln Tyr Arg Gly
            580                 585                 590

Ile Leu Glu Ala Ser Leu Glu Leu Phe Lys Phe Thr Ile Gly Met Gly
            595                 600                 605

Glu Leu Ala Phe Gln Glu Gln Leu His Phe Arg Gly Met Val Leu Leu
610                 615                 620

Leu Leu Leu Ala Tyr Val Leu Leu Thr Tyr Ile Leu Leu Leu Asn Met
625                 630                 635                 640

Leu Ile Ala Leu Met Ser Glu Thr Val Asn Ser Val Ala Thr Asp Ser
                645                 650                 655

Trp Ser Ile Trp Lys Leu Gln Lys Ala Ile Ser Val Leu Glu Met Glu
            660                 665                 670

Asn Gly Tyr Trp Trp Cys Arg Lys Lys Gln Arg Ala Gly Val Met Leu
            675                 680                 685

Thr Val Gly Thr Lys Pro Asp Gly Ser Pro Asp Glu Arg Trp Cys Phe
    690                 695                 700

Arg Val Glu Glu Val Asn Trp Ala Ser Trp Glu Gln Thr Leu Pro Thr
705                 710                 715                 720

Leu Cys Glu Asp Pro Ser Gly Ala Gly Val Pro Arg Thr Leu Glu Asn
```

```
                            725                 730                 735
            Pro Val Leu Ala Ser Pro Pro Lys Glu Asp Glu Asp Gly Ala Ser Glu
                740                 745                 750
            Glu Asn Tyr Val Pro Val Gln Leu Leu Gln Ser Asn
                    755                 760
```

<210> SEQ ID NO 37
<211> LENGTH: 21
<212> TYPE: DNA
<213> ORGANISM: Homo sapiens

<400> SEQUENCE: 37
ggcgacctgg agttcactga g                                              21

<210> SEQ ID NO 38
<211> LENGTH: 21
<212> TYPE: DNA
<213> ORGANISM: Homo sapiens

<400> SEQUENCE: 38
gagcaggagg atgtaggtga g                                              21

<210> SEQ ID NO 39
<211> LENGTH: 226
<212> TYPE: DNA
<213> ORGANISM: Homo sapiens

<400> SEQUENCE: 39
ctgcagcttc cagatgttct tgctctcctg tgcgatcttg ttgacagtct cacccatgag    60
ggcgatgagc atgttgagca ggaggatgta ggtgagaatt acataggcca gcagcaggat   120
gatgaagaca gccttgaagt catagttctc agtgaactcc aggtcgccca tgccgatggt   180
gaacttgaac agctccaggc aggtggagta caggctgttg taggag                  226

<210> SEQ ID NO 40
<211> LENGTH: 226
<212> TYPE: DNA
<213> ORGANISM: R. rattus

<400> SEQUENCE: 40
gagaatgttg tcggacataa ggtgtacaga cctcgacaag ttcaagtggt agccgtaccc    60
gctggacctc aagtgactct tgatgctgaa gttccgacag aagtagtagg acaatgaccg   120
gatacactaa gagtggatgt aggaagacga gttgtacgag taacgagagt acccactctg   180
gcagttgttc taacgtgttc tctcgttctt gtagaccttc gacgtc                  226

<210> SEQ ID NO 41
<211> LENGTH: 145
<212> TYPE: DNA
<213> ORGANISM: Homo sapiens
<220> FEATURE:
<221> NAME/KEY: misc_feature
<222> LOCATION: (1)...(145)
<223> OTHER INFORMATION: n = A,T,C or G

<400> SEQUENCE: 41
aagacctcag cgtcctctgg cttcagagac cctgnaaaac tgtcgcagat aaacttcctc    60
gggctgagca nactgcctat ctcgagcact tgcctctctt aaaaggggga ccagggcaaa   120
gttcttccag tgtctgcctg aaact                                         145

```
<210> SEQ ID NO 42
<211> LENGTH: 144
<212> TYPE: DNA
<213> ORGANISM: Homo sapiens
<220> FEATURE:
<221> NAME/KEY: misc_feature
<222> LOCATION: (1)...(144)
<223> OTHER INFORMATION: n = A,T,C or G

<400> SEQUENCE: 42
tcaaagtccg tctgtgacct tcttgaaacg ggaccagggg gaaaattctc tccgttcang      60
agctntatcc gtcagacgag tcgggctcct tcaaatagac gctgtcaaaa gtcccagaga     120
tttcggtctc ctgcgactcc agaa                                            144

<210> SEQ ID NO 43
<211> LENGTH: 219
<212> TYPE: DNA
<213> ORGANISM: Homo sapiens

<400> SEQUENCE: 43
cccactccaa aaggacacct gcccagaccc cctggatgga gaccctaact ccaggccacc      60
tccagccaag ccccagctct ccacggccaa gagccgcacc cggctctttg ggaagggtga     120
ctcggaggag gctttcccgg tggattgccc tcacgaggaa ggtgagctgg actcctgccc     180
gaccatcaca gtcagccctg ttatcaccat ccagaggcc                            219

<210> SEQ ID NO 44
<211> LENGTH: 219
<212> TYPE: DNA
<213> ORGANISM: R. rattus

<400> SEQUENCE: 44
cccaccccaa gagaactcct gcctggaccc tccagacaga gaccctaact gcaagccacc      60
tccagtcaag ccccacatct tcactaccag gagtcgtacc cggctttttg ggaagggtga     120
ctcggaggag gcctctcccc tggactgccc ttatgaggaa ggcgggctgg cttcctgccc     180
tatcatcact gtcagctctg ttctaactat ccagaggcc                            219

<210> SEQ ID NO 45
<211> LENGTH: 91
<212> TYPE: PRT
<213> ORGANISM: Homo sapiens
<220> FEATURE:
<221> NAME/KEY: VARIANT
<222> LOCATION: (1)...(91)
<223> OTHER INFORMATION: Xaa = Any Amino Acid

<400> SEQUENCE: 45

Met Lys Lys Trp Ser Ser Thr Asp Leu Gly Ala Ala Asp Pro Leu
 1               5                  10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Arg Xaa Arg Pro
                85                  90
```

```
<210> SEQ ID NO 46
<211> LENGTH: 91
<212> TYPE: PRT
<213> ORGANISM: R. rattus

<400> SEQUENCE: 46

Met Glu Gln Arg Ala Ser Leu Asp Ser Glu Glu Ser Glu Ser Pro Pro
1               5                   10                  15

Gln Glu Asn Ser Cys Leu Asp Pro Pro Asp Arg Asp Pro Asn Cys Lys
            20                  25                  30

Pro Pro Pro Val Lys Pro His Ile Phe Thr Thr Arg Ser Arg Thr Arg
            35                  40                  45

Leu Phe Gly Lys Gly Asp Ser Glu Glu Ala Ser Pro Leu Asp Cys Pro
        50                  55                  60

Tyr Glu Glu Gly Gly Leu Ala Ser Cys Pro Ile Ile Thr Val Ser Ser
65                  70                  75                  80

Val Leu Thr Ile Gln Arg Pro Gly Asp Gly Pro
                85                  90

<210> SEQ ID NO 47
<211> LENGTH: 24
<212> TYPE: DNA
<213> ORGANISM: Homo sapiens

<400> SEQUENCE: 47
agaaatggag cagcacagac ttgg                                      24

<210> SEQ ID NO 48
<211> LENGTH: 23
<212> TYPE: DNA
<213> ORGANISM: Homo sapiens

<400> SEQUENCE: 48
tcacttctcc ccggaagcgg cag                                       23
```

NUCLEIC ACID SEQUENCES ENCODING CAPSAICIN RECEPTOR AND CAPSAICIN RECEPTOR-RELATED POLYPEPTIDES AND USES THEREOF

CROSS-REFERENCES TO RELATED APPLICATIONS

This application is a continuation of U.S. patent application Ser. No. 09/235,451, filed Jan. 22, 1999, now U.S. Pat. No. 6,335,180, which is a continuation-in-part of: 1) U.S. Provisional patent application Ser. No. 60/072,151, filed Jan. 22, 1998; and 2) U.S. patent application Ser. No. 08/915, 461, filed Aug. 20, 1997, now abandoned; and 3) PCT international application PCT/US98/17466, filed Aug. 20, 1998, which PCT International application was published in English on Jul. 29, 1999 as WO 9937675, each of which applications are incorporated herein by reference.

FIELD OF THE INVENTION

The present invention relates to nucleic acid and amino acid sequences encoding a receptor for vanilloid compound and polypeptides related to such vanilloid compound receptors, and to the use of these sequences in the diagnosis, study, and treatment of disease.

BACKGROUND OF THE INVENTION

Pain is initiated when the peripheral terminals of a particular group of sensory neurons, called nociceptors, are activated by noxious chemical, mechanical, or thermal stimuli. These neurons, whose cell bodies are located in various sensory ganglia, transmit information regarding tissue damage to pain processing centers in the spinal cord and brain (Fields Pain (McGraw-Hill, New York, 1987)). Nociceptors are characterized, in part, by their sensitivity to capsaicin, a natural product of capsicum peppers that is the active ingredient of many "hot" and spicy foods. In mammals, exposure of nociceptor terminals to capsaicin leads initially to the perception of pain and the local release of neurotransmitters. With prolonged exposure, these terminals become insensitive to capsaicin, as well as to other noxious stimuli (Szolcsanyi in *Capsaicin in the Study of Pain* (ed. Wood) pgs. 255–272 (Academic Press, London, 1993)). This latter phenomenon of nociceptor desensitization underlies the seemingly paradoxical use of capsaicin as an analgesic agent in the treatment of painful disorders ranging from viral and diabetic neuropathies to rheumatoid arthritis (Campbell in *Capsaicin and the Study of Pain* (ed. Wood) pgs. 255–272 (Academic Press, London, 1993); Szallasi et al. 1996 Pain 68:195–208). While some of this decreased sensitivity to noxious stimuli may reflect reversible changes in the nociceptor, such as depletion of inflammatory mediators, the long-term loss of responsiveness can be explained by death of the nociceptor or destruction of its peripheral terminals following capsaicin exposure (Jancso et al. 1977 Nature 270:741–743; Szolcsanyi, supra).

Responsivity to capsaicin has been used to define sensory afferent fibers that transmit signals in response to noxious stimuli (chemical, thermal, and mechanical stimuli); however, the precise mechanism of action has remained unclear. Electrophysiological (Bevan et al. 1990 Trends Pharmacol. Sci 11:330–333; Oh et al. 1996 J. Neuroscience 16:1659–1667) and biochemical (Wood et al. 1988 J. Neuroscience 8:3208–3220) studies have clearly shown that capsaicin excites nociceptors by increasing plasma membrane conductance through formation or activation of non-selective cation channels. While the hydrophobic nature of capsaicin has made it difficult to rule out the possibility that its actions are mediated by direct perturbation of membrane lipids (Feigin et al. 1995 Neuroreport 6:2134–2136), it has been generally accepted that this compounds acts at a specific receptor site on or within sensory neurons due to observations that capsaicin derivatives show structure-function relationships and evoke dose-dependent responses (Szolcsanyi et al. 1975 Drug. Res. 25:1877–1881; Szolcsanyi et al. 1976 Drug Res. 26:33–37)). The development of capsazepine, a competitive capsaicin antagonist (Bevan et al. 1992 Br. J. Pharmacol. 107:544–552) and the discovery of resiniferatoxin, an ultrapotent capsaicin analogue from Euphorbia plants that mimics the cellular actions of capsaicin (deVries et al. 1989 Life Sci. 44:711–715; Szallasi et al. 1989 Neuroscience 30:515–520) further suggest that the capsaicin mediates its effects through a receptor. The nanomolar potency of resiniferatoxin has facilitated its use as a high affinity radioligand to visualize saturable, capsaicin- and capsazepine-sensitive binding sites on nociceptors (Szallasi 1994 Gen. Pharmac. 25:223–243). Because a vanilloid moiety constitutes an essential structural component of capsaicin and resiniferatoxin, the proposed site of action of these compounds has been more generally referred to as the vanilloid receptor (Szallasi 1994 supra). The action of capsaicin, resiniferatoxin, and the antagonist capsazepine have been well characterized physiologically using primary neuronal cultures (see, e.g., Szolcsanyi, "Actions of Capsaicin on Sensory Receptors," Bevan et al. "Cellular Mechanisms of the Action of Capsaicin," and James et al. "The Capsaicin Receptor," all in Capsaicin in the Study of Pain, 1993 Academic Press Limited, pgs. 1–26, 2744, and 83–104, respectively; Bevan et al. 1990, supra).

The analgesic properties of capsaicin and capsaicinoids are of much interest for their uses in the treatment of pain and inflammation associated with a variety of disorders (see, e.g., Fusco et al. 1997 Drugs 53:909–914; Towheed et al. 1997 Semin. Arthritis Rheum 26:755–770; Appendino et al. 1997 Life Sci 60:681–696 (describing activities and application of resiniferatoxin); Campbell et al. "Clinical Applications of Capsaicin and Its Analogues" in Capsaicin in the Study of Pain 1993, Academic Press pgs. 255–272). Although capsaicin and capsaicin related compounds can evoke the sensation of pain, cause hyperalgesia, activate autonomic reflexes (e.g., elicit changes in blood pressure), and cause release of peptides and other putative transmitters from nerve terminals (e.g., to induce bronochoconstriction and inflammation), prolonged exposure of sensory neurons to these compounds leads to desensitization of the neurons to multiple modalities of noxious sensory stimuli without compromising normal mechanical sensitivity or motor function, and without apparent central nervous system depression. It is this final phenomena that makes capsaicins and related compounds of great interest and potential therapeutic value.

Despite the intense interest in capsaicin and related compounds and their effects upon sensory afferent, the receptor (s) through which these compounds mediate their effects have eluded isolation and molecular characterization. Thus, the development of elegant systems for screening or characterizing new capsaicin receptor-binding compounds, or for identifying endogenous, tissue-derived mediators of pain and/or inflammation, have been severely hampered. To date the only means of assessing the activity of compounds as capsaicin receptor agonists or antagonists has been to examined their effects on sensory neurons in culture or in intact animals. The present invention solves this problem.

SUMMARY

The present invention features vanilloid receptor polypeptides and vanilloid receptor-related polypeptides, specifically the capsaicin receptor and capsaicin receptor-related polypeptides, as well as nucleotide sequences encoding capsaicin receptor and capsaicin receptor-related polypeptides. In related aspects the invention features expression vectors and host cells comprising polynucleotides that encode capsaicin receptor or capsaicin receptor-related polypeptide. In other related aspects, the invention features transgenic animals having altered capsaicin receptor expression, due to, for example, the presence of an exogenous wild-type or modified capsaicin receptor-encoding polynucleotide sequence. The present invention also relates to antibodies that bind specifically to a capsaicin receptor polypeptide and/or capsaicin receptor-related polypeptide, and methods for producing capsaicin receptor and capsaicin receptor-related polypeptides.

In one aspect the invention features a method for identifying compounds that bind a capsaicin receptor polypeptide, preferably a compound that binds a capsaicin receptor polypeptide and affects a cellular response associated with capsaicin receptor biological activity (e.g., intracellular calcium flux).

In another aspect the invention features a method for detecting a vanilloid compound in a sample, where the vanilloid compound has activity in binding a capsaicin receptor polypeptide, by contacting a sample suspected of containing a vanilloid compound with a cell (e.g., an oocyte (e.g., an amphibian oocyte) or a mammalian cell) expressing a capsaicin receptor polypeptide and detecting an alteration of a cellular response associated with capsaicin receptor activity in the capsaicin receptor-expressing host cell. Preferably, the cellular response associated with capsaicin receptor activity is an alteration of intracellular calcium levels in the capsaicin receptor-expressing host cell. The method can be used to detect vanilloid compounds in samples derived from natural products (e.g., natural product extracts) or can be used to screen candidate compounds for use as analgesics (e.g., vanilloid analogs, therapeutic antibodies, antisense oligonucleotides, capsaicin receptor-encoding nucleotides for replacement gene therapy), flavor-enhancing agents, etc.

Yet another aspect of the invention relates to use of capsaicin receptor polypeptides and specific antibodies thereto for the diagnosis and treatment of human disease and painful syndromes.

In another aspect the invention features transgenic, non-human mammals expressing a capsaicin receptor-encoding transgene, and use of such transgenic mammals for use in screening of candidate capsaicin receptor agonist and antagonist compounds.

A primary object of the invention is to provide isolated polynucleotides for use in expression of capsaicin receptor and capsaicin receptor-related polypeptides (e.g., in a recombinant host cell or in a target cell as part of organochemotherapy) and for use in, for example, identification of capsaicin receptor-binding compounds (especially those compounds that affect capsaicin receptor-mediated activity).

The invention will now be described in further detail.

BRIEF DESCRIPTION OF THE FIGURES

FIG. 1A shows the putative domains present in the capsaicin receptor amino acid sequence. Open boxes delineate ankyrin repeat domains; black boxes indicate predicted transmembrane domains; and the grey box indicates a possible pore-loop region. Bullets denote predicted protein kinase A phosphorylation sites.

FIG. 1B shows the predicted membrane topology and domain structure of the capsaicin receptor. Open circles labeled "A" denote ankyrin domains; black areas denote transmembrane domains; and the grey shaded area indicates a possible pore-loop region. "i" and "o" denote the inner and outer membrane leaflets, respectively.

FIG. 1C shows the alignment of the capsaicin receptor VR1 with related sequences. Identical residues are darkly shaded and conservative substitutions are lightly shaded.

FIG. 6A through FIG. 6F are graphs showing the effects of extracellular calcium upon capsaicin-induced current in whole-cell voltage clamp experiments.

FIG. 9A is a graph showing the effects of capsaicin and resiniferatoxin upon current in whole-cell voltage clamp experiments in Xenopus oocytes expressing the capsaicin receptor. Bars denote duration of agonist application. Membrane currents were recorded in the whole cell voltage clamp configuration ($V_{hold}$=−40 mV).

FIG. 9B is a graph showing the concentration-response curve for capsaicin (squares) and resiniferatoxin (open circles) in VR1-expressing oocytes. In FIG. 9B, the membrane currents were normalized in each oocyte to a response obtained with 1 μM capsaicin and expressed as a percent of maximal response to capsaicin. Each point represents mean values (±s.e.m.) from 5 independent oocytes.

FIG. 10A is a graph showing the effects of capsazepine upon capsaicin-induced current in whole cell voltage clamp experiments. Slash marks represent wash out periods of 2 and 3 min, respectively (n=3). cap=capsaicin; cpz=capsazepine; RR=ruthenium red. Each point represents 4 independent oocytes. Current response were normalized to that elicited by capsaicin in each oocyte (0.6 μM, open diamond). Slash marks denote 2 and 12 minute wash out periods, respectively (n=3).

FIG. 10B is a graph showing the capsazepine inhibition curve of capsaicin response in whole cell voltage clamp studies.

DETAILED DESCRIPTION OF THE INVENTION

Definitions

Figure 2:
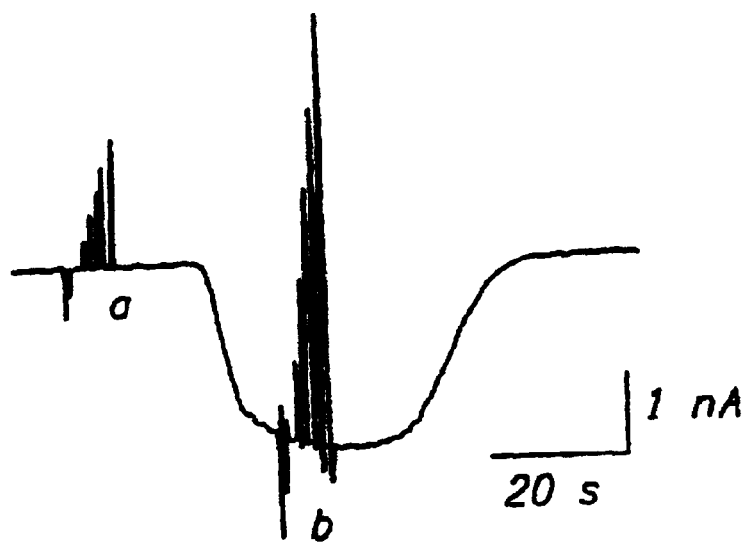
FIG. 2 is a current trace of whole cell voltage clamp analysis of capsaicin receptor-expressing HEK293 cells.

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a capsaicin receptor-encoding polynucleotide or a capsaicin receptor-related polypeptide-encoding polynucleotide), "polynucleotide" is meant to encompass polynucleotides that encode a polypeptide that is functionally equivalent to the recited polypeptide, e.g., polynucleotides that are degenerate variants, or polynucleotides that encode biologically active variants or fragments of the recited polypeptide. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule.

By "antisense polynucleotide" is mean a polynucleotide having a nucleotide sequence complementary to a given polynucleotide sequence (e.g., a polynucleotide sequence encoding a capsaicin receptor) including polynucleotide sequences associated with the transcription or translation of the given polynucleotide sequence (e.g., a promoter of a polynucleotide encoding capsaicin receptor), where the antisense polynucleotide is capable of hybridizing to a capsaicin receptor polynucleotide sequence. Of particular interest are antisense polynucleotides capable of inhibiting transcription and/or translation of a capsaicin receptor-encoding or capsaicin receptor-related polypeptide-encoding polynucleotide either in vitro or in vivo.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al 1993 Anticancer Drug Des 8:53–63).

As used herein, "capsaicin receptor" or "capsaicin receptor polypeptide" means a recombinant or nonrecombinant polypeptide having an amino acid sequence of i) a native capsaicin receptor polypeptide, ii) a biologically active fragment of a capsaicin receptor polypeptide, iii) biologically active polypeptide analogs of a capsaicin receptor polypeptide, or iv) a biologically active variant of a capsaicin receptor polypeptide. Capsaicin receptor polypeptides of the invention can be obtained from any species, particularly mammalian, including human, rodentia (e.g., murine or rat), bovine, ovine, porcine, murine, or equine, preferably rat or human, from any source whether natural, synthetic, semi-synthetic or recombinant. The term "capsaicin receptor" as used herein encompasses the vanilloid receptor subtype 1(VR1) described in detail herein, but is not meant to be limited to VR1, and particularly may be generically used to refer to the receptor subtypes VR1 and VR2.

As used herein, "capsaicin receptor-related polypeptide" or "vanilloid-like receptor (VLR) polypeptide" means a recombinant or nonrecombinant polypeptide having an amino acid sequence of i) a native capsaicin receptor-related polypeptide, ii) a biologically active fragment of a capsaicin receptor-related polypeptide, iii) biologically active polypeptide analogs of a capsaicin receptor-related polypeptide, or iv) a biologically active variant of a capsaicin receptor-related polypeptide, herein referred to as "VRRP-1", "VLR1," or "VR2". Capsaicin receptor polypeptides of the invention can be obtained from any species, particularly a mammalian species, including human, rodentia (e.g., murine or rat), bovine, ovine, porcine, murine, or equine, preferably rat or human, from any source whether natural, synthetic, semi-synthetic or recombinant The term "capsaicin receptor-related polypeptide" as used herein also encompasses any polypeptide having at least about 40% identity, preferably at least about 45% identity, more preferably at least about 49% identity to an amino acid sequence of a capsaicin receptor polypeptide of the same species (e.g., rat or human capsaicin receptor polypeptide). The term "capsaicin receptor-related polypeptide-encoding sequence" also encompasses a nucleotide sequence having at least about 50% identity, preferably at least about 55% identity, more preferably at least about 59% identity to a nucleotide sequence of a capsaicin receptor polypeptide of the same species. In one embodiment, the capsaicin receptor-related polypeptide interacts with capsaicin receptor. "Capsaicin receptor-related polypeptide" as used herein encompasses the vanilloid receptor-related polypeptide 1 (VRRP-1) described in detail herein, but is not meant to be limited to VRRP-1.

As used herein, "antigenic amino acid sequence" means an amino acid sequence that, either alone or in association with a carrier molecule, can elicit an antibody response in a mammal.

A "variant" of a capsaicin receptor or capsaicin receptor-related polypeptide is defined as an amino acid sequence that is altered by one or more amino acids. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, inserted or deleted without abolishing biological or immunological activity can be found using computer programs well known in the art, for example, DNAStar software.

A "deletion" is defined as a change in either amino acid or nucleotide sequence in which one or more amino acid or nucleotide residues, respectively, are absent as compared to an amino acid sequence or nucleotide sequence of a naturally occurring capsaicin receptor or capsaicin receptor-related polypeptide.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring capsaicin receptor or capsaicin receptor-related polypeptide.

A "substitution" results from the replacement of one or more amino acids or nucleotides by different amino acids or nucleotides, respectively as compared to an amino acid sequence or nucleotide sequence of a naturally occurring capsaicin receptor or capsaicin receptor-related polypeptide.

The term "biologically active" refers to capsaicin receptor polypeptide or capsaicin receptor-related polypeptide having structural, regulatory, or biochemical functions of a naturally occurring capsaicin receptor polypeptide or capsaicin receptor-related polypeptide, respectively. Likewise, "immunologically active" defines the capability of the natural, recombinant or synthetic capsaicin receptor (or capsaicin receptor-related polypeptide), or any oligopeptide thereof, to induce a specific immune response in appropriate animals or cells and to bind with specific antibodies.

The term "derivative" as used herein refers to the chemical modification of a nucleic acid encoding a capsaicin receptor or a capsaicin receptor-related polypeptide. Illustrative of such modifications would be replacement of hydrogen by an alkyl, acyl, or amino group. A nucleic acid derivative would encode a polypeptide which retains essential biological characteristics of a natural capsaicin receptor or capsaicin receptor-related polypeptide.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

"Stringency" typically occurs in a range from about Tm–5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs 1994 Dictionary of Biotechnology, Stockton Press, New York N.Y.). Amplification as carried out in the polymerase chain reaction technologies is described in Dieffenbach et al. 1995, PCR Primer, a Laboratory Manual, Cold Spring Harbor Press, Plainview N.Y.

"Sequence identity" as used herein generally refers to a sequence identity of nucleotide or amino acid sequence, where the sequence identity is generally at least about 65%, preferably at least about 75%, more preferably at least about 85%, and can be greater than at least about 90% or more as determined by the Smith-Waterman homology search algorithm as implemented in MPSRCH program (Oxford Molecular). For the purposes of this invention, a preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

The term "transgene" is used herein to describe genetic material which has been or is about to be artificially inserted into the genome of a mammalian, particularly a mammalian cell of a living animal.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

A "knock-out" of a target gene means an alteration in the sequence of the gene that results in a decrease of function of the target gene, preferably such that target gene expression is undetectable or insignificant. For example, a knock-out of a capsaicin receptor gene means that function of the capsaicin receptor has been substantially decreased so that capsaicin receptor expression is not detectable or only present at insignificant levels. "Knock-out" transgenics of the invention can be transgenic animals having a heterozygous or homozygous knock-out of the capsaicin receptor gene or capsaicin receptor-related polypeptide encoding sequence. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of the target gene, e.g., by introduction of an additional copy of the target gene, or by operatively inserting a regulatory sequence that provides for enhanced expression of an endogenous copy of the target gene. For example, "knock-in" transgenics of the invention can be transgenic animals having a heterozygous or homozygous knock-in of the capsaicin receptor gene. "Knock-ins" also encompass conditional knock-ins.

The major genetic sequences provided herein are as follows:

| SEQ ID NO | Sequence |
|---|---|
| 1 | Rat VR1 cDNA sequence |
| 2 | Rat VR1 amino acid sequence |
| 3 | Rat VRRP-1 (VR2) cDNA sequence |
| 4 | Rat VRRP-1 (VR2) amino acid sequence |
| 5 | Human VRRP-1 consensus sequence, region A |
| 6 | Human VRRP-1 consensus sequence, region B |
| 7 | Human VRRP-1 consensus sequence, region C |
| 8 | EST AA321554 DNA sequence |
| 9 | EST AA321554 amino acid sequence |
| 10 | mouse VR1 cDNA sequence |
| 11 | mouse VR1 amino acid sequence |
| 12 | primer |
| 13 | primer |
| 14 | Rat VR1 amino acid sequence |
| 15 | Human T11251 amino acid sequence |
| 16 | Caliphora z80230 amino acid sequence |
| 17 | Drosophila TRP amino acid sequence |
| 18 | Bocine x99792 amino acid sequence |
| 19 | E. elegans z72508 amino acid sequence |
| 20 | Human VRRP-1 (VR2) DNA sequence |
| 21 | Human VRRP-1 (VR2) DNA sequence |
| 22 | Human VRRP-1 (VR2) DNA sequence |
| 23 | Human VRRP-1 (VR2) amino acid sequence |
| 24 | Chicken VR1 cDNA sequence |
| 25 | Chicken VR1 amino acid sequence |
| 26 | Human VR1 cDNA sequence |
| 27 | Human VR1 amino acid sequence |
| 33 | Human VR1 cDNA sequence |
| 34 | Human VR1 amino acid sequence |
| 35 | Human VR2 cDNA sequence |
| 36 | Human VR2 amino acid sequence |

Overview of the Invention

The present invention is based upon the identification and isolation of a polynucleotide sequence encoding a capsaicin receptor polypeptide (e.g., the vanilloid receptor subtype 1 (VR1) polypeptide described herein) and a capsaicin receptor-related polypeptide (e.g., the vanilloid receptor-related polypeptide 1 (VRRP-1; or VR2) described herein). The corresponding genetic sequences are provided in the Seqlist, and are listed in the table provided above. Accordingly, the present invention encompasses such polynucleotides encoding capsaicin receptor and/or capsaicin receptor-related polypeptides, as well as the capsaicin receptor and capsaicin receptor-related polypeptides encoded by such polynucleotides.

A capsaicin receptor polypeptide-encoding polynucleotide was first isolated by virtue of the capsaicin receptor polypeptide-encoding sequence to facilitate expression of a functional capsaicin receptor in a cellular assay. In short, the capsaicin receptor polypeptide-encoding polynucleotide, when expressed in a mammalian or amphibian host cell, facilitated an increase in intracellular calcium concentration in the host cell upon exposure to the agonist capsaicin. This work lead to identification and isolation of a polynucleotide sequence encoding a capsaicin receptor referred to herein as a vanilloid receptor subtype 1 (VR1). The capsaicin receptor-encoding VR1 sequence was then used to isolate by PCR amplification a sequences encoding related polypeptides, resulting in isolation and identification of sequences encoding a capsaicin receptor-related polypeptide, of which VRRP-1 (VR2) is exemplary.

The invention also encompasses use of capsaicin receptor and capsaicin receptor-related polypeptide nucleic acid and amino acid sequences in the identification of capsaicin receptor-binding compounds, particularly capsaicin receptor-binding compounds having capsaicin receptor agonist or antagonist activity. The invention further encompasses the use of the polynucleotides disclosed herein to facilitate identification and isolation of polynucleotide and polypeptide sequences having homology to a capsaicin receptor and/or capsaicin receptor-related polypeptide of the invention; as well as the diagnosis, prevention and treatment of disease and/or pain syndromes associated with capsaicin receptor biological activity.

The polynucleotides of the invention can also be used as a molecular probe with which to determine the structure, location, and expression of capsaicin receptor, receptor subtypes, and capsaicin receptor-related polypeptides in mammals (including humans) and to investigate potential associations between disease states or clinical disorders (particularly those involving acute and chronic pain or inflammation) and defects or alterations in receptor structure, expression, or function.

Capsaicin Receptor and Capsaicin Receptor-Related Polypeptide Coding Sequences

In accordance with the invention, any nucleic acid sequence that encodes an amino acid sequence of a capsaicin receptor polypeptide or capsaicin receptor-related polypeptide can be used to generate recombinant molecules which express a capsaicin receptor polypeptide or capsaicin receptor-related polypeptide, respectively. The nucleic acid compositions used in the subject invention may encode all or a part of a capsaicin receptor polypeptide or capsaicin receptor-related polypeptide of the invention as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide.

The nucleic acid and deduced amino acid sequences of rat capsaicin receptor (subtype VR1) are provided as SEQ ID NOS:1 and 2. Nucleic acid and deduced amino acid sequences of a human capsaicin receptor (subtype VR1) are provided as SEQ ID NOS:33 and 34. A nucleotide sequence encoding murine capsaicin receptor subtype VR1 comprises the sequences of SEQ ID NOS:10 and 11. The chicken capsaicin receptor subtype VR1 is provided as SEQ ID NO:24 and 25.

The nucleic acid and deduced amino acid sequence of rat capsaicin receptor-related polypeptide 1 (VRRP-1; or subtype VR2) are provided as SEQ ID NO:3 and 4, respectively. A sequence encoding a human capsaicin receptor-related polypeptide (referred to as human VR2) comprises the nucleotide sequence SEQ ID NOS:35 and 36.

The present invention also encompasses variants of capsaicin receptor and capsaicin receptor-related polypeptides. A preferred variant is one having at least 80% amino acid sequence similarity, more preferably at least 90% amino acid sequence similarity, still more preferably at least 95% amino acid sequence similarity to an amino acid sequence of a capsaicin receptor, subtype VR1 or VR2.

It will be appreciated by those skilled in the art that as a result of the degeneracy of the genetic code, a multitude of degenerate variants of nucleotide sequences encoding capsaicin receptor and capsaicin receptor-related polypeptides, some bearing minimal homology to the nucleotide sequences of any known and naturally occurring gene, can be produced. The invention contemplates each and every possible variation of nucleotide sequence that can be made by selecting combinations based on possible codon choices. These combinations are made in accordance with the standard triplet genetic code as applied to the nucleotide sequence of naturally occurring capsaicin receptor or capsaicin receptor-related polypeptide, and all such variations are to be considered as being specifically disclosed herein.

Although nucleotide sequences that encode capsaicin receptor polypeptides, and their variants are preferably capable of hybridizing to the nucleotide sequence of the naturally occurring polypeptides under appropriately selected conditions of stringency, it may be advantageous to produce nucleotide sequences encoding receptors or their derivatives possessing a substantially different codon usage. Codons can be selected to increase the rate at which expression of the polypeptide occurs in a particular prokaryotic or eukaryotic expression host in accordance with the frequency with which particular codons are utilized by the host. Other reasons for substantially altering the nucleotide sequence encoding capsaicin receptor, capsaicin receptor-related polypeptide, and their derivatives without altering the encoded amino acid sequences include the production of RNA transcripts having more desirable properties (e.g., increased half-life) than transcripts produced from the naturally occurring sequence.

Nucleotide sequences encoding a capsaicin receptor polypeptide, capsaicin receptor-related polypeptide, and/or their derivatives can be synthesized entirely by synthetic chemistry, after which the synthetic gene can be inserted into any of the many available DNA vectors and expression systems using reagents that are well known in the art at the time of the filing of this application. Moreover, synthetic chemistry can be used to introduce mutations into a sequence encoding a capsaicin receptor polypeptide or capsaicin receptor-related polypeptide.

Also included within the scope of the present invention are polynucleotide sequences that are capable of hybridizing to the nucleotide sequence of any of the provided nucleic acid sequences of capsaicin receptors, subtypes VR1 or VR2. Of particular interest are polynucleotide sequence capable of hybridizing under various conditions of stringency to the coding sequence for capsaicin receptor or capsaicin receptor-related polypeptide (e.g., nucleotides 81–2594 of SEQ ID NO:1, or nucleotides 14–2530 of SEQ ID NO:33), to a region of a capsaicin receptor-encoding sequence or capsaicin receptor-related polypeptide-encoding sequence that shares homology with other such sequences (e.g., a sequence encoding a contiguous stretch of amino acid residues present in SEQ ID NO:2 (e.g., amino acid residues 636 to 706 of SEQ ID NO:2), a sequence encoding a contiguous stretch of amino acid residues present in SEQ ID NO:33 (e.g., amino acid residues 636 to 706 of SEQ ID NO:33), and other sequences representing areas of homology with other capsaicin receptor-encoding sequences and/or capsaicin receptor-related polypeptide-encoding sequences, as well as sequences that uniquely identify capsaicin receptor-encoding sequences or capsaicin receptor-related polypeptide-encoding sequences of various species. Of particular interest are capsaicin receptor VR1 or VR2 polynucleotide sequences encoding a human capsaicin receptor polypeptide or human capsaicin receptor-related polypeptide. Hybridization conditions are based on the melting temperature (Tm) of the nucleic acid binding complex or probe, as taught in Berger et al. 1987 Guide to Molecular Cloning Techniques, Methods in Enzymology, Vol 152, Academic Press, San Diego Calif. incorporated herein by reference, and can be used at a defined stringency.

Altered nucleic acid sequences encoding capsaicin receptor or capsaicin receptor-related polypeptide that can be used in accordance with the invention include deletions, insertions or substitutions of different nucleotides resulting in a polynucleotide that encodes the same or a functionally equivalent capsaicin receptor or capsaicin receptor-related polypeptide. The protein can also comprise deletions, insertions or substitutions of amino acid residues that result in a polypeptide that is functionally equivalent to capsaicin receptor or capsaicin receptor-related polypeptide. Deliberate amino acid substitutions can be made on the basis of similarity in polarity, charge, solubility, hydrophobicity, hydrophilicity, and/or the amphipathic nature of the residues with the proviso that biological activity of capsaicin receptor is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Alleles of capsaicin receptor, as well as alleles of capsaicin receptor-related polypeptide, are also encompassed by the present invention. As used herein, an "allele" or "allelic sequence" is an alternative form of a capsaicin receptor or capsaicin receptor-related polypeptide. Alleles result from a mutation (i.e., an alteration in the nucleic acid sequence) and generally produce altered mRNAs and/or polypeptides that may or may not have an altered structure or function relative to naturally-occurring capsaicin receptor or capsaicin receptor-related polypeptide. Any given gene may have none, one, or many allelic forms. Common mutational changes that give rise to alleles are generally ascribed to natural deletions, additions or substitutions of amino acids. Each of these types of changes may occur alone or in combination with the other changes, and may occur once or multiple-times in a given sequence.

Isolating Capsaicin Receptor-Encoding and Capsaicin Receptor-Related Polypeptide-Encoding Polynucleotides from Other Species Capsaicin receptor polypeptide-encoding polynucleotides, capsaicin receptor-related polypeptide-encoding polynucleotides, or portions thereof can be used as probes for identifying and cloning homologs of the capsaicin receptor and capsaicin receptor-related polypeptide sequences disclosed herein. Of particular interest are mammalian homologs (especially the human homology of the disclosed rat capsaicin receptor-encoding and capsaicin receptor-related polypeptide-encoding sequences), where the homologs have substantial sequence similarity to one another, i.e. at least 40%, usually at least 60%, more usually at least 75%, usually at least 90%, more usually at least 95% sequence similarity. Mammalian homologs of capsaicin receptor may also share a high degree of similarity to the capsaicin receptor disclosed herein in the vicinity of the predicted pore-loop and sixth transmembrane domains. At these regions the capsaicin receptor homologs may exhibit high sequence similarity, e.g., at least about 40% amino acid sequence identity, usually at least about 60% to 75% amino acid sequence identity, with at least about 40% nucleotide sequence similarity, usually at least about 60% to 90% nucleotide sequence similarity.

Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) J Mol Biol 215:403–10. The specificity of the probe, whether it is made from a highly specific region, e.g., 10 unique nucleotides in the 5' regulatory region, or a less specific region, e.g., especially in the 3' region, and the stringency of the hybridization or amplification (maximal, high, intermediate or low) will determine whether the probe identifies only naturally occurring sequences encoding capsaicin receptor, alleles or related sequences.

Where the probes of the invention are used in the detection of related sequences, the probes preferably comprise at least 30%, more preferably at least 50% of the nucleotides from any of the capsaicin receptor polypeptide-encoding sequences or the capsaicin receptor-related polypeptide-encoding described herein. The hybridization probes of the subject invention can be derived from the provided VR1 and VR2 nucleotide sequences, or from their corresponding genomic sequences including promoters, enhancer elements and introns of the naturally occurring capsaicin receptor-encoding sequence. Hybridization probes can be detectably labeled with a variety of reporter molecules, including radionuclides (e.g., $^{32}P$ or $^{35}S$), or enzymatic labels (e.g., alkaline phosphatase coupled to the probe via avidinibiotin coupling systems), and the like.

Specific hybridization probes can also be produced by cloning the provided nucleic acid sequences into vectors for production of mRNA probes. Such vectors, which are known in the art and are commercially available, can be used to synthesize RNA probes in vitro using an appropriate RNA polymerase (e.g., T7 or SP6 RNA polymerase) and appropriate radioactively labeled nucleotides.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast Drosophila, Caenhorabditis, etc. Of particular interest is the identification and isolation of human capsaicin receptor polypeptide-encoding polynucleotides and human capsaicin receptor-related polypeptide-encoding polynucleotides.

The capsaicin receptor and capsaicin receptor-related polypeptide nucleic acid sequences can also be used to generate hybridization probes for mapping a naturally occurring genomic sequence. The sequence can be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price 1993; Blood Rev 7:127–34 and Trask 1991; Trends Genet 7:149–54. Fluorescent in situ hybridization of chromosome spreads is described in, for example, Verma et al 1988 Human Chromosomes: A Manual of Basic Techniques, Pergamon Press, New York N.Y.

Information from chromosomal mapping of sequences encoding capsaicin receptor or capsaicin receptor-related polypeptide can be correlated with additional genetic map data. Correlation between the location of a capsaicin receptor-encoding sequence, or a capsaicin receptor-related polypeptide-encoding sequence, on a physical chromosomal map and a specific disease (or predisposition to a specific disease) can help delimit the region of DNA associated with that genetic disease. The nucleotide sequences of the subject invention can be used to detect differences in gene sequences (e.g., differences in the chromosomal location due to translocation, inversion, etc. or other differences in the capsaicin receptor-encoding region due to insertional mutation(s) or deletion of capsaicin receptor- or capsaicin receptor-related polypeptide-encoding sequences) between normal, carrier, or affected individuals. Exemplary disorders that may benefit from such information include, but are not necessarily limited to, complex regional pain syndromes, reflex sympathetic dystrophies, postherpetic neuralgia, psoriasis, reactive airway diseases (e.g., asthma, chronic obstructive pulmonary disease), osteoarthritis, rheumatoid arthritis, diabetic neuropathy, AIDS-associated neuropathies, and hereditary neuropathies (e.g., associated with capsaicin receptor dysfunction).

Extending the Capsaicin Receptor-Encoding Polynucleotide Sequence

The polynucleotide sequence encoding capsaicin receptor or capsaicin receptor-related polypeptide can be extended utilizing partial nucleotide sequence and various methods known in the art to detect upstream sequences such as promoters and regulatory elements. Gobinda et al 1993; PCR Methods Applic 2:318–22 disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia et al 1988 Nucleic Acids Res 16:8186). The primers can be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68–72° C. This method uses several restriction enzymes to generate a suitable fragment in the known region of a gene. The fragment is then circularized by intramolecular ligation and used as a PCR template.

Capture PCR (Lagerstrom et al 1991 PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method that can be used to retrieve unknown sequences is that of Parker et al 1991; Nucleic Acids Res 19:3055–60. Additionally, one can use PCR, nested primers, and PromoterFinder libraries to "walk in" genomic DNA (PromoterFinder™ Clontech (Palo Alto Calif.). This process avoids the need to screen libraries and is useful in finding intron/exon junctions. Preferably, the libraries used to identify full length cDNAs have been size-selected to include larger cDNAs. More preferably, the cDNA libraries used to identify full-length cDNAs are those generated using random primers, in that such libraries will contain more sequences comprising regions 5' of the sequence(s) of interest A randomly primed library can be particularly useful where oligo d(T) libraries do not yield a full-length cDNA. Genomic libraries are preferred for identification and isolation of 5' nontranslated regulatory regions of a sequence(s) of interest.

Capillary electrophoresis can be used to analyze the size of, or confirm the nucleotide sequence of, sequencing or PCR products. Systems for rapid sequencing are available from Perkin Elmer, Beckman Instruments (Fullerton Calif.), and other companies. Capillary sequencing can employ flowable polymers for electrophoretic separation, four different, laser-activatable fluorescent dyes (one for each nucleotide), and a charge coupled device camera for detection of the wavelengths emitted by the fluorescent dyes. Output/light intensity is converted to electrical signal using appropriate software (e.g. Genotyper™ and Sequence Navigator™ from Perkin Elmer). The entire process from loading of the samples to computer analysis and electronic data display is computer controlled. Capillary electrophoresis is particularly suited to the sequencing of small pieces of DNA that might be present in limited amounts in a particular sample. Capillary electrophoresis provides reproducible sequencing of up to 350 bp of M13 phage DNA in 30 min (Ruiz-Martinez et al 1993 Anal Chem 65:2851–2858).

Production of Polynucleotides Encoding Capsaicin Receptor or Capsaicin Receptor-Related Polypeptides In accordance with the present invention, polynucleotide sequences that encode capsaicin receptor polypeptides or capsaicin receptor-related polypeptides (which capsaicin receptor polypeptides and capsaicin receptor-related polypeptides include fragments of the naturally-occurring polypeptide, fusion proteins, and functional equivalents thereof) can be used in recombinant DNA molecules that direct the expression of capsaicin receptor or capsaicin receptor-related polypeptides in appropriate host cells. Due to the inherent degeneracy of the genetic code, other DNA sequences that encode substantially the same or a functionally equivalent amino acid sequence, can be used to clone and express capsaicin receptor or capsaicin receptor-related polypeptide. As will be understood by those of skill in the art, it may be advantageous to produce capsaicin receptor-encoding nucleotide sequences and capsaicin receptor-related polypeptide-encoding nucleotide sequences possessing non-naturally occurring codons. Codons preferred by a particular prokaryotic or eukaryotic host (Murray et al 1989 Nuc Acids Res 17:477–508) can be selected, for example, to increase the rate of expression or to produce recombinant RNA transcripts having a desirable characteristic(s) (e.g., longer half-life than transcripts produced from naturally occurring sequence).

The nucleotide sequences of the present invention can be engineered in order to alter an capsaicin receptor-encoding sequence or a capsaicin receptor-related polypeptide-encoding sequence for a variety of reasons, including but not limited to, alterations that facilitate the cloning, processing and/or expression of the gene product. For example, mutations can be introduced using techniques that are well known in the art, e.g., site-directed mutagenesis to insert new restriction sites, alter glycosylation patterns, change codon preference, produce splice variants, etc.

In another embodiment of the invention, a natural, modified, or recombinant polynucleotide encoding a capsaicin receptor polypeptide or capsaicin receptor-related polypeptide can be ligated to a heterologous sequence to encode a fusion protein. Such fusion proteins can also be engineered to contain a cleavage site located between a capsaicin receptor polypeptide-encoding sequence (or capsaicin receptor-related polypeptide-encoding sequence) and a heterologous polypeptide sequence, such that the heterologous polypeptide sequence can be cleaved and purified away from the capsaicin receptor polypeptide or capsaicin receptor-related polypeptide.

In an alternative embodiment of the invention, a nucleotide sequence encoding a capsaicin receptor polypeptide or capsaicin receptor-related polypeptide can be synthesized, in whole or in part, using chemical methods well known in the art (see, e.g., Caruthers et al 1980 Nuc Acids Res Symp Ser 215–23, Horn et al (1980) Nuc Acids Res Symp Ser 225–32). Alternatively, the polypeptide itself can be produced using chemical methods to synthesize an amino acid sequence of a capsaicin receptor or capsaicin receptor-related polypeptide, in whole or in part. For example, peptide synthesis can be performed using various solid-phase techniques (Roberge et al 1995 Science 269:202–204) and automated synthesis can be achieved, for example, using the ABI 431A Peptide Synthesizer (Perkin Elmer) in accordance with the instructions provided by the manufacturer.

The newly synthesized polypeptide can be substantially purified by preparative high performance liquid chromatography (e.g. Creighton 1983 Proteins, Structures and Molecular Principles, W H Freeman and Co, New York N.Y.). The composition of the synthetic polypeptides can be confirmed by amino acid analysis or sequencing (e.g., the Edman degradation procedure; Creighton, supra). Additionally the amino acid sequence of capsaicin receptor, capsaicin receptor-related polypeptide, or any part thereof, can be altered during direct synthesis and/or combined using chemical methods with sequences from other proteins, or any part thereof, to produce a variant polypeptide.

Capsaicin Receptor and Capsaicin Receptor-Related Polypeptide Expression Systems The invention encompasses expression of capsaicin receptor polypeptides and capsaicin receptor-related polypeptides individually or in combination (e.g., co-expression). In order to express a biologically active capsaicin receptor polypeptide and/or capsaicin receptor-related polypeptide, the nucleotide sequence encoding a capsaicin receptor polypeptide, a capsaicin receptor-related polypeptide, and/or a functional equivalent of either, is inserted into an appropriate expression vector, i.e., a vector having the necessary elements for the transcription and translation of the inserted coding sequence. Methods well known to those skilled in the art can be used to construct expression vectors comprising a desired polypeptide-encoding sequence and appropriate transcriptional or translational controls. These methods include in vitro recombinant DNA techniques, synthetic techniques and in vivo recombination or genetic recombination. Such techniques are described in Sambrook et al 1989 Molecular Cloning, A Laboratory Manual, Cold Spring Harbor Press, Plainview N.Y. and Ausubel et al 1989 Current Protocols in Molecular Biology, John Wiley & Sons, New York N.Y.

A variety of expression vector/host cell systems can be utilized to express a capsaicin receptor polypeptide- and capsaicin receptor-related polypeptide-encoding sequence. These include, but are not limited to, amphibian oocytes (e.g., Xenopus oocytes); microorganisms such as bacteria transformed with recombinant bacteriophage, plasmid or cosmid DNA expression vectors; yeast transformed with yeast expression vectors; insect cell systems infected with viral expression vectors (e.g., baculovirus); plant cell systems transfected with viral expression vectors (e.g., cauliflower mosaic virus, CaMV; tobacco mosaic virus, TMV) or transformed with bacterial expression vectors (e.g., Ti or pBR322 plasmid); or animal (e.g., mammalian) cell systems. Preferably, the sequences of the present invention, particularly capsaicin receptor-encoding sequences, are expressed in a mammalian cell system (e.g., human embryonic kidney cells (e.g., HEK 293), an amphibian oocyte (e.g., by injecting Xenopus oocytes with complementary capsaicin receptor-encoding RNA), or other host cell that is easily propagated in culture and can be transformed or transfected to either transiently or stably express, preferably stably express, a capsaicin receptor-encoding sequence and/or capsaicin receptor-related polypeptide-encoding sequence).

Host cells can be selected for capsaicin receptor polypeptide and/or capsaicin receptor-related polypeptide expression according to the ability of the cell to modulate the expression of the inserted sequences or to process the expressed protein in a desired fashion. Such modifications of the polypeptide include, but are not limited to, acetylation, carboxylation, glycosylation, phosphorylation, lipidation and acylation. Post-translational processing that involves cleavage of a "prepro" form of the protein may also be important for correct polypeptide folding, membrane insertion, and/or function. Host cells such as HEK 293, CHO, HeLa, MDCK, WI38, Xenopus oocytes, and others have specific cellular machinery and characteristic mechanisms for such post-translational activities and may be chosen to ensure the correct modification and processing of the introduced, foreign polypeptide.

The vector(s) used for expression of a capsaicin receptor polypeptide and/or capsaicin receptor-related polypeptide will vary with a variety of factors including the host cell in which the capsaicin receptor polypeptide is to be expressed, whether capsaicin receptor polypeptide- and capsaicin receptor-related polypeptide sequences are to be co-expressed either from a single construct or from separate constructs, and the intended use for the polypeptide produced. For example, when large quantities of a capsaicin receptor polypeptide or capsaicin receptor-related polypeptide are required (e.g., for the antibody production), vectors that direct high-level expression of fusion proteins that can be readily purified may be desirable. Such vectors include, for example, bacterial expression vectors, including multi-functional *E. coli* cloning and expression vectors such as Bluescript® (Stratagene; which provides for production of polypeptide-β-galactosidase hybrid proteins); and pGEX vectors (Promega, Madison Wis.; which provides for production of glutathione S-transferase (GST) fusion proteins. Where the host cell is yeast (e.g., *Saccharomyces cerevisiae*) a number of vectors containing constitutive or inducible promoters such as alpha factor, alcohol oxidase and PGH can be used. For reviews, see Ausubel et al (supra) and Grant et al 1987 Methods in Enzymology 153:516–544.

Where the host cell is a mammalian cells, a number of expression systems can be used. For example, the expression vector can be derived from a viral-based expression system, such as an expression system derived from an adenovirus, SV40, CMV, or RSV nucleotide sequence. Expression efficiency can be enhanced by including enhancers appropriate to the cell system in use (Scharf et al 1994 Results Probl Cell Differ 20:125–62; Bittner et al 1987 Methods in Enzymol 153:516–544) (e.g., the RSV enhancer can be used to increase expression in mammalian host cells).

The "control elements" or "regulatory sequences" of these systems, which vary in their strength and specificities, are those nontranslated regions of the vector, enhancers, promoters, and 3' untranslated regions that interact with host cellular proteins to facilitate transcription and translation of a nucleotide sequence of interest. Depending on the vector system and host utilized, any number of suitable transcriptional and translational elements, including constitutive and inducible promoters, can be used. Such control elements or regulatory sequences are selected according to the host cell in which the capsaicin receptor-encoding polynucleotide and/or capsaicin receptor-related polypeptide-encoding polynucleotide is to be expressed. For example, in mammalian cell systems, promoters from the mammalian genes or from mammalian viruses are most appropriate. Where it is desirable to generate a cell line containing multiple copies of a capsaicin receptor polypeptide-encoding sequence or a capsaicin receptor-related polypeptide-encoding sequence, vectors derived from SV40 or EBV can be used in conjunction with other optional vector elements, e.g., an appropriate selectable marker.

Specific initiation signals may also be required for efficient translation of a capsaicin receptor polypeptide or capsaicin receptor-related polypeptide-encoding sequence, e.g., the ATG initiation codon and flanking sequences for bacterial expression. Where a native sequence, including its initiation codon and upstream sequences, is inserted into the appropriate expression vector, no additional translational control signals may be needed. However, where only coding sequence, or a portion thereof, is inserted in an expression vector, exogenous transcriptional control signals including the ATG initiation codon must be provided. Furthermore, the initiation codon must be in the correct reading frame to ensure transcription of the entire insert. Exogenous transcriptional elements and initiation codons can be derived from various origins, and can be either natural or synthetic.

Where long-term, high-yield recombinant polypeptide production is desired, stable expression is preferred. For example, cell lines that stably express capsaicin receptor and/or capsaicin receptor-related polypeptide can be transformed using expression vectors containing viral origins of replication or endogenous expression elements and a selectable marker gene. After introduction of the vector, cells can be grown in an enriched media before they are exposed to selective media. The selectable marker, which confers resistance to the selective media, allows growth and recovery of cells that successfully express the introduced sequences. Resistant, stably transformed cells can be proliferated using tissue culture techniques appropriate to the host cell type.

Any number of selection systems can be used to recover transformed cell lines. These include, but are not limited to, the herpes simplex virus thymidine kinase (Wigler et al 1977 Cell 11:223–32) and adenine phosphoribosyltransferase (Lowy et al 1980 Cell 22:817–23) genes which can be employed in tk- or aprt-cells, respectively. Also, antimetabolite or antibiotic resistance can be used as the basis for selection; for example, dhfr which confers resistance to methotrexate (Wigler et al 1980 Proc Natl Acad Sci 77:3567–70); and npt, which confers resistance to the aminoglycosides neomycin and G418 (Colbere-Garapin et al 1981 J Mol Biol 150:1–14). Additional selectable genes have been described, for example, trpB, which allows cells to utilize indole in place of tryptophan, or hisD, which allows cells to utilize histinol in place of histidine (Hartman et al. 1988 Proc Natl Acad Sci 85:8047–51). Selectable markers also include visible markers such as anthocyanins, β-glucuronidase and its substrate, GUS, and luciferase and its substrate, luciferin. Such visible markers are useful to both identify transformants and to quantify the amount of transient or stable protein expression attributable to a specific vector system (Rhodes et al 1995 Methods Mol Biol 55:121–131).

Alternatively, host cells that contain the coding sequence for and express capsaicin receptor polypeptides and/or capsaicin receptor-related polypeptides can be identified by a variety of procedures known to those of skill in the art. These procedures include, but are not limited to, DNA-DNA or DNA-RNA hybridization and protein bioassay or immunoassay techniques for the detection and/or quantitation of the nucleic acid or protein.

The presence of polynucleotide sequences encoding a capsaicin receptor and/or capsaicin receptor-related polypeptide can be detected by DNA-DNA or DNA-RNA hybridization or PCR amplification using probes, portions or fragments of polynucleotides encoding capsaicin receptor and/or capsaicin receptor-related polypeptide. Nucleic acid amplification-based assays involve the use of oligonucleotides or oligomers based on a sequence encoding a capsaicin receptor or capsaicin receptor-related polypeptide to detect transformants containing the desired DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of immunoassays for detecting and measuring the expression of a specific protein, using either protein-specific polyclonal or monoclonal antibodies are known in the art. Examples include enzyme-linked immunosorbent assay (ELISA), radioimmunoassay (RIA) and fluorescent activated cell sorting (FACS). These and other assays are described in, e.g., Hampton et al 1990, Serological Methods, A Laboratory Manual, APS Press, St Paul Minn. and Maddox et al 1983, J Exp Med 158:1211.

A wide variety of detectable labels and conjugation techniques are known the art and can be used in various nucleic acid and amino acid assays. Means for producing labeled hybridization or PCR probes for detecting sequences related to sequences encoding a capsaicin receptor or capsaicin receptor-related polypeptide include oligolabeling, nick translation, end-labeling or PCR amplification using a labeled nucleotide. Alternatively, a nucleotide sequence encoding a capsaicin receptor polypeptide or capsaicin receptor-related polypeptide can be cloned into a vector for the production of an mRNA probe. Vectors and methods for production of mRNA probes are well known in the art. Suitable reporter molecules or labels include those radionuclides, enzymes, fluorescent, chemiluminescent, or chromogenic agents as well as substrates, cofactors, inhibitors, magnetic particles and the like, as described in U.S. Pat. Nos. 3,817,837; 3,850,752; 3,939,350; 3,996,345; 4,277,437; 4,275,149 and 4,366,241, each of which are incorporated herein by reference.

In a preferred embodiment, host cells expressing capsaicin receptor are screened and selected using a functional assay for capsaicin receptor activity. For example, host cells expressing functional capsaicin receptor can be screened for alterations in intracellular calcium concentrations upon exposure to a capsaicin receptor binding compound (e.g., capsaicin or resiniferatoxin). Where the capsaicin receptor binding compound is a capsaicin receptor agonist, binding of the agonist compound to the capsaicin receptor result in increased levels of intracellular calcium in the host cell expressing capsaicin receptor-encoding nucleic acid. Methods and compositions (e.g.,. fura-2) for monitoring intracellular calcium concentration are well known in the art.

Purification of Capsaicin Receptor Polypeptides and Capsaicin Receptor-Related Polypeptides Methods for production of a polypeptide after identification of its encoding polynucleotide are well known in the art. Host cells transformed with a nucleotide sequence(s) encoding a capsaicin receptor polypeptide and/or capsaicin receptor-related polypeptide can be cultured under conditions suitable for the expression and recovery of the encoded polypeptide from cell culture. The polypeptide produced by a recombinant cell may be secreted or retained intracellularly depending on the sequence and/or the vector used. As will be understood by those of skill in the art, expression vectors containing polynucleotides encoding capsaicin receptor polypeptides or capsaicin receptor-related polypeptides can be designed with signal sequences that direct secretion of the encoded polypeptide(s) through a prokaryotic or eukaryotic cell membrane.

Purification of capsaicin receptor polypeptides and capsaicin receptor-related polypeptides can be facilitated by using a recombinant construct that includes a nucleotide sequence(s) encoding one or more polypeptide domains that, when expressed in-frame with the sequence encoding the capsaicin receptor or capsaicin receptor-related polypeptide, provides a fusion protein having a purification-facilitating domain (Kroll et al 1993 DNA Cell Biol 12:441–53). A cleavable linker sequences(s) between the purification domain and the capsaicin receptor polypeptide- or capsaicin receptor-related polypeptide-encoding sequence can be included to further facilitate purification.

Capsaicin receptor polypeptides and capsaicin receptor-related polypeptides (each of which polypeptides encompass polypeptides having a portion of the native amino acid sequence) can also be produced by direct peptide synthesis using solid-phase techniques (see, e.g., Stewart et al 1969 Solid-Phase Peptide Synthesis, WH Freeman Co, San Francisco; Merrifield 1963 J Am Chem Soc 85:2149–2154). Various fragments of capsaicin receptor or capsaicin receptor-related polypeptide can be chemically synthesized separately and combined using chemical methods to produce the full length molecule.

Methods for purifying a desired polypeptide following either artificial synthesis or recombinant production are routine and well known in the art.

Uses of Capsaicin Receptor Polypeptides, Capsaicin Receptor-Related Polypeptides, and Nucleic Acid Encoding Capsaicin Receptor Polypeptides or Capsaicin Receptor-Related Polypeptides In addition to the uses described above, the nucleotide and polypeptide sequences disclosed herein can be used in a variety of ways, including production of antibodies, identification of capsaicin receptor-binding compounds and capsaicin receptor-related polypeptide-binding compounds that affect capsaicin receptor function (e.g., in a drug screening assay), and in the identification of other polynucleotide sequences encoding capsaicin receptor polypeptides and capsaicin receptor-related polypeptides. In addition, sequences encoding capsaicin receptor polypeptides and capsaicin receptor-related polypeptides can be used in diagnostic assays (e.g., prenatal or postnatal diagnosis). Furthermore, capsaicin receptor-encoding sequences and their encoded polypeptides can also be used in assays to assess the capsaicin content of a sample (e.g., from a natural product, e.g., a chili pepper extract) or the capsaicin-promoting effects of an agent (e.g., a candidate agent for use a flavor enhancing additive to foods).

These and other applications of the sequences of the invention are described in more detail below.

Screening for Capsaicin Receptor- and Capsaicin Receptor-Related Polypeptide Binding Compounds Capsaicin receptor polypeptides and capsaicin receptor-related polypeptides, each of which encompasses biologically active or immunogenic fragments or oligopeptides thereof, can be used for screening compounds that affect capsaicin receptor activity by, for example, specifically binding capsaicin receptor and affecting its function or specifically binding capsaicin receptor-related polypeptide and affecting its interaction with capsaicin receptor, thereby affecting capsaicin receptor activity. Identification of such compounds can be accomplished using any of a variety of drug screening techniques. Of particular interest is the identification of agents that have activity in affecting capsaicin receptor function. Such agents are candidates for development of treatments for, inflammatory conditions associated at least in part with capsaicin receptor activity (e.g., psoriasis, reactive airway diseases (e.g., asthma, chronic obstructive pulmonary disease)), arthritis (e.g., osteoarthritis, rheumatoid arthritis), and for use as analgesics. Of particular interest are screening assays for agents that have a low toxicity for human cells. The polypeptide employed in such a test can be free in solution, affixed to a solid support, present on a cell surface, or located intracellularly. The screening assays of the invention are generally based upon the ability of the agent to bind to a capsaicin receptor polypeptide, bind to a capsaicin receptor-related polypeptide, and/or elicit or inhibit a capsaicin receptor-associated or capsaicin receptor-related polypeptide-associated biological activity (i.e., a functional assay or an assay using radioligand binding assays).

The term "agent" as used herein describes any molecule, e.g. protein or pharmaceutical, with the capability of altering (i.e., eliciting or inhibiting) or mimicking a desired physiological function of capsaicin receptor or capsaicin receptor-related polypeptide. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts (including extracts from human tissue to identify endogenous factors affecting capsaicin receptor or capsaicin receptor-related polypeptide activity) are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Preferably, the drug screening technique used provides for high throughput screening of compounds having suitable binding affinity to the capsaicin receptor, capsaicin receptor-related polypeptide, and/or eliciting a desired capsaicin receptor-associated or capsaicin receptor-related polypeptide-associated response. For example, large numbers of different small peptide test compounds can be synthesized on a solid substrate, such as plastic pins or some other surface (see, e.g., Geysen WO Application 84/03564, published on Sep. 13, 1984), the peptide test compounds contacted with capsaicin receptor polypeptides (or capsaicin receptor-related polypeptides), unreacted materials washed away, and bound capsaicin receptor (or bound capsaicin receptor-related polypeptide) detected by virtue of a detectable label or detection of a biological activity associated with capsaicin receptor activity (or capsaicin receptor-related polypeptide activity). Purified capsaicin receptor or purified capsaicin receptor-related polypeptide can also be coated directly onto plates for use in such in vitro drug screening techniques. Alternatively, non-neutralizing antibodies can be used to capture the polypeptide and immobilize it on a solid support.

The invention also contemplates the use of competitive drug screening assays in which capsaicin receptor-specific neutralizing antibodies or capsaicin receptor-related polypeptide-specific neutralizing antibodies compete with a test compound for binding of capsaicin receptor polypeptide or capsaicin receptor-related polypeptide. In this manner, the antibodies can be used to detect the presence of any polypeptide that shares one or more antigenic determinants with a capsaicin receptor polypeptide or capsaicin receptor-related polypeptide.

Screening of Candidate Agents

A wide variety of assays may be used for identification of capsaicin receptor polypeptide and/or capsaicin receptor-related polypeptide binding agents, including labeled in vitro binding assays, immunoassays for protein binding, and the like. For example, by providing for the production of large amounts of capsaicin receptor polypeptides or capsaicin receptor-related polypeptides, one can identify ligands or substrates that bind to, modulate or mimic the action of the proteins. The purified protein may also be used for determination of three-dimensional crystal structure, which can be used for modeling intermolecular interactions.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc. that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Functional Capsaicin Receptor and Capsaicin Receptor-Related Polypeptide Screening Assays Preferably, capsaicin receptor-binding compounds are screened for agonistic or antagonist action in a functional assay that monitors a biological activity associated with capsaicin receptor function such as effects upon intracellular levels of cations in a capsaicin receptor-expressing host cell (e g., calcium, magnesium, guanidinium, cobalt, potassium, cesium, sodium, and choline, preferably calcium), ligand-activated conductances, cell death (i.e., receptor-mediated cell death which can be monitored using, e.g., morphological assays, chemical assays, or immunological assays), depolarization of the capsaicin receptor-expressing cells (e.g., using fluorescent voltage-sensitive dyes), second messenger production (e.g., through detection of changes in cyclic GMP levels (see, e.g., Wood et al. 1989 J. Neurochem. 53:1203–1211), which can be detected by radioimmunoassay or ELISA), calcium-induced reporter gene expression (see, e.g., Ginty 1997 Neuron 18:183–186), or other readily assayable biological activity associated with capsaicin receptor activity or inhibition of capsaicin receptor activity. Preferably, the functional assay is based upon detection of a biological activity of capsaicin receptor that can be assayed using high-throughput screening of multiple samples simultaneously, e.g., a functional assay based upon detection of a change in fluorescence which in turn is associated with a change in capsaicin receptor activity. Such functional assays can be used to screen candidate agents for activity as either capsaicin receptor agonists or antagonists.

In a preferred embodiment, capsaicin receptor-expressing cells (preferably recombinant capsaicin receptor-expressing cells) are pre-loaded with fluorescently-labeled calcium (e.g., fura-2). The capsaicin receptor-expressing cells are then exposed to a candidate capsaicin receptor-binding compound and the effect of exposure to the compound monitored. Candidate compounds that have capsaicin receptor agonist activity are those that, when contacted with the capsaicin receptor-expressing cells, elicit a capsaicin receptor-mediated increase in intracellular calcium relative to control cells (e.g., capsaicin receptor-expressing cells in the absence of the candidate compound, host cells without capsaicin receptor-encoding nucleic acid, capsaicin receptor-expressing cells exposed to a known capsaicin receptor agonist). Similarly, functional capsaicin receptor assays can be used to identify candidate compounds that block activity of a known capsaicin receptor agonist (e.g., block the activity of or compete with capsaicin or resiniferatoxin), block activity of a known capsaicin receptor antagonist (e.g., block the activity of or compete with capsazepine), and/or have activity as capsaicin receptor antagonists.

In another embodiment, the invention includes a method for identifying compounds that bind capsaicin receptor-related polypeptide, thereby eliciting an agonistic or antagonistic effect on capsaicin receptor-associated function as detected by e.g., intracellular levels of cations in the host cell. To this end, the functional assay involves contacting host cells expressing a capsaicin receptor alone (e.g., VR1) and with host cell co-expressing a capsaicin receptor and a capsaicin receptor-related polypeptide (e.g., VR1 and VRRP-1). Compounds that affect capsaicin receptor activity by affecting function of a capsaicin receptor-related polypeptide are those that affect a capsaicin receptor-associated activity in cells that co-express capsaicin receptor and capsaicin receptor-related polypeptide, but do not significantly affect capsaicin receptor-associated activity in host cells that express capsaicin receptor alone. For example, compounds that elicit a capsaicin receptor-mediated increase in intracellular calcium in cells co-expressing capsaicin receptor and capsaicin receptor-related polypeptide, but not in cells expressing capsaicin receptor alone, are identified as compounds that elicit capsaicin receptor agonist activity via interaction with a capsaicin receptor-related polypeptide.

Pharmaceutical Compositions and Other Compositions Comprising Agents Affecting Capsaicin Receptor Activity Identified by the Screening Assay of the Invention Capsaicin receptor-binding compounds and capsaicin receptor-related polypeptide-binding compounds are useful in eliciting or inhibiting capsaicin receptor-mediated physiological responses, and can be particularly useful in a pharmaceutical composition for ameliorating symptoms associated with chronic pain, inflammation, and other physiological responses associated with capsaicin receptor-mediated activity.

The compounds having the desired pharmacological activity may be administered in a physiologically acceptable carrier to a host for treatment of a condition attributable to capsaicin receptor activity. Alternatively, the identified compounds may be used to enhance, regulate, or otherwise manipulate capsaicin receptor function. The therapeutic agents may be administered in a variety of ways, topically, subcutaneously, intraperitoneally, intravascularly, orally, intrathecally, epidermally, intravesicularly (e.g., as in bladder irrigation to treat neurogenic bladder syndromes), parenterally, etc. Inhaled treatments are of particular interest for the treatment of capsaicin receptor-associated inflammation associated with such conditions as asthma.

Depending upon the manner of introduction, the compounds may be formulated in a variety of ways. The concentration of therapeutically active compound in the formulation may vary from about 0.1–100 wt %. The pharmaceutical compositions can be prepared in various forms, such as granules, tablets, pills, capsules, suspensions, salves, lotions and the like. Pharmaceutical grade organic or inorganic carriers and/or diluents suitable for the selected route of administration can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

In addition, compositions comprising agents affecting capsaicin receptor activity (e.g., by binding capsaicin receptor or by binding a capsaicin receptor-related polypeptide) are useful in other applications, including use in defensive sprays (e.g., "pepper sprays") or as antidotes for such sprays. The screening methods of the invention can be used in a variety of ways to this end, including, for example, identification of drugs that have capsaicin-like activity, but lack or are substantially diminished in one or more of the undesirable side effects associated with capsaicin. For example, while capsaicin is effective in spray deterrents, exposure to capsaicin can be lethal. The screening method of the invention can thus be used to identify compounds that have the desired deterrent effect, but would not likely cause death upon exposure to amounts normally used in defensive sprays. Moreover, the screening method of the invention could be used to identify compounds that differentially affect capsaicin receptors of different mammalian species, thus enabling identification and design of capsaicin receptor agonists and antagonists that substantially affect capsaicin receptors with genus- or species-specificity. Thus, for example, the method of the invention can allow for identification of capsaicin receptor agonists for canine or bear capsaicin receptors, but that do not substantially stimulate human capsaicin receptors. This could be accomplished by screening for compounds that elicit a capsaicin receptor-associated biological activity in host cells expressing a canine capsaicin receptor, but relatively little or no biological activity in host cells expressing human capsaicin receptor.

Therapeutically Effective Dosages

The determination of an effective dose is well within the capability of those skilled in the art. For any compound, the therapeutically effective dose can be estimated initially either in cell culture assays, e.g., using host cells expressing recombinant capsaicin receptor, or in animal models, usually rats, mice, rabbits, dogs, or pigs. The animal model is also used to achieve a desirable concentration range and route of administration. Such information can then be used to determine useful doses and routes for administration in humans. A therapeutically effective dose refers to that amount of an agent (e.g., a compound having activity as capsaicin receptor agonist or antagonist), polypeptide, or anti-polypeptide antibody, that provide the desired physiological effect (e.g., to ameliorate symptoms associated with capsaicin receptor-mediated inflammation or pain, or provide loss of temperature sensation).

Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and expressed as the ratio LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The actual dosage can vary within this range depending upon, for example, the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, location of the site to be treated; age, weight and gender of the patient; diet, time and frequency of administration; drug combination(s); reaction sensitivities; and tolerance/response to therapy. Long-acting pharmaceutical compositions can be administered every 3 to 4 days, every week, or once every two weeks depending on half-life and clearance rate of the particular formulation.

Normal dosage amounts may vary depending upon the route of administration. Guidance as to particular dosages and methods of delivery is provided in the literature and generally available to practitioners in the art. Use of capsaicin and capsaicin analogues in clinical applications and their methods of administration (e.g., formulations, dosages, routes of administration, etc.) are well known in the art (see, e.g., Campbell et at. 1993 "Clinical Applications of Capsaicin and Its Analogues," in Capsaicin in the Study of Pain, pgs. 255–272; U.S. Pat. No. 5,5690,910 (topical anti-inflammatory compositions comprising capsaicin); U.S. Pat. No. 5,296,225 (topical composition comprising capsaicin for treating orofacial pain); U.S. Pat. No. 5,290,816 (topical cream containing resiniferatoxin for desensitization of neurogenic inflammation); U.S. Pat. No. 4,997,853 (topical composition containing capsaicin for treating superficial pain); U.S. Pat. No. 5,403,868 (capsaicin derivatives useful as analgesic and anti-inflammatory agents); U.S. Pat. No. 4,939,149 (administration of resiniferatoxin to cause sensory afferent C-fibre and thermo-regulatory desensitization); U.S. Pat. No. 4,536,404 (topical treatment of post herpetic neuralgia by application of capsaicin), each of which is incorporated by reference in its entirety. Further general guidance on administration of capsaicin receptor agonist and antagonists can be found in, e.g., United States Pharmacopeia (USP), $17^{th}$Ed., pgs. 710–711; and Physician's Desk Reference 1996, Medical Economics Com., Montvale, N.J. (see particularly Dolorac™ at 1054, Zostrix™ at 1056, and Zostrix-HP™ topical analgesic cream at 1056, each of which contain capsaicin); and the latest edition of Remingtons' Pharmaceutical Sciences, Mack Publishing Co., Easton Pa.

Use of Capsaicin Receptor-Encoding Polynucleotides in Assays for Quantitating the Capsaicin Content of a Sample or Determining the Capsaicin Activity of a Candidate Food Additive Capsaicin receptor polypeptide-encoding polynucleotides and capsaicin receptor polypeptides can be used in an assay to determine, either qualitatively or quantitatively, to detect capsaicin or an agent having capsaicin activity, in a sample, where the sample is derived from a food product or contains a candidate agent for use as a flavoring agent (e.g., for use as a spice in food or food products). This assay takes advantage of the fact that, in addition to its analgesic effects upon afferent neurons, capsaicin is a member of the vanilloid family of compounds, which are responsible for making foods "spicy hot." For example, capsaicin is present in peppers (e.g., Thai. green poblano verde, habenero, and guero peppers). Conventional assays for determining the amount of capsaicin in a pepper extract involve tedious extraction of the compound from pepper samples and quantitation by high pressure liquid chromatography (HPLC) (see, e.g., Woodbury 1980 J. Assoc. Off. Anal. Chem. 63:556–558). The amount of capsaicin is then correlated with number of Scoville heat units, a measure of "hotness."

The assay of the invention uses an isolated capsaicin receptor polypeptide to detect the amount of capsaicin in a sample, thus avoiding the chemical extraction technique employed in the conditional assay. The capsaicin receptor polypeptide used may be either bound to a solid support, present in solution, or present on the surface of a recombinant host cell. Binding of capsaicin to the capsaicin receptor polypeptide is detected as described in the screening assays described above.

Preferably, the assay for capsaicin or a compound having capsaicin activity in a sample is performed using a functional assay described above. More preferably, the functional assay uses capsaicin receptor-expressing recombinant eukaryotic cells (preferably mammalian cells or amphibian oocytes) that are preloaded with a calcium-sensitive fluorescent dye (e.g., fura-2, indo-1, fluo-3). The presence and/or amount of capsaicin or capsaicinoid compound in the sample is then determined by measuring a capsaicin receptor-mediated cellular effect, e.g., an alteration in voltage-activated conductances across the cellular membrane or an alteration in the intracellular levels of the detectably labeled cation. For example, where the detectably labeled cation is fluorescently labeled calcium, exposure of the preloaded host cells to a capsaicin-containing sample results in binding of the capsaicin to the capsaicin receptor polypeptide and the capsaicin receptor-mediated increase in intracellular calcium, which can be readily detected and quantitated. For example, the level of intracellular calcium influx mediated by the test sample is compared to the intracellular calcium influx associated with a control sample (e.g., with a sample having a known amount of capsaicin). The extent of the change in current, intracellular calcium concentration, or other capsaicin receptor-mediated phenomenon is then correlated with a concentration of capsaicin, which in turn can be assigned a Scoville heat unit.

Similarly, candidate agents for use as food additives to make a food or food product "hot" can be screened for their ability to elicit a capsaicin receptor-mediated cellular response (e.g., change in voltage-activated conductances or intracellular cation concentration). The assay has the advantage that the measure of hotness can be determined objectively, e.g., based upon the responses elicited by exposure to the capsaicin receptor.

Diagnostic Uses of Polynucleotides Encoding Capsaicin Receptor or Capsaicin Receptor-Related PolyPeptides to Detect Capsaicin Receptor-Encoding Sequences Polynucleotide sequences encoding capsaicin receptor polypeptide or capsaicin receptor-related polypeptide can be used in the diagnosis (e.g., prenatal or post-natal diagnosis) of conditions or diseases associated with, for example, capsaicin receptor expression, with a particular capsaicin receptor polymorphism or mutation, and/or with capsaicin receptor-related polypeptide expression. For example, polynucleotide sequences encoding capsaicin receptor or capsaicin receptor-related polypeptide can be used in hybridization or PCR assays of fluids or tissues from biopsies to detect capsaicin receptor or capsaicin receptor-related polypeptide expression, respectively. Suitable qualitative or quantitative methods include Southern or northern analysis, dot blot or other membrane-based technologies; PCR technologies; dip stick, pIN, chip and ELISA technologies. All of these techniques are well known in the art and are the basis of many commercially available diagnostic kits. Once disease is established, a therapeutic agent is administered or other intervention or precautions initiated as appropriate for the capsaicin receptor-associated disorder.

Oligonucleotides based upon capsaicin receptor or capsaicin receptor-related polypeptide sequences can be used in PCR-based techniques for assessing capsaicin receptor-polypeptide expression, detection of capsaicin receptor polymorphisms associated with disorders, and/or capsaicin receptor-related polypeptide expression. Methods for PCR amplification are described in U.S. Pat. Nos. 4,683,196 and 4,965,188. Such oligomers are generally chemically synthesized, or produced enzymatically or by recombinantly. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers can be employed under less stringent conditions for detection and/or quantitation of closely related DNA or RNA sequences.

Additional methods for quantitation of expression of a particular molecule according to the invention include radiolabeling (Melby et al 1993 J Immunol Methods 159:23544) or biotinylating (Duplaa C 1993 Anal Biochem 229–36) nucleotides, coamplification of a control nucleic acid, and interpolation of experimental results according to standard curves. Quantitation of multiple samples can be made more time efficient by running the assay in an ELISA format in which the oligomer of interest is presented in various dilutions and rapid quantitation is accomplished by spectrophotometric or colorimetric detection.

Therapeutic Uses of Capsaicin Receptor Polypeptides and Capsaicin Receptor Polypeptide-Encoding Nucleic Acid Polypeptides of, as well as nucleotide sequence encoding, capsaicin receptor polypeptides and capsaicin receptor-related polypeptides may be useful in the treatment of conditions associated with capsaicin receptor dysfunction (e.g., capsaicin receptor activity that is increased relative to capsaicin receptor activity in an unaffected patient or capsaicin receptor activity that is decreased relative to capsaicin receptor activity in an unaffected patient). In addition, expression of dominant-negative capsaicin receptor-encoding sequences may be therapeutically useful in a condition associated with elevated levels of capsaicin receptor activity. Where interaction of capsaicin receptor and a capsaicin receptor-related polypeptide is associated with a condition, interaction of these polypeptides can be disrupted by, for example, introduction of a peptide corresponding to an interaction domain of capsaicin receptor and capsaicin receptor-related polypeptide. Moreover, expression of a wild-type capsaicin receptor sequence in tumor cells may render such tumor cells more susceptible to capsaicin receptor-mediated cell death.

Expression vectors derived from retroviruses, adenovirus, herpes or vaccinia viruses, or from various bacterial plasmids, can be used for delivery of nucleotide sequences to the targeted organ, tissue or cell population. Preferably the targeted cell for delivery and expression of capsaicin receptor polypeptide-encoding sequences is a neuronal cell, more preferably an afferent neuron in order to enhance capsaicin receptor activity in the neuronal cell. Recombinant vectors for expression of antisense capsaicin receptor polynucleotides can be constructed according to methods well known in the art (see, for example, the techniques described in Sambrook et al (supra) and Ausubel et al (supra)).

Alternatively, expression of genes encoding capsaicin receptor can be decreased by transfecting a cell or tissue with expression vectors that express high levels of a desired capsaicin receptor-encoding fragment. Such constructs can flood cells with untranslatable sense or antisense sequences. Even in the absence of integration into the DNA, such vectors can continue to transcribe RNA molecules until all copies are disabled by endogenous nucleases. Such an approach to regulation of capsaicin receptor expression and activity can be useful in treatment of pain syndromes and/or inflammatory conditions associated with capsaicin receptor activity.

Modifications of gene expression can be obtained by designing antisense molecules, DNA, RNA or PNA, to the control regions of gene encoding capsaicin receptor (i.e., the promoters, enhancers, and introns). Oligonucleotides derived from the transcription initiation site, e.g., between −10 and +10 regions of the leader sequence, are preferred. The antisense molecules can also be designed to block translation of mRNA by preventing the transcript from binding to ribosomes. Similarly, inhibition of expression can be achieved using "triple helix" base-pairing methodology. Triple helix pairing compromises the ability of the double helix to open sufficiently for binding of polymerases, transcription factors, or regulatory molecules. Recent therapeutic advances using triplex DNA were reviewed by Gee J E et al (In: Huber et al. 1994 Molecular and Immunologic Approaches, Futura Publishing Co, Mt Kisco N.Y.). Antisense molecules of the invention can be prepared by methods known in the art for the synthesis of RNA molecules, including techniques for chemical oligonucleotide synthesis, e.g., solid phase phosphoramidite chemical synthesis. Such DNA sequences can be incorporated into a wide variety of vectors with suitable RNA polymerase promoters (e.g., T7 or SP6). Alternatively, antisense cDNA constructs useful in the constitutive or inducible synthesis of antisense RNA can be introduced into cell lines, cells, or tissues.

Particularly where RNA molecules are to be administered for antisense therapy, the RNA can be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine that are not as easily recognized by endogenous endonucleases.

Methods for introducing vectors into cells or tissues include those methods discussed infra and which are equally suitable for in vivo therapy.

In a preferred embodiment, capsaicin receptor polypepide-encoding polynucleotides are introduced in vivo into a target tumor cell for which organochemotherapy is desired. This aspect of the invention takes advantage of the range of capsaicin receptor response to exposure to agonists (e.g., capsaicin, resiniferatoxin) and/or to temperature. For example, low concentrations of capsaicin receptor agonists (e.g. capsaicin receptor agonist concentrations in the nanomolar range, e.g., from about 200 nM to about 800 nM are associated with capsaicin receptor stimulation and intracellular calcium influx. Where the capsaicin receptor is expressed in a neuronal cell, capsaicin receptor stimulation by low concentrations of capsaicin receptor agonist is followed by neuronal desensitization. However, high concentrations of capsaicin receptor agonists (e.g., capsaicin receptor agonist concentrations in the micromolar range, e.g., from about 1 $\mu$M to about 10 $\mu$M mediate neuronal degeneration and cell death. By expressing capsaicin receptor polypeptides in tumor cells, the tumor cell death can be substantially selectively facilitated by local administration of high concentrations of a capsaicin receptor agonist, or by local exposure to heat stimuli, or both, where the agonist concentration and/or heat stimulus is sufficient to mediate cell death in the capsaicin receptor-expressing target tumor cell, but does not substantially affect normal capsaicin receptor-expressing cells or affects a minimal number of such normal cells.

Alternatively, the capsaicin receptor polypeptide introduced into the tumor cells can be engineered to provide more selectivity in the response to organochemotherapy (i.e., to provide for activation of the capsaicin receptor expressed in the tumor cells with no or little activation of endogenous, wild-type capsaicin receptor). For example, capsaicin receptor can be modified so as to bind a specific capsaicin receptor agonist analogue, which analogue is substantially reduced in its ability to bind wildtype capsaicin receptors. Therefore, target cells (e.g., tumor cells) expressing the altered capsaicin receptor can be selectively stimulated by administration of the agonist having specificity for the altered capsaicin receptor polypeptide without substantially affecting cells expressing wildtype capsaicin receptor. Alternatively, the tumor cells can be transformed in vivo with a sequence encoding a modified capsaicin receptor, where the modified capsaicin receptor is more responsive to agonists (e.g., is more responsive to agonist, has increased affinity to agonists relative to wild-type thereby allowing activation of the modified receptors with no or little activation of the endogenous capsaicin receptor, and/or is modified so as to be more responsive to heat stimuli than wild-type capsaicin receptor). These embodiments thus allow administration of high or higher concentrations of the altered capsaicin receptor-targeted organochemotherapeutic, thereby providing for more selective organochemotherapy.

Anti-Capsaicin Receptor and Anti-Capsaicin Receptor-Related Polypeptide Antibodies Capsaicin receptor-specific antibodies and capsaicin receptor-related polypeptide-specific antibodies are useful for identification of cells expressing either naturally-occurring or recombinant capsaicin receptor polypeptides or capsaicin receptor-related polypeptides, respectively, as well as the diagnosis of conditions and diseases associated with expression and/or function of capsaicin receptor and/or capsaicin receptor-related polypeptides. For example, anti-capsaicin receptor antibodies and anti-capsaicin receptor-related polypeptide antibodies can be used to detect increased or decreased receptor protein levels, and/or aberrant protein processing or oligomerization.

Anti-capsaicin receptor polypeptide antibodies and anti-capsaicin receptor-related polypeptide antibodies of the invention include, but are not limited to, polyclonal, monoclonal, chimeric, single chain, Fab fragments and fragments produced by a Fab expression library. Antibodies of particular interest include, for example, antibodies that stimulate capsaicin receptor function and/or block binding of capsaicin receptor-binding compounds to capsaicin receptor. Such antibodies may be useful in, for example, regulation of pain in pain syndromes, in screening assays for capsaicin receptor-binding agents, and in measurement of capsaicin receptor-activating compounds in a sample.

Capsaicin receptor polypeptides and capsaicin receptor-related polypeptides suitable for production of antibodies need not be biologically active; rather, the polypeptide, or oligopeptide need only be antigenic. Polypeptides used to generate capsaicin receptor-specific antibodies and capsaicin receptor-related polypeptide antibodies generally have an amino acid sequence consisting of at least five amino acids, preferably at least 10 amino acids. Preferably, antigenic capsaicin receptor polypeptides and antigenic capsaicin receptor-related polypeptides mimic an epitope of the native capsaicin receptor or native capsaicin receptor-related polypeptide, respectively. Antibodies specific for short polypeptides can be generated by linking the capsaicin receptor polypeptide or capsaicin receptor-related polypeptide to a carrier, or fusing the capsaicin receptor polypeptide or capsaicin receptor-related polypeptide to another protein (e.g., keyhole limpet hemocyanin), and using the carrier-linked chimeric molecule as an antigen. In general, anti-capsaicin receptor antibodies and capsaicin receptor-related polypeptide antibodies can be produced according to methods well known in the art. Recombinant immunoglobulins can be produced as according to U.S. Pat. No. 4,816,567, incorporated herein by reference.

Various hosts, generally mammalian or amphibian hosts, can be used to produce anti-capsaicin receptor antibodies and anti-capsaicin receptor-related polypeptide antibodies (e.g., goats, rabbits, rats, mice). In general, antibodies are produced by immunizing the host (e.g., by injection) with a capsaicin receptor polypeptide or capsaicin receptor-related polypeptide that retains immunogenic properties (which encompasses any portion of the native polypeptide, fragment or oligopeptide). Depending on the host species, various adjuvants can be used to increase the host's immunological response. Such adjuvants include but are not limited to, Freund's, mineral gels (e.g., aluminum hydroxide), and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies can be prepared using any technique that provides for the production of antibody molecules by immortalized cell lines in culture. These techniques include, but are not limited to, the hybridoma technique originally described by Koehler and Milstein (1975 Nature 256:495 497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al 1984 Proc Natl Acad Sci 81 :6851–4855; Neuberger et al 1984 Nature 312:604–608; Takeda et al 1985 Nature 314:452–454). Alternatively, techniques described for the production of single chain antibodies (U.S. Pat. No. 4,946,778) can be adapted to produce single chain antibodies that are capsaicin receptor-specific or capsaicin receptor-related polypeptide-specific.

Antibodies can be produced in vivo or by screening recombinant immunoglobulin libraries or panels of highly specific binding reagents as disclosed in Orlandi et al (1989, Proc Natl Acad Sci 86: 3833–3837), and Winter et al.(1991; Nature 349:293–299).

Antibody fragments having specific binding sites for a capsaicin receptor polypeptide or capsaicin receptor-related polypeptide can also be generated. For example, such fragments include, but are not limited to, F(ab')2 fragments, which can be produced by pepsin digestion of the antibody molecule, and Fab fragments, which can be generated by reducing the disulfide bridges of the F(ab')2 fragments. Alternatively, Fab expression libraries can be constructed to allow rapid and easy identification of monoclonal Fab fragments with the desired specificity (Huse et al 1989 Science 256:1275–1281).

A variety of protocols for competitive binding or immunoradiometric assays using either polyclonal or monoclonal antibodies having established antigen specificities are well known in the art. Such immunoassays typically involve, for example, the formation of complexes between a capsaicin receptor polypeptide and a specific anti-capsaicin receptor antibody, and the detection and quantitation of capsaicin receptor-antibody complex formation. A two-site, monoclonal-based immunoassay utilizing monoclonal antibodies reactive to two noninterfering epitopes on a specific capsaicin receptor protein is preferred, but a competitive binding assay can also be employed. These assays are described in Maddox et al 1983, J Exp Med 158:1211.

Diagnostic Assays Using Capsaicin Receptor-Specific or Capsaicin Receptor-Related Polypeptide-Specific Antibodies Particular capsaicin receptor antibodies and capsaicin receptor-related polypeptide antibodies are useful for the diagnosis of conditions or diseases characterized by abnormal expression or function of capsaicin receptor (e.g., detection of capsaicin receptor expression in skin to detect neuropathies or in assays to monitor patients having a capsaicin receptor-associated disorder or condition and/or being treated with capsaicin receptor agonists, antagonists, or inhibitors). For example, aberrant carp function might result from over- or under-production of a capsaicin receptor-related polypeptide; thus anti-capsaicin receptor-related antibodies can be used to detect these changes qualitatively or quantitatively. Diagnostic assays for capsaicin receptor or capsaicin receptor-related polypeptide include methods using a detectably-labeled anti-capsaicin receptor antibody or anti-capsaicin receptor-related polypeptide to detect capsaicin receptor in samples (e.g., extracts of cells or tissues). The polypeptides and antibodies of the present invention can be used with or without modification. Frequently, the polypeptides and antibodies are labeled by covalent or noncovalent attachment to a reporter molecule. A wide variety of such suitable reporter molecules are known in the art. Methods for detecting and quantitating antibody binding are well known in the art.

Pharmaceutical Compositions Containing Capsaicin Receptor Polypeptides, Capsaicin Receptor-Related Polypeptides, and/or Antibodies Thereto The present invention also encompasses pharmaceutical compositions that can comprise capsaicin receptor polypeptides, anti-capsaicin receptor polypeptide antibodies, capsaicin receptor-related polypeptides, or anti-capsaicin receptor-related polypeptides, alone or in combination with at least one other agent, such as a stabilizing compound, which can be administered in any sterile, biocompatible pharmaceutical carrier. The pharmaceutical compositions of the invention can be administered to a patient alone or in combination with other agents, drugs or hormones, in pharmaceutical compositions where it is mixed with excipient(s), or with pharmaceutically acceptable carriers. In one embodiment of the present invention, the pharmaceutically acceptable carrier is pharmaceutically inert.

Capsaicin receptor polypeptides and/or capsaicin receptor-related polypeptides can be administered in order to mitigate the effects of, for example, an endogenous factor that acts as a capsaicin receptor agonist or antagonist or to block or regulate the effects of a capsaicin receptor agonist or antagonist administered to an individual. Anti-capsaicin receptor polypeptide antibodies and/or anti-capsaicin receptor-related polypeptide antibodies can be administered to stimulate a capsaicin receptor in a desired fashion or to block the effects of an endogenous or exogenous capsaicin receptor-binding agonist or antagonist, e.g., via competitive binding to the capsaicin receptor. Pharmaceutical formulations comprising capsaicin receptor polypeptides, capsaicin receptor-related polypeptides, anti-capsaicin receptor antibodies, and/or anti-capsaicin receptor-related polypeptide antibodies can be formulated according to methods known in the art.

Transgenic Animals Expressing Polynucleotides Encoding Capsaicin Receptor and/or Capsaicin Receptor-Related Polypeptide Nucleic acids encoding capsaicin receptor and/or nucleic acids encoding capsaicin receptor-related polypeptide can be used to generate genetically modified non-human animals or site specific gene modifications in cell lines. The term "transgenic" is intended to encompass genetically modified animals having, for example, a deletion or other knock-out of capsaicin receptor gene activity (and/or capsaicin receptor-related polypeptide activity), an exogenous capsaicin receptor gene (or capsaicin receptor-related polypeptide gene) that is stably transmitted in the host cells, a "knock-in" having altered capsaicin receptor (and/or capsaicin receptor-related polypeptide) gene expression, or an exogenous capsaicin receptor or capsaicin receptor-related polypeptide promoter operably linked to a reporter gene. Of particular interest are homozygous and heterozygous knockouts and knock-ins of capsaicin receptor and/or capsaicin receptor-related polypeptide function.

Transgenic animals may be made through homologous recombination, where the endogenous capsaicin receptor locus (and/or capsaicin receptor-related polypeptide locus) is altered. Alternatively, a nucleic acid construct is randomly integrated into the genome. Vectors for stable integration include plasmids, retroviruses and other animal viruses, YACs, and the like. Of interest are transgenic mammals, preferably a mammal from a genus selected from the group consisting of Mus (e.g., mice), Rattus (e.g., rats), Oryctologus (e.g., rabbits) and Mesocricetus (e.g., hamsters).

A "knock-out" animal is genetically manipulated to substantially reduce, or eliminate endogenous capsaicin receptor function (and/or capsaicin receptor-related polypeptide function). Different approaches may be used to achieve the "knock-out". For example, a chromosomal deletion of all or part of the native capsaicin receptor homolog (or native capsaicin receptor-related polypeptide homolog) may be induced. Deletions of the non-coding regions, particularly the promoter region, 3' regulatory sequences, enhancers, or deletions of gene that activate expression of the capsaicin receptor gene and/or the capsaicin receptor-related polypeptide gene. A functional knockout may also be achieved by the introduction of an anti-sense construct that blocks expression of the native gene(s) (for example, see LI and Cohen (1996) Cell 85:319–329).

Conditional knockouts of capsaicin receptor gene function (and/or capsaicin receptor-related polypeptide gene function) are also included within the present invention. Conditional knock-outs are transgenic animals that exhibit a defect in capsaicin receptor gene function (and/or capsaicin receptor-related polypeptide gene function) upon exposure of the animal to a substance that promotes target gene alteration, introduction of an enzyme that promotes recombination at the target gene site (e.g., Cre in the Cre-loxP system), or other method for directing the target gene alteration.

For example, a transgenic animal having a conditional knock-out of capsaicin receptor gene function can be produced using the Cre-loxP recombination system (see, e.g., Kilby et al. 1993 Trends Genet 9:413–421). Cre is an enzyme that excises the DNA between two recognition sequences, termed loxP. This system can be used in a variety of ways to create conditional knock-outs of capsaicin receptor. For example, two independent transgenic mice can be produced: one transgenic for an capsaicin receptor sequence flanked by loxP sites and a second transgenic for Cre. The Cre transgene can be under the control of an inducible or developmentally regulated promoter (Gu et al. 1993 Cell 73:1155–1164; Gu et al. 1994 Science 265:103–106), or under control of a tissue-specific or cell type-specific promoter (e.g., a neuron-specific promoter). The capsaicin receptor transgenic is then crossed with the Cre transgenic to produce progeny deficient for the capsaicin receptor gene only in those cells that expressed Cre during development.

Transgenic animals may be made having an exogenous capsaicin receptor gene and/or exogenous capsaicin receptor-related polypeptide gene. The exogenous gene is usually either from a different species than the animal host, or is otherwise altered in its coding or non-coding sequence. The introduced gene may be a wild-type gene, naturally occurring polymorphism, or a genetically manipulated sequence, for example those previously described with deletions, substitutions or insertions in the coding or non-coding regions. The introduced sequence may encode an capsaicin receptor polypeptide and/or capsaicin receptor-related polypeptide. Where the introduced gene is a coding sequence, it is usually operably linked to a promoter, which may be constitutive or inducible, and other regulatory, sequences required for expression in the host animal.

Specific constructs of interest include, but are not limited to, anti-sense polynucleotides encoding capsaicin receptor or capsaicin receptor-related polypeptide, or a ribozyme based on a capsaicin receptor or capsaicin receptor-related polypeptide sequence, which will block capsaicin receptor expression or capsaicin receptor-related polypeptide expression, respectively. Such anti-sense polynucleotides or ribozymes will also block expression of dominant negative mutations and over-expression of the corresponding gene. Also of interest is the expression of constructs encoding capsaicin receptor or capsaicin receptor-related polypeptides in a host where the capsaicin receptor and/or capsaicin receptor-related polypeptide encoded by the construct is derived from a different species than the species of the host in which it is expressed (e.g., expression of human capsaicin receptor in a transgenic mouse). A detectable marker, such as lac Z may be introduced into the capsaicin receptor or capsaicin receptor-related polypeptide locus, where upregulation of expression of the corresponding gene will result in an easily detected change in phenotype. Constructs utilizing a promoter region of the capsaicin receptor gene or capsaicin receptor-related polypeptide gene in combination with a reporter gene are also of interest. Constructs having a sequence encoding a truncated or altered (e.g., mutated) capsaicin receptor or capsaicin receptor-related polypeptide are also of interest.

The modified cells or animals are useful in the study of function and regulation of capsaicin receptor and capsaicin receptor-related polypeptide. Such modified cells or animals are also useful in, for example, the study of the function of capsaicin receptor and capsaicin receptor-related polypeptides, as well as the study of the development of nociceptive neurons. Animals may also be used in functional studies, drug screening, etc., e.g. to determine the effect of a candidate drug on capsaicin receptor function or on symptoms associated with disease or conditions associated with capsaicin receptor function (e.g., capsaicin receptor defects or other altered capsaicin receptor activity). By providing expression of capsaicin receptor polypeptide and/ or capsaicin receptor-related polypeptide in cells in which it is otherwise not normally produced (e.g., ectopic expression), one can induce changes in cell behavior.

DNA constructs for homologous recombination will comprise at least a portion of the capsaicin receptor gene (or capsaicin receptor-related polypeptide gene) with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. 1990 Methods in Enzymology 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene. Chimeric animals having the modification (normally chimeric males) are mated with wildtype animals to produce heterozygotes, and the heterozygotes mated to produce homozygotes. If the gene alterations cause lethality at some point in development, tissues or organs can be maintained as allogeneic or congenic grafts or transplants, or in in vitro culture.

Investigation of genetic function may utilize nonmammalian models, particularly using those organisms that are biologically and genetically well-characterized, such as *C. elegans, D. melanogaster* and *S. cerevisiae*. For example, transposon (Tc1) insertions in the nematode homolog of a capsaicin receptor gene or a promoter region of a capsaicin receptor gene may be made. The capsaicin receptor gene sequences may be used to knock-out or to complement defined genetic lesions in order to determine the physiological and biochemical pathways involved in function of neuronal cells. It is well known that human genes can complement mutations in lower eukaryotic models.

Biosensor Membranes Having Capsaicin Receptor Polypeptides

Due to the responsiveness of capsaicin receptor polypeptides to heat, capsaicin receptor polypeptides can be used in a biosensor for detection of changes in temperature. The biosensor utilizes electrochemical measurement of an ion current across a lipid membrane (or other medium) having a capsaicin receptor polypeptide incorporated therein. Upon stimulation of the capsaicin receptor polypeptide by heat, the capsaicin receptor polypeptide facilitates movement of ions (e.g., calcium) across the membrane, which is then detected as a change in current across the lipid bilayer. The temperature and/or change in temperature can be correlated with the relative increase in conductance across the bilayer due to capsaicin receptor polypeptide activation.

It is well known that amphiphilic molecules can be caused to aggregate in solution to form two or three dimensional ordered arrays such as monolayers, micelles, black lipid membranes, and vesicles or liposomes, which vesicles may have a single compartment or may be of the multilamellar type having a plurality of compartments. The membrane may contain any suitable combination of lipids, long-chain ($C12-C24$) organic compounds, as well as plastic materials or like polymers for physical reinforcement. Methods and compositions for manufacture of lipid bilayers incorporating a protein of interest, as well as methods and compositions for manufacture of the electrical and mechanical components of biosensors are well known in the art (see, e.g., U.S. Pat. No. 5,328,847 (thin membrane sensor with biochemical switch); U.S. Pat. No. 5,443,955 (receptor membranes and ionophore gating); U.S. Pat. No. 5,234,566 (sensitivity and selectivity of ion channel biosensor membranes); U.S. Pat. No. 5,074,977 (digital biosensors and method of using same); and U.S. Pat. No. 5,156,810 (biosensors employing electrical, optical, and mechanical signals), each of which are hereby incorporated by reference for manufacture and use of biosensors incorporating a receptor of interest (i.e., capsaicin receptor).

Biosensors according to the present invention comprise at least one lipid membrane, where the membrane includes at least one capsaicin receptor polypeptide. Because capsaicin receptor polypeptides can function when contacted with ligand (e.g., capsaicin) or other effector that mediates capsaicin receptor activity (e.g., heat), the orientation of capsaicin receptor in the membrane is not substantially important for the function of the biosensor.

Conventional microelectronic configurations will serve adequately to supply power for the sensor, provide a constant direct current voltage across the bilayer prior to heat detection, and measure the ion current surge following capsaicin receptor activation elicited by a change in temperature. It may be additionally desirable to incorporate into the detection electronics a provision for membrane integrity determination, based on the electrical noise accompanying a triggered current signal.

In general, heat is detected using the biosensor of the invention by detecting a change in conductance across the capsaicin receptor polypeptide-containing bilayer. For example, the capsaicin receptor polypeptide lipid bilayer is provided so that a first face of the lipid bilayer (the "heat detection face") is in contact with an buffer solution of neutral pH and containing a selected cation that is capable of transport by the capsaicin receptor (e.g., any cation such as calcium or magnesium, preferably sodium), while a second face of the capsaicin receptor polypeptide lipid bilayer is in contact with a neutral pH buffer having a concentration of the selected cation that is significantly less than the concentration of selected cation in the buffer bathing the heat detection face of the bilayer. Upon exposure of the bilayer's heat detection face to a change in temperature, heat facilitates capsaicin receptor function to provide for transport of the selected cation across the bilayer, resulting in a change in conductance across the bilayer. The change in conductance is then correlated with a change in temperature.

The examples below are provided to illustrate the subject invention and are not included for the purpose of limiting the invention.

EXAMPLES

Example 1

Expression Cloning of Rat Capsaicin Receptor-Encoding DNA

While electrophysiological assays in Xenopus oocytes have been employed to obtain cDNAs encoding a variety of cell surface receptors and ion channels (Brake et al. 1995 Nature 371:519–523), this approach proved unsuccessful in identifying a capsaicin receptor clone. A mammalian cell expression cloning strategy based on the ability of capsaicin to trigger an influx of calcium ions into sensory neurons was developed. First, a rodent dorsal root ganglion plasmid cDNA library was constructed in pcDNA3 (Invitrogen) essentially as described (Brake et al., supra). A mixture of polyadenylated RNA from newborn (P1) rat and adult mouse dorsal root ganglia was used to generate first-strand cDNA using an oligo (dT) primer containing a Not1 restriction site. Following second strand synthesis and attachment of BstX1 adaptors, the cDNA was digested with Not1. cDNA and BstX1/Not1-linearized pcDNA3 were each purified on potassium acetate gradients, ligated together, and transformed in DH5α bacteria by electroporation. The resulting $2.4 \times 10^6$ independent bacterial clones were divided into 144 pools and stored at –80° C.

HEK 293 (human embryonal kidney) cells constitutively expressing the SV40 large T antigen were maintained in Medium A (DMEM supplemented with 10% fetal bovine serum (Hyclone), penicillin, streptomycin, and L-glutamine) at 37° C., 5% $CO_2$. Except where indicated, transient transfections were carried out with nearly-confluent cells that were replated at $3.2 \times 10^5$/35 mm tissue culture dish. After 24 hrs, the medium was replaced with 1 ml Medium B (DMEM supplemented with 10% dialyzed fetal calf serum, penicillin, streptomycin, and L-glutamine). After 2 hrs at 37° C., cells were transfected with 12 μg plasmid DNA using a calcium phosphate precipitation kit (Specialty Media). The following day, cells were rinsed once with phosphate buffered saline (PBS) containing 1 mM EDTA, washed from the plates, collected by centrifugation (200×g, 5 min, 22° C.), resuspended in Medium B, and re-plated onto polyornithine-coated coverslips. Under these conditions, each cell acquired plasmids encoding approximately 200 different cDNAs.

Between 6 and 24 hours later, cells were loaded with fura2 (30 min at 37° C.) in CIB buffer(mM: 130 NaCl, 3 KCl, 2.5 $CaCl_2$, 0.6 $MgCl_2$, 1.2 $NaHCO_3$, 10 Glucose, 10 Hepes, pH 7.45) containing 10 μM fura-2 acetoxymethyl ester and 0.02% pleuronic acid (Molecular Probes), then rinsed twice with CIB. Ratiometric calcium imaging was performed using a Nikon Diaphot fluorescence microscope equipped with a variable filter wheel (Sutter Instruments) and an intensified CCD camera (Hamamatsu). Dual images (at 340 nm and 380 nm excitation, 510 nm emission) were collected and pseudocolor ratiometric images monitored during the experiment (Metafluor imaging software, Universal Imaging). Cells were initially imaged in 200 ml CIB, after which 200 ml CIB containing capsaicin at twice the desired concentration was added. Following stimuli, cells were observed for 60–120 s. For each library pool, one microscopic field (300–500 cells) was assayed in each of eight wells.

While cells transfected with most of the assayed pools or with pcDNA3 alone exhibited no capsaicin responsiveness, 1% to 5% of the cells transfected with one of the cDNA library pools exhibited a profound increase in cytoplasmic calcium concentrations upon capsaicin treatment cDNA from this pool was further subdivided into smaller pools, and those subpools retransfected into HEK293 cells. In cell populations transfected with some of these subpools, an even larger fraction of cells responded to capsaicin, indicating that a capsaicin receptor-encoding cDNA had been enriched within the population. The process of pool subdivision and reassay was continued until a single plasmid was isolated that conferred capsaicin-responsiveness upon great than 70% of the transfected cells. The clone that conferred capsaicin-responsiveness contained a 3 kb cDNA insert.

Example 2

Sequencing and Characterization of Capsaicin Receptor-Encoding cDNA

The 3 kb cDNA insert was sequenced using an automated sequencer (ABI). Homology searches were performed against the nonredundant Genbank database and against an EST database (dbest) using blastn, blastx, and tblastx search programs. Hydrophilicity was calculated using the Hopp-Woods algorithm and a window size of ten 47. The insert was determined to be of rat origin by sequencing an independent cDNA isolated from a rat DRG library and a PCR product derived from mouse DRG cDNA. The sequence of the isolated rat capsaicin receptor-encoding polynucleotide (SEQ ID NO:1) and its corresponding amino acid sequence (SEQ ID NO:2) are shown in FIG. 1. Because a vanilloid moiety constitutes an essential chemical component of capsaicin and resiniferatoxin structures, the proposed site of action of these compounds is more generally referred to as the vanilloid receptor (Szallasi 1994 Gen. Pharmac. 25:223–243). Accordingly, the newly cloned cDNA was termed VR1, for vanilloid receptor subtype 1. The term "capsaicin receptor" as used herein encompasses VR1, but is not limited to VR1.

The VR1-encoding cDNA contains a 2514-nucleotide open reading frame encoding a protein of 838 amino acids with a predicted molecular mass of 95 kD (FIGS. 1 and 2A). Hydrophilicity analysis suggests that VR1 is a polytopic protein containing 6 transmembrane domains (noted as "TM" and shaded boxes in FIG. 1 and predicted to be mostly β-sheet (see FIG. 1B)) with an additional short hydrophobic stretch between transmembrane regions 5 and 6 (light shaded region). The amino-terminal hydrophilic segment (432 aa) contains a relatively proline-rich region followed by 3 ankyrin repeat domains (open boxes). The carboxyl-terminus (154 aa) contains no recognizable motifs.

A homology search of protein databases revealed significant similarities between VR1 and members of the family of putative store-operated calcium channels (SOCs) whose prototypical members include the drosophila retinal proteins TRP and TRPL 32, 33 (FIG. 1C). Members of this family have been proposed to mediate the entry of extracellular calcium into cells in response to the depletion of intracellular calcium stores 34. These proteins resemble VR1 with respect to their predicted topological organization and the presence of multiple amino-terminal ankyrin repeats 33. There is also striking amino acid sequence similarity between VR1 and SOCs within and adjacent to the sixth transmembrane region, including the short hydrophobic region between transmembrane domains 5 and 6 that may contribute to the ion permeation path 33. Outside these regions, VR1 shares little sequence similarity with SOCs, suggesting that VR1 is a distant relative of this family of channel proteins. Given the high permeability of VR1 to calcium ions, we nonetheless considered the possibility that it might function as a SOC.

An expressed sequence tag (EST) database homology search revealed several human clones bearing a high degree of similarity to VR1 at both the nucleotide and predicted amino acid levels (FIG. 1C). Three of these partial cDNAs, independently isolated from different sources, encode sequences in the vicinity of the predicted VR1 pore-loop and sixth transmembrane domains. As shown in FIG. 2C, the similarity of one of these clones (hVR, Genbank accession T12251) to the corresponding region of VR1 is extremely high (68% amino acid identity and 84% similarity within the region shown), suggesting that it is likely to be the human VR1 orthologue or a closely related subtype. Human EST clones corresponding to other domains of VR1 show comparable degrees of similarity (not shown) and could represent fragments of the same human transcript.

Example 3

VR1 Does Not Function as a Store-Operated Calcium Channel (SOC)

The amino acid sequence similarities between VR1 and SOCs suggested that the capsaicin receptor might function as an SOC. To test this, calcium-dependent inward currents were examined in VR1-expressing, intracellular calcium-depleted oocytes according to methods well known in the art.

Briefly, cRNA transcripts were synthesized from Not1-linearized VR1 cDNA templates using T7 RNA polymerase 17. Defolliculated Xenopus laevis oocytes were injected with 0.5–5 ng VR1 cRNA. Four to seven days after injection, two electrode voltage clamp recording was performed ($E_{hold}$=–60 mV for $IC_{50}$ curve and thermal stimulation experiments, and 40 mV for all other experiments) using a Geneclamp 500 amplifier (Axon Instruments) and a MacLab A/D converter (Maclab). The recording chamber was perfused at a rate of 2 ml/min with frog ringers solution containing (mM) 90 NaCl; 1.0 KCl, 2.4 $NaHCO_3$, 0.1 $BaCl_2$, 1.0 $MgCl_2$, and 10 HEPES, pH 7.6. at room temperature. Prior to performing the store-operated current assays, oocytes were incubated for 1–2 hrs in calcium-free, barium-free frog ringers solution containing 1 mM EGTA and 1 μM Thapsigargin. During voltage clamp recording, these oocytes were intermittently exposed to frog ringer's solution containing 2 mM Ca2+ and no EGTA to detect calcium-dependent currents (15 second pulses at 2 minute intervals) (Petersen et al. 1995 Biochem J. 311:4144).

In water-injected control oocytes, a clear depletion-induced current was seen, as previously described (Petersen et al., supra). In VR1-expressing oocytes, no quantitative or qualitative differences were observed in this response (not shown). Moreover, application of SKF 96365 (20 μM), an inhibitor of depletion-stimulated calcium entry (Merritt et al. 1990 Biochem J. 271:515–522), had no effect on capsaicin-evoked currents in VR1-expressing oocytes. Thus, VR1 does not appear to be a functional SOC under these circumstances.

Example 4

Sensory Neuron-Specific Expression of Capsaicin Receptor

The distribution of VR1 transcripts in neuronal and non-neural rat tissues was assessed by both Northern blot and in situ hybridization analyses. Adult Sprague-Dawley rats were euthanized by asphyxiation in $CO_2$ and tissues freshly dissected. Poly A+ RNA was purified either by lysis in guanidinium isothiocyanate followed by purification on oligo-dT cellulose or with the FastTrack kit (Invitrogen). Approximately 2 μg of each sample was electrophoresed through a 0.8% agarose-formaldehyde gel, transferred to a nylon membrane (Hybond N, Amersham), and hybridized with a $^{32}$P-labeled probe representing the entire VR 1 cDNA. Blots were washed at high stringency and autoradiographed. After probing with capsaicin receptor cDNA, the same filters were reprobed with a radiolabeled cyclophilin cDNA fragment as a control (e.g., to correct for relative RNA loading between samples).

For in situ hybridization histochemistry, adult female Sprague-Dawley rats were anesthetized and perfused with 4% paraformaldehyde in PBS. Dorsal root ganglia, trigeminal ganglia and spinal cord were dissected, frozen in liquid $N_2$, embedded in OCT mounting medium, and sectioned on a cryostat. Sections (15 micron) were processed and probed at 55° C. overnight with a digoxigenin-labeled cRNA generated by in vitro transcription of a 1 kb fragment of the VR1 cDNA (nt 1513–2482) using the Genius kit (Boehringer Mannheim). Sections were developed with alkaline phosphatase-conjugated anti-digoxigenin Fab fragments according to the manufacturer's instructions.

Both Northern blot analysis and in situ hybridization histochemistry indicated that VR1 transcripts are expressed selectively within dorsal root and trigeminal ganglia. An mRNA species of approximately 4 kb was prominently expressed in trigeminal and dorsal root sensory ganglia, both of which have been shown to contain capsaicin-sensitive neurons. This transcript was absent from all other tissues examined, including spinal cord and brain. A much smaller RNA species (approx. 1.5 kb) was detected in the kidney, but it is unclear whether this transcript could encode a functional VR1 protein.

In situ hybridization to assess the cellular pattern of VR1 expression within sensory ganglia showed that VR1 was expressed predominately within a subset of neurons with small diameters within both dorsal root and trigeminal ganglia. This is in keeping with the observation that most capsaicin-sensitive neurons have relatively small- to medium-sized cell bodies (Holzer 1991 Pharmacol. Rev. 43:143–201; Jansco et al. 1977 Nature 270:741–743). In contrast to the predominant expression of VR1 transcripts in neurons of the dorsal root ganglion, no visible signal was observed in the adjacent spinal cord dorsal horn. While binding sites for radiolabeled resiniferatoxin have been detected int eh dorsal horn, these sites are believed to reside on presynaptic terminal that project from primary nociceptors located within adjacent dorsal root ganglia Holzer 1991, supra). The results here support this interpretation.

Example 5

Assessment of VR1 Pharmacology in Xenopus Oocytes

To compare the pharmacological properties of the cloned capsaicin receptor to those of native vanilloid sites in sensory ganglia, VR1 was expression oocyte and used in whole-cell voltage clamp analysis to quantitatively examine its electrophysiological response to a variety of vanilloid agonists (capsaicin, resiniferatoxin) and antagonists (capsazepine). VR1 was expressed in Xenopus oocytes as described above (Example 3), except that $CaCl_2$ (2 mM) was used in place of $BaCl_2$ when generating the capsazepine inhibition curve. The agonists capsaicin and resiniferatoxin were applied sequentially to the same Xenopus oocyte expressing VR1. Membrane currents were recorded in the whole cell voltage clamp configuration ($V_{hold}$=–40 mV).

The results of the capsaicin and resiniferatoxin studies are shown in FIGS. 10A–10B. Bars denote duration of agonist application. At negative holding potentials, exposure to capsaicin or resiniferatoxin produced dose-dependent inward current responses in VR1 expressing oocytes, but not in water-injected control cells. As observed in sensory neurons (Winter et al. 1990 Brain Res. 520:131–140; Liu et al. 1994 Proc. Natl. Acad. Sci. USA 91:738–741), capsaicin-evoked current responses returned rapidly to baseline following agonist removal, whereas resiniferatoxin responses often failed to recover, even after a prolonged washout period. Half-maximal effective concentrations for these agonists were within an order of magnitude of those reported for native vanilloid receptors (Oh et al., supra; Bevan et al. 1992 Br. J. Pharmacol. 107:544–552), with resiniferatoxin being approximately 20-fold more potent than capsaicin ($EC_{50}$= 39.1 nM and 711.9 nM, respectively). Hill coefficients derived from these analyses (1.95 and 2.08, respectively) suggest that full activation of the receptor involves the binding of more than one agonist molecule, again consistent with previously described properties of native vanilloid receptors (Oh et al., supra; Szallasi 1994 Gen. Pharmac. 25:223–243).

As shown in FIGS. 11A and 11B, capsaicin-evoked responses in VR1 expressing oocytes were blocked by the competitive vanilloid receptor antagonist capsazepine at concentrations ($IC_{50}$=283.5 nM) that inhibit native receptors (FIGS. 10A–10B). The current tracing shows that the block of capsaicin activity (cap; 0.6 $\mu$M) by capzasepine (cpz; 10 $\mu$M) is reversible. Another pharmacological signature of vanilloid receptors is their sensitivity to the noncompetitive antagonist ruthenium red (RR; 10 $\mu$M), which also blocked capsaicin-evoked responses (cap; 0.6 $\mu$M) in a reversible manner (FIG. 11B). Responses to resiniferatoxin (50 nM) were also reversibly antagonized by capzasepine (5 $\mu$M) or ruthenium red (10 $\mu$M) (not shown).

Example 6

Patch Clamp Analysis Of Recombinant Capsaicin Receptors Expressed In HEK293 Embryonal Kidney Cells The recombinant capsaicin receptor cloned in Example 1 was further characterized in studies using patch clamp analysis in capsaicin receptor-expressing HEK293 cells. HEK293 cells transfected with a control vector (pcDNA3 without a capsaicin receptor-encoding sequence). Patch-clamp recordings were carried out with transiently transfected HEK293 cells at 22° C. Standard bath solution for whole-cell recordings contained (mM) 140 NaCl, 5 KCl, 2 $MgCl_2$, 2 $CaCl_2$, 10 HEPES, 10 glucose, pH 7.4 (adjusted with NaOH). In calcium-free bath solution, $CaCl_2$ was removed and 5 mM EGTA was added.

For monovalent cation substitution experiments, after the whole-cell configuration was obtained in control bath solution, the bath solution was changed to (mM): 140 NaCl (or KCl or CsCl), 10 glucose, and 10 HEPES (adjusted to pH 7.4 with NaOH, KOH or CsOH, respectively) and the reversal potential measured using voltage-ramps. For divalent cation permeability experiments, the bath solution was changed to (mM) 110 $MgCl_2$ (or $CaCl_2$), 2 $Mg(OH)_2$ (or $Ca(OH)_2$), 10 glucose, 10 HEPES, pH 7.4 (adjusted with HCl).

Bath solution for outside-out patch recordings and pipette solution for inside-out patch recordings contained (mM) 140 NaCl, 10 HEPES, pH 7.4 (adjusted with NaOH). Bath solution for inside-out patch recordings and pipette solutions for outside-out patch recordings and ion substitution experiments contained: (mM) 140 NaCl, 10 HEPES, 5 EGTA, pH 7.4 (adjusted with NaOH). Pipette solution for whole-cell recordings contained (mM) 140 CsCl (or 130 CsAspartate and 10 NaCl), 5 EGTA, 10 HEPES, pH 7.4 (adjusted with CsOH). Liquid junction potentials were measured directly in separate experiments; they did not exceed 3 mV with solutions used and no correction for this offset was made.

Whole-cell recording data were sampled at 20 kHz and filtered at 5 kHz for analysis (Axopatch 200 amplifier with pCLAMP software, Axon Instruments). Single-channel recording data were sampled at 10 kHz and filtered at 1 kHz. Permeability ratios for monovalent cations to Na ($P_X/P_{Na}$) were calculated as follows:

$$P_X/P_{Na} = \exp(\Delta V_{rev} F/RT),$$

where $V_{rev}$ is the reversal potential, F is Faraday's constant, R is the universal gas constant, and T is absolute temperature. For measurements of divalent permeability, $P_Y/P_{Na}$ was calculated as follows:

$$P_Y/P_{Na} = [Na^+]_I, \exp(\Delta V_{rev} F/RT)(1+\exp(\Delta_{rev} F/RT))/4[Y^{2+}]_O.$$

Ion activity coefficients of 0.75 (sodium) and 0.25 (calcium or magnesium) were used as correction factors.

Figure 3:
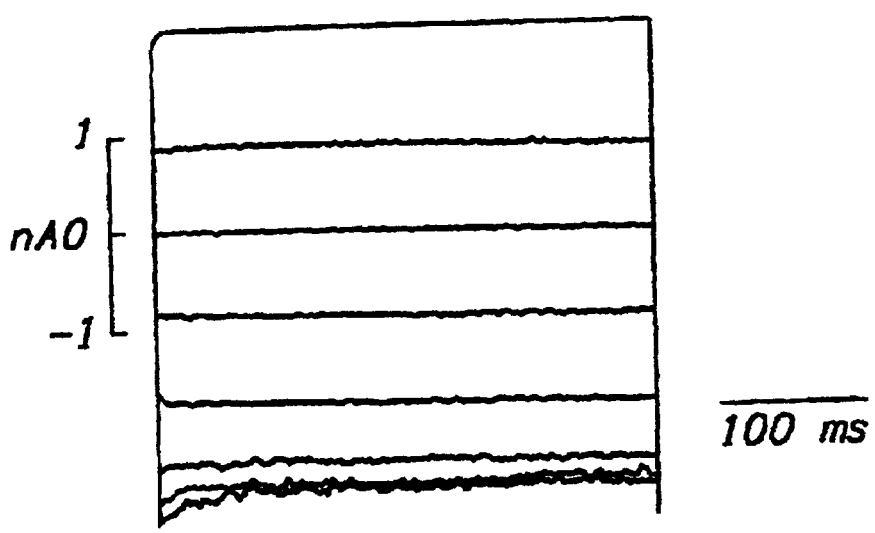
FIG. 3 is a plot of the voltage steps (400 ms) from −100 mV to +40 mV for the data presented in FIG. 3.
Figure 4:
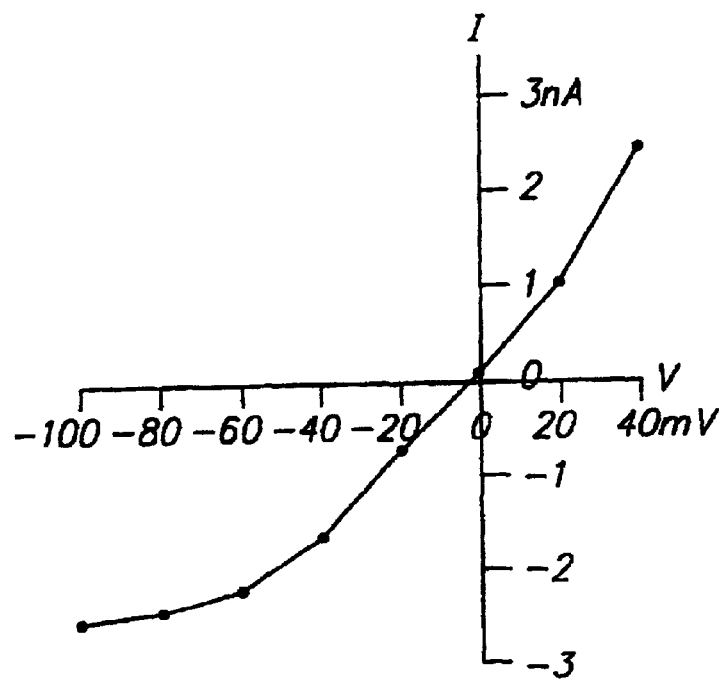
FIG. 4 is a graph illustrating the current-voltage relationship of the data from FIG. 4.

FIG. 3 show the results of whole cell voltage clamp analysis of capsaicin receptor-expressing HEK293 cells at –60 mV using a CsAsparate-filled pipet. These data show an inward cation-specific current which is present only during capsaicin treatment (the time period during which capsaicin was present (1 $\mu$M) is indicated by the bar above the plot), and which developed with a short latency upon bath application of capsaicin. No such currents were observed on control, mock-transfected cells. FIG. 4 shows the voltage steps (400 ms) from –100 mV to +40 mV (vertical lines in FIG. 3) on an expanded time scale. The currents in the absence of capsaicin (a) were subtracted rom the currents obtained in the presence of capsaicin (b). This analysis of the data revealed a time-independent, receptor-dependent current. In calcium-free medium, the capsaicin-evoked current was also time-independent both at a constant holding potential of −60 mV (FIG. 3) and during voltage steps from −100 to +40 mV (in 20 mV increments, FIG. 4). This property enabled characterization of capsaicin-mediated currents under steady-states response conditions in subsequent experiments. Current-voltage relations derived from these data show that such responses exhibit prominent outward rectification resembling that observed in cultured dorsal root ganglion neurons (FIG. 4; Oh et al., supra). Because the bath solution used in these experiments consisted mainly of sodium chloride, whereas the patch pipet was filled with cesium aspartate, the observed reversal potential close to 0 mV ($E_{rev}$=0.5±0.9 mV; n=13) indicates that the capsaicin-mediated response involves the opening of a cation-selective channel.

Figure 5:
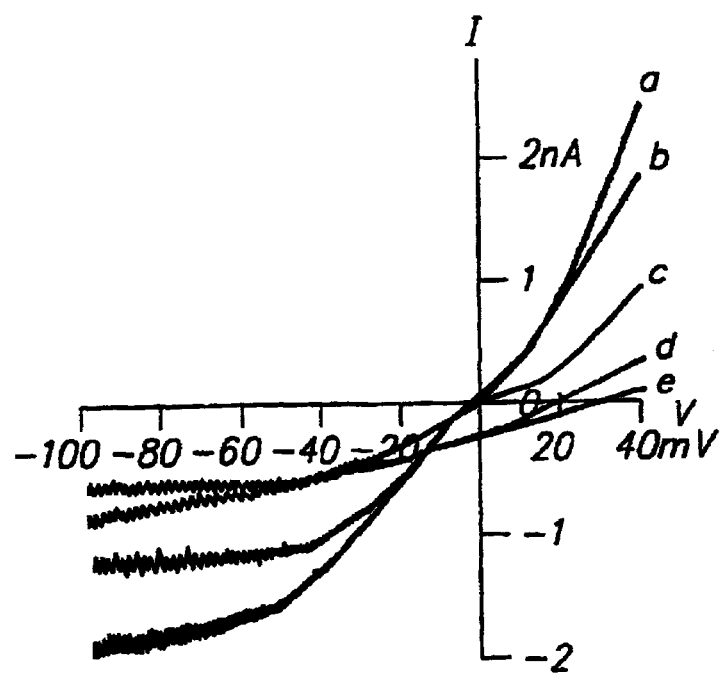
FIG. 5 is a graph of the voltage generated across membranes of recombinant capsaicin receptor-expressing cells when exposed to capsaicin and tested under conditions of varying ionic compositions. a=NaCl; b=KCl; c=CsCl; d=$MgCl_2$; e=$CaCl_2$.

In sensory neurons, vanilloid-evoked currents are carried by a mixture of mono- and divalent cations (Bevan et al. 1990 Trends Pharmacol. Sci. 11:330–333; Oh et al., supra; Wood et al. 1988 J. Neuroscience 8:3208–3220). This phenomena was examined in VR1-expressing mammalian cells through a series of ion substitution experiments to examine the relative contributions of various cations to capsaicin-evoked currents in VR1-expressing cells. Current-voltage relations established for cells bathed in solutions of differing cationic compositions (FIG. 5; $Na^+$ (labeled a), $K^+$ (labeled b), $Cs^+$ (labeled c), $Mg^{++}$ (labeled d), or $Ca^{++}$ (labeled e) revealed that VR1 does not discriminate among monovalent cations, but exhibits a notable preference for divalent cations. Replacement of extracellular NaCl (140 mM) with equimolar KCl or CsCl did not significantly shift reversal potential ($E_{rev}$=−0.7±1.2 mV, n=8;−1.5 mV, n=9;−4.3±0.9 mV, n=8, respectively. $P_K/P_{Na}$=0.94; $P_{CS}/P_{Na}$=0.85). Replacement of extracellular NaCl with isotonic (112 mM) $MgCl_2$ or $CaCl_2$ shifted $E_{rev}$ to 14.4±1.3 mV (n=3) or 24.3±2.3 mV (n=7), respectively. As summarized in FIG. 5, the data thus revealed that the capsaicin receptor-expressing cell membranes had the following relative cation permeabilities for the capsaicin-activated current: $Ca^{++}>Mg^{++}>>Na^+\approx K^+\approx Cs^+$. The very high relative permeability of VR1 to calcium ions ($P_{Ca}/P_{Na}$=9.60;$P_{Mg}/P_{Na}$=4.99) exceeds that observed for most non-selective cation channels and is comparable to values reported for NMDA-type glutamate receptors ($P_{Ca}/P_{Na}$=10.6) (Mayer et al. 1987 J. Physiol. 394:501–527), which are noted for this property. With all bath solutions examined, an outwardly rectifying current-voltage relation was observed, although this feature was somewhat less prominent in $MgCl_2$- or $CaCl_2$-containing bath solutions.

In cultured sensory neurons, electrophysiological analyses of vanilloid-evoked responses have shown them to be kinetically complex and to desensitize with continuous vanilloid exposure (Liu et al., supra: Yeats et al. 1992 J. Physiol. 446:390P). This electrophysiological desensitization (which might underlie aspects of physiological desensitization produced by vanilloids in vivo) appears to depend, in part, upon the presence of extracellular calcium(Yeats et al., supra; Holzer 1991 Pharmacol. Rev. 43:143–201). To test the calcium dependency of VR1-expressing cells ability to respond to capsaicin, whole-cell current responses were tested in both calcium-containing standard bath solution and in calcium-free solution (FIGS. 6A–F). Capsaicin (1 $\mu M$) was applied every 5 min; CsCl was used as pipette solution. The ratios of current size at the end of the third application to the peak of the first application were 95.3±2.6% (n=3) in calcium-free solution, and 13.0±4.3% (n=5) in calcium-containing solution (T test; p<0.00001). Indeed, in the absence of extracellular calcium, capsaicin evoked responses in VR1-transfected cells showed little or no desensitization during prolonged agonist application or with successive agonist challenges (4.7±2.3% decrease between first and third applications, n=3). In contrast, responses evoked in calcium-containing bath solution consisted of at least two distinct components: one desensitizing (87±4.3% decrease between first and third applications, n=5); and one relatively non-desensitizing. Thus, desensitization and multiphasic kinetics of vanilloid-evoked responses can be reproduced outside of a neuronal context and distinguished by their dependence on ambient calcium levels.

Figure 8:
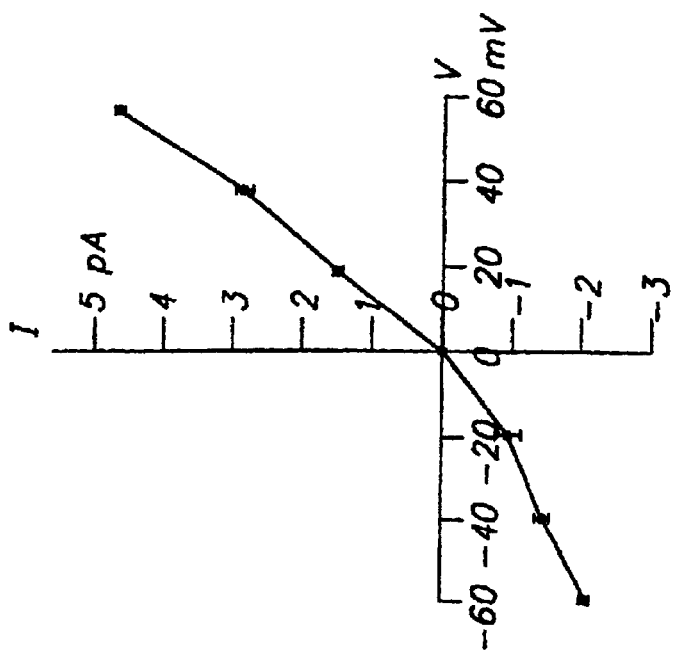
FIG. 8 is a graph showing the current-voltage relationship of the data obtained in FIG. 7.
Figure 7:
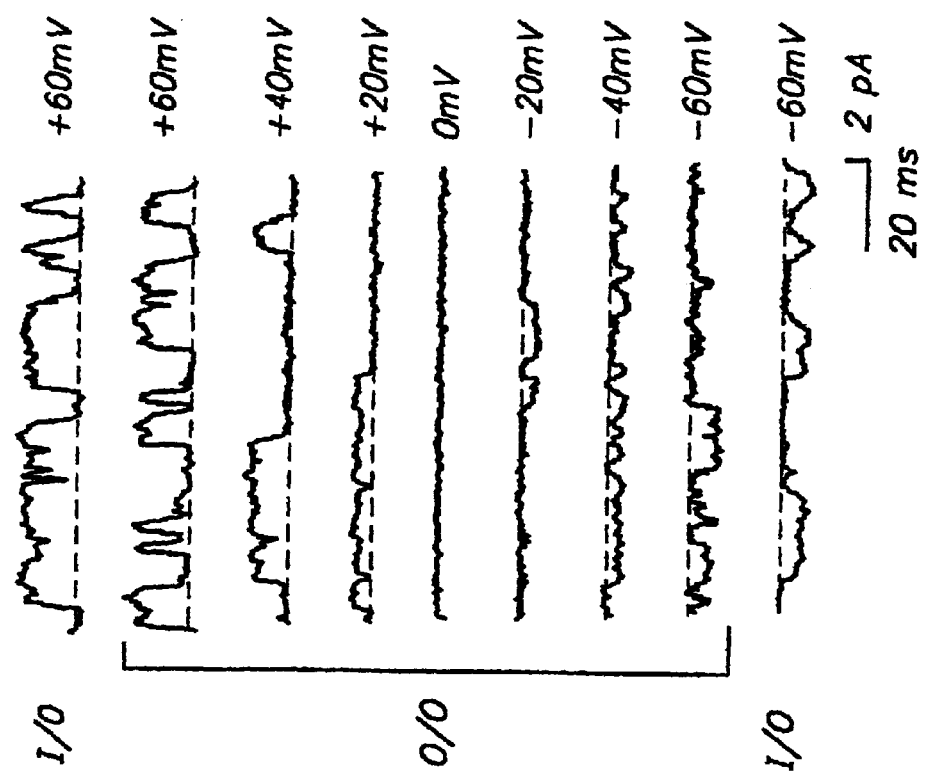
FIG. 7 is graph illustrating the single channel behavior of capsaicin-induced current in capsaicin receptor-expressing HEK293 cells using outside-out (O/O) and inside-out (I/O) patches.

The behavior of the VR1 response was also examined in membrane patches excised from transfected cells. Inside-out (I/O) or outside-out (O/I) patches were excised from VR1-transfected cells and analyzed in symmetrical 140 mM NaCl at the indicated holding potentials with capsaicin (1 $\mu M$) in the bath solution. Dashed lines in the data represented in FIG. 7 indicate closed channel state. In other patches, multiple simultaneous channel openings were observed. The large and well resolved currents of unitary amplitude observed only in the presence of capsaicin (FIG. 7) indicate the existence of capsaicin-gated ion channels within these patches, whose activation does not depend upon soluble cytoplasmic components. The current voltage curve of mean single channel amplitudes (± s.e.m.; FIG. 8), which was calculated from data shown in FIG. 7, also exhibits pronounced outward rectification. The current-voltage relation at the single-channel level was essentially identical to that established in whole-cell configuration, owing to its outward rectification and reversal potential near 0 mV under similar ionic conditions. Unitary conductances of 76.7 pS at positive potentials and 35.4 pS at negative potentials were observed with sodium as the sole charge carrier. These single channel properties mirror those previously described for native vanilloid receptors(Oh et al., supra; Forbes et al. 1988 Neurosci. Lett. Suppl. 32:S3).

It has been suggested that the site of vanilloid action may not be confined to the extracellular side of the plasma membrane, reflecting the lipophilic nature of these compounds (James et al. in Capsaicin in the Study of Pain (ed. Wood) Pgs. 83–104 (Academic Press, London, 1993). Interestingly, capsaicin was able to produce identical responses when added to either side of a patch excised from a VR1-expressing cell (FIG. 7), consistent with the notion that vanilloids can permeate or cross the lipid bilayer to mediate their effects. A less likely, but formally consistent explanation is that vanilloid receptors have functionally equivalent capsaicin binding sites on both sides of the plasma membrane.

These data show that the cloned capsaicin receptor behaves in patch clamp analysis in a manner very similar to that reported for wildtype capsaicin receptor.

Example 7

Use of Recombinant Capsaicin Receptor to Quantitate Vanilloid Concentrations

As has been recognized for years, the relative pungencies of pepper varieties span an enormously wide range, reflecting, in part, differences in vanilloid content To-date, methods for rating peppers with respect to their relative "hotness" have relied on subjective psychophysical assays (in which values are reported in Scoville units) (Scoville 1912 J. Am. Pharm. Assoc. 1:453–454) or on biochemical determination of capsaicin content (Woodbury 1980 J. Assoc. Off. Anal. Chem. 63:556–558). To further explore whether the electrophysiological response of the cloned vanilloid receptor to pepper extracts was in proportion to ability of these peppers to evoke pain.

Figure 11:
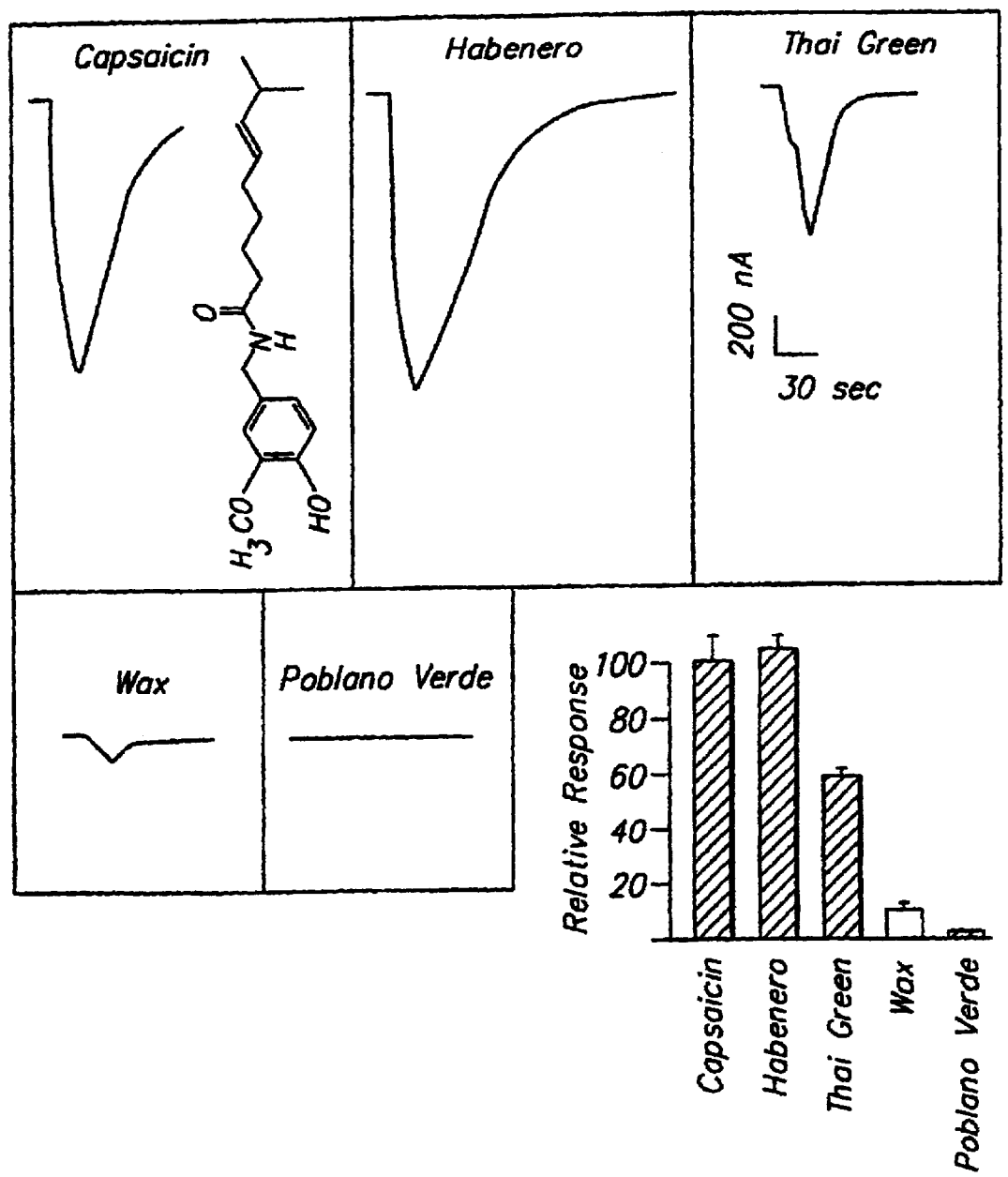
FIG. 11 is a histogram with corresponding current traces reflecting the relative capsaicin content of several different hot peppers.

Several different types of hot peppers (15 g; Thai green, poblano verde, habanero, and wax) were minced and extracted overnight at room temperature with 50 ml absolute ethanol. Soluble extracts were concentrated 15-fold by vacuum desiccation, then diluted 1000-fold in frog ringer's solution for electrophysiological assay. Equivalent fractions (normalized to pepper weight) were tested for their ability to activate the recombinant capsaicin receptor expressed in Xenopus oocytes. Capsaicin receptor activation was assessed using a two-electrode voltage-clamp assay to quantitatively measure currents elicited by each pepper extract. Responses were normalized to the response obtained with pure capsaicin (10 $\mu$M set at 100). The data are shown in FIG. 11 (each value represents an average of four independent determinations, each from separate oocytes; 30 sec application). The relative response of the cloned receptor to the pepper samples and the capsaicin control are shown in the histogram with representative current traces shown to the right of each bar in the histogram. Extracts evoked no response in water-injected cells.

The relative responses of capsaicin receptor to the pepper extracts correlates with the relative hotness of each pepper as determined by conventional analyses and Scoville heat unit assignments. Moreover, the differential "hotness" of these pepper variants, as determined by subjective psychophysical ratings (Berkeley et al. Peppers: A Cookbook pgs. 1–120 (Simon and Schuster, New York, 1992), correlated with their rank order potencies as activators of VR1.

Example 8

Capsaicin Induces Death of Cells Expressing VR1

Figure 12:
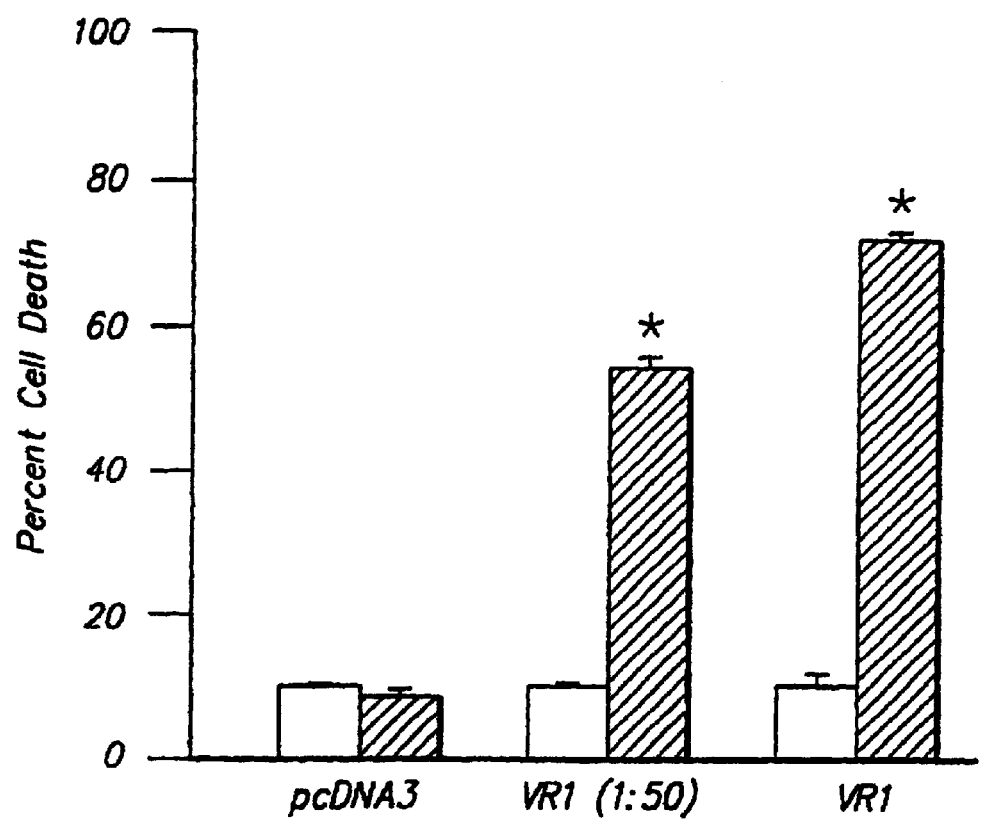
FIG. 12 is a graph showing induction of cell death in HEK293 cells transiently transfected with capsaicin receptor-encoding cDNA. Open bars=cells exposed to carrier alone (ethanol); filled bars=cells exposed to capsaicin; pcDNA3=control cells without capsaicin receptor-encoding DNA; VR1 (1:50)=cells transiently transfected with capsaicin receptor-encoding cDNA diluted 1:50 with control pcDNA3; and VR1=cells transiently transfected with capsaicin receptor-encoding cDNA alone. Asterisks indicate a significant difference from ethanol-treated cells.

Capsaicin is widely recognized as a neurotoxin that selectively destroys primary afferent nociceptors in vivo and in vitro (Jansco et al. 1977 Nature 270:741–743; Wood et al. 1988 J. Neuroscience 8:3208–3220). In order to determine whether this selective toxicity solely is a reflection of the specificity of receptor expression, or whether it depends upon additional properties of sensory neurons or their milieu, the ability of capsaicin to kill non-neuronal cells expressing vanilloid receptors was examined in vitro. HEK293cells were transiently transfected with either vector alone (pcDNA3), vanilloid receptor cDNA diluted 1:50 in pcDNA3 (VR1 1:50) or vanilloid receptor cDNA alone (VR1). Fourteen hours later, culture medium was replaced with medium containing capsaicin (3 $\mu$M, filled bars) or vehicle (ethanol 0.3%, open bars) (FIG. 12). After seven hours at 37° C., the percentage of dead cells was determined using ethidium homodimer staining. Data represent the mean ± s.e.m. of triplicate determinations from a representative experiment. Asterisks indicate a significant difference from ethanol-treated cells (T-test, P<0.0001). Similar results were obtained in three independent experiments.

As shown in FIG. 12, within several hours of continuous exposure to capsaicin, HEK293 cells transfected with VR1 exhibited rampant death, as determined morphologically and by the use of vital stains. In contrast, cells transfected with vector alone were not killed by this treatment. The cell death was characterized by prominent cytoplasmic swelling, coalescence of cytoplasmic contents, and eventual lysis. Thus, VR1 expression in a non-neuronal context can recapitulate the cytotoxicity observed in vanilloid-treated sensory neurons. Staining with Hoechst dye 33342 revealed no evidence of the nuclear fragmentation often associated with apoptotic cell death 28 (not shown). Together, these observations are consistent with necrotic cell death resulting from excessive ion influx, as has been proposed for vanilloid-induced death of nociceptors (Bevan et al. 1990 Trends Pharmacol. Sci. 11:330–333), glutamate-induced excitotoxicity (Choi 1994 Prog. Brain Res. 199:47–51), and neurodegeneration caused by constitutively activating mutations of various ion channels (Hong et al. 1994 Nature 367:470–473; Hess 1996 Neuron 16:1073–1076).

Example 9

Hydrogen Ions Potentiate The Effect Of Capsaicin On VR1

A reduction in tissue pH resulting from infection, inflammation, or ischemia can produce pain in mammals. This effect has been attributed to the ability of protons to activate excitatory channels on the surface of nociceptive neurons. A subset of these responses have been reported to share properties in common with those elicited by vanilloids, including similar kinetics, ion selectivity, and antagonism by ruthenium red (Bevan et al. 1994 Trends Neurosci. 17:509–512). Moreover, subthreshold concentrations of hydrogen ions have been shown to potentiate the effects of low concentrations of capsaicin in sensory neurons (Petersen et al. 1993 Pain 54:37–42; Kress et al. 1996 Neurosci. Left. 211:5–8). It has therefore been proposed that protons might act as endogenous activators or modulators of vanilloid receptors (Bevan et al. 1994 supra).

Figure 14:
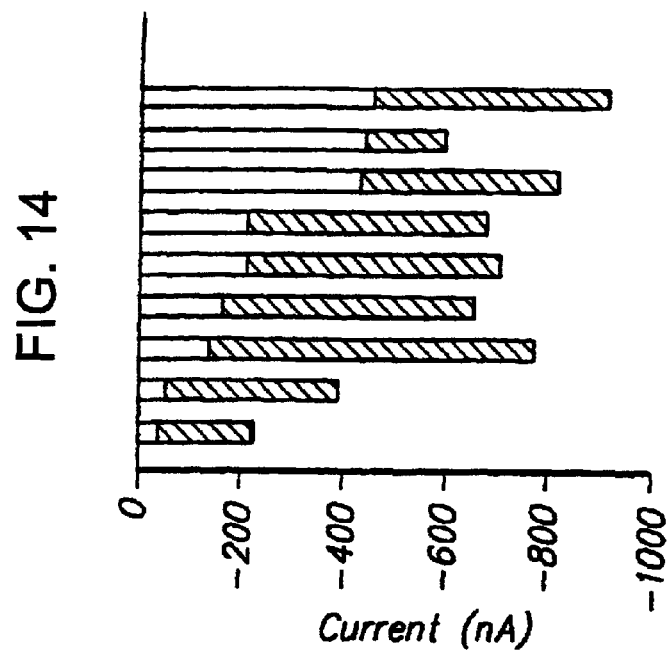
FIG. 14 is a graph showing a summary of the current response obtained from nine independent capsaicin receptor-expressing oocytes. The grey portion of each bar indicates peak current evoked by capsaicin at pH 7.6, while the black portion represents the additional current evoked by changing the bath solution to pH 6.3.

To address this possibility, the effects of hydrogen ions on the cloned vanilloid receptor were examined using the oocyte expression system. Capsaicin (0.3 $\mu$M) was administered throughout the time period tested (spanned by the arrows in FIG. 13) ($V_{hold}$=−40 mV). The pH of the bath solution was changed during the experiment (as indicated by the horizontal bars in FIG. 13). VR1-expressing oocytes exhibited no responses to pH 6.3 bath solution without capsaicin; water-injected control oocytes exhibited no responses to either capsaicin or pH 6.3 bath solution (not shown). The current responses obtained from 9 independent VR1-expressing oocytes are summarized in FIG. 14. The grey portion of each bar indicates peak current evoked by capsaicin at pH 7.6, while the black portion represents the additional current evoked by changing the pH to 6.3.

Figure 13:
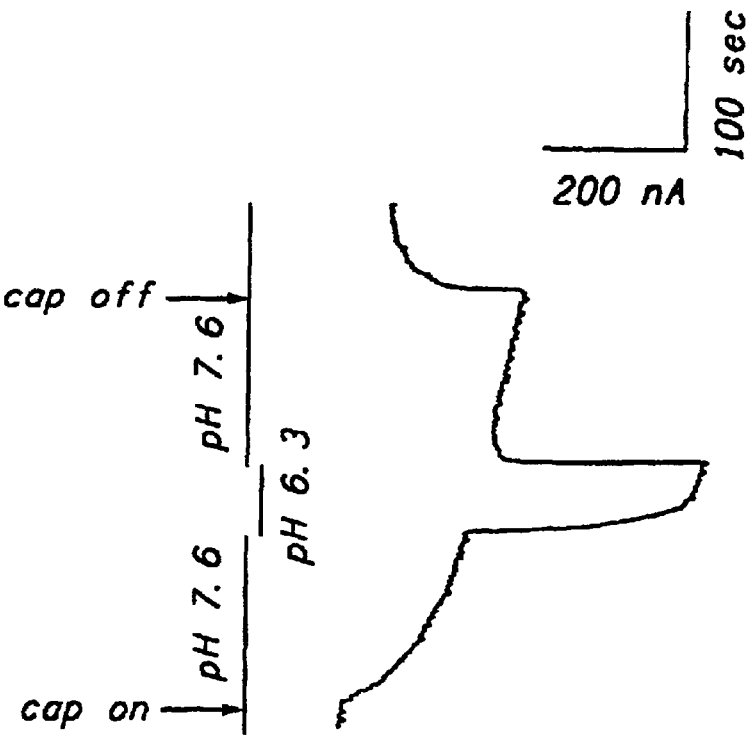
FIG. 13 is a current trace showing the effect of hydrogen ions upon capsaicin receptor activity in oocytes expressing capsaicin receptor. cap on=time of capsaicin introduction; cap off=time of capsaicin wash out. The pH of the bath solution was changed during the experiment as indicated by the horizontal bars.

Abrupt reduction in bath solution pH (from 7.6 to 5.5) was not sufficient to activate VR1 in the absence of capsaicin (fewer than 10% of VR1-expressing oocytes treated in this way exhibited a large inward current (not shown)), suggesting that hydrogen ions alone cannot efficiently activate this protein. Next, the effect of both capsaicin and pH on VR1 activation was examined. VR1-expressing oocytes were treated with a submaximal concentration of capsaicin (500 nM) at pH 7.6 (FIG. 13). Once their current responses reached a relatively stable plateau, the oocytes were exposed to a solution containing the same concentration of capsaicin at pH 6.3. Under these conditions, the inward current rapidly increased to a new plateau up to five-fold greater in magnitude than the first, Upon returning to pH 7.6, the oocyte response subsided to its initial plateau, and upon the removal of capsaicin it returned to baseline. This potentiation was seen only with sub-saturating concentrations of agonist, as reduced pH did not augment responses to 10 $\mu$M capsaicin (not shown). These results suggest that while hydrogen ions alone are not sufficient to activate VR1, they can markedly potentiate capsaicin-evoked responses.

Example 10

The Vanilloid Receptor Is Activated By Noxious Heat

The effects of elevated temperature on VR1 activity in calcium influx, conductance, and capsaicin and RR responsivity were examined.

a) Effect of Heat Upon Intracellular Calcium

The effects of heat upon VR1 activity in mediating calcium influx were examined using transfected HEK293 cells and the flourescent calcium influx screening method described above. Cells were analyzed using microscopic fluorescent calcium imaging before and immediately after the addition of heated calcium imaging buffer (300 ml CIB at 65° C. was applied to cells residing in 150 ml CIB at 22° C.) Under these conditions, cells were transiently exposed to a peak temperature of ~45° C.

While cells transfected with vector alone exhibited only a mild, diffuse change in cytoplasmic free calcium, a large proportion of cells expressing VR1 exhibited a pronounced elevation of calcium levels within seconds of heat treatment. These responses subsided within a few minutes and a subsequent challenge with capsaicin produced a characteristic calcium response, suggesting that the response to heat is a specific signaling event and not a consequence of non-specific membrane perturbation or disruption to cell integrity.

b) Effect of Heat Upon Conductance

Whole-cell patch-clamp analysis ($V_{hold}$=−60 mV) of VR1-transfected HEK293 cells was performed to examine whether specific heat-evoked membrane currents are associated with this phenomenon. The temperature of the bath medium was raised from 22° C. to 48° C. (heat) and then restored to 22° C., after which capsaicin (0.5 $\mu$M) was added to the bath. Ionic conditions were identical to those described for the data in FIG. 2. Voltage-ramps (−100 to +40 mV in 500 ms) were applied before, between, and during responses.

Figure 15A:
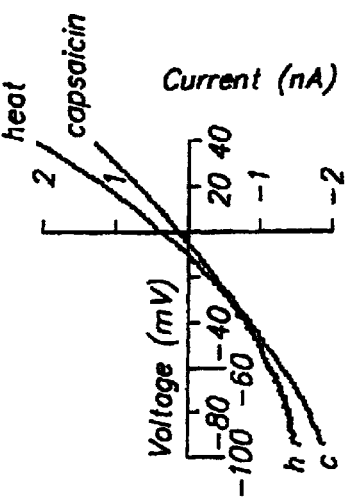
FIG. 15A is a current trace showing the effects of heat and capsaicin upon capsaicin receptor activity in capsaicin receptor-expressing HEK293 cells as determined by whole patch clamp analysis.
Figure 15B:
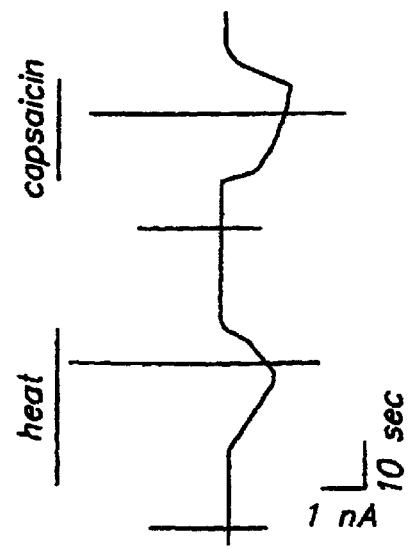
FIG. 15B is a graph showing the current-voltage relationship of the data obtained in FIG. 15A.

Exposure of these cells to a rapid increase in temperature (22° C. to 50° C. in 25 seconds, monitored with an in-bath thermistor) produced large inward currents (791±235 pA at −60 mV; n=9) that were typically similar in amplitude to that evoked by a subsequent application of capsaicin at 500 nM (FIG. 15A). Both heat- and vanilloid-evoked responses showed outward rectification, suggesting that they are mediated by the same entity (FIG. 15B). By comparison, thermally-evoked responses of control, vector-transfected cells were much smaller and exhibited no rectification (131±23 nA, n=8). In addition, the heat response in VR1-transfected cells desensitized during stimulus application, whereas the small thermal response observed in control vector-transfected cells did not. These results suggest that VR1 is acting as a thermal transducer, either by itself or in conjunction with other cellular components.

c) Heat Activation of VR1 in Oocytes

Figure 16:
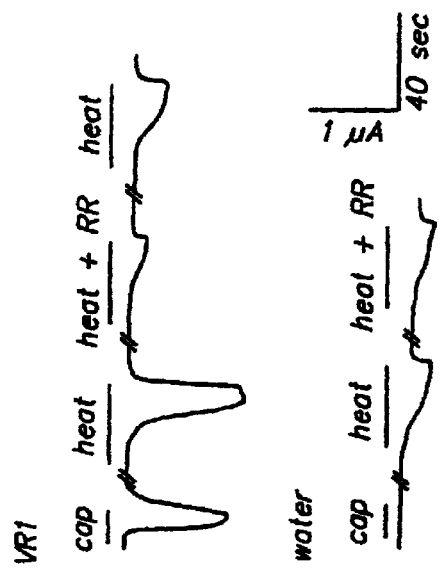
FIG. 16 is a graph showing activation of capsaicin receptor in capsaicin receptor-expressing Xenopus oocytes by noxious, but not innocuous, heat The asterisk indicates a significant difference from control water-injected oocytes.

To determine whether VR1 could mediate similar responses to heat in a different cellular environment, heat activation of VR1 was tested in the oocyte system. Oocytes injected with either VR1 cRNA or water were subjected to two-electrode voltage-clamp ($V_{hold}$=−60 mV) while the temperature of the perfusing buffer was raised from 22.7° C. to the level indicated, then held constant for 60 sec. The magnitudes of the resulting inward currents are shown in FIG. 16 as the mean ± s.e.m. (VR1, n =8; water, n=6 independent cells). The asterisk indicates a significant difference from water-injected oocytes (T-test, P<0.0005).

In control, water injected oocytes, acute elevation of perfusate temperature produced a small inward current that increased linearly up to 50° C. (FIG. 16). VR1 expressing oocytes exhibited similar responses at temperatures up to 40° C., but above this threshold, their responses were significantly larger than those of controls. Thus, even in this non-mammalian context, the VR1-mediated temperature response profile is remarkably consistent with that reported for thermal nociceptors (Fields, supra).

d) Inhibition of VR1 Heat Activation by Ruthenium Red

To further determine whether heat acts specifically through the capsaicin receptor, the ability of ruthenium red to inhibit the heat-mediated response was tested in VR1-expressing oocytes in the system described above. The current tracings shown in FIG. 17 were generated from representative VR1- or water-injected oocytes ($V_{hold}$=−60 mV) during successive applications of the indicated stimuli.

VR1-injected oocytes exhibited the following mean inward current responses ± s.e.m. (n=5): capsaicin (1 $\mu$M), 1221±148 nA; heat (50° C.), 2009±134 nA; heat plus ruthenium red (10 $\mu$M), 243±47 nA. Inhibition by ruthenium red was significant (88±2%, n=5; Paired T-test, P<0.0001). No diminution in current response was observed when successive heat pulses were administered in the absence of ruthenium red. Water-injected oocytes showed no response to capsaicin and much smaller responses to heat (338±101 nA, n=5). Ruthenium red inhibited these responses by only 21±26% (n=5; Paired T-test, P<0.1).

Figure 17:
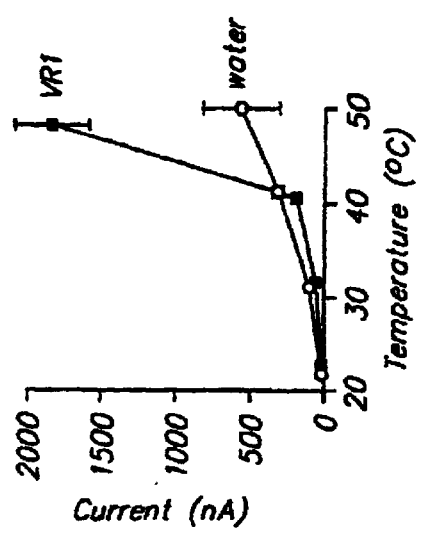
FIG. 17 provides representative current traces of the effects of capsaicin, heat, and heat plus ruthenium red (RR) upon capsaicin receptor-expressing Xenopus oocytes and control water-injected oocytes.

These data indicate that VR1 is directly involved in this thermal response; application of ruthenium red reduced significantly (88±2%; n=5) the response of VR1-expressing oocytes to heat, while the smaller response seen in control cells was reduced by only 21±26% (n=5) (FIG. 17). Taken together, these observations strongly support the hypothesis that VR1 is activated by noxious, but not innocuous heat.

Example 11

Chromosomal Localization And Isolation Of The Mouse VR1 Gene

The chromosomal localization of the mouse VR1 gene was determined using fluorescent in situ hybridization (FISH) according to methods well known in the art. Briefly, a bacterial artificial chromosome containing a 90–100 kb insert of mouse genomic DNA encoding portions of the mouse VR1 gene was isolated by PCR analysis and Southern hybridization using rat VR1 derived probes. This insert was labeled with digoxigenin and applied to metaphase spreads of mouse chromosomes. Fluorescently tagged anti-digoxigenin antibodies were then used to visualize the position on the chromosomes to which the VR1 gene hybridized.

The VR1 gene mapped to the B3 band of mouse chromosome 11, approximately 49% of the way from the heterochromatic-euchromatic boundary to the telomere of chromosome 11. This region of the mouse chromosome is syntenic to human chromosome 17, particularly the regions 17p11–13, 17pter, and 17qter. It is therefore probable that the human VR1 gene is located within those analogous regions on the human chromosome.

The mouse VR1 gene was sequenced according to methods well known in the art. The nucleotide (SEQ ID NO:10) and amino acid (SEQ ID NO:11) sequences of mouse VR1 are provided in the Sequence Listing below. The rat and mouse VR1 amino acid sequences are more than 95% identical.

Example 12

Identification Of Capsaicin Receptor-Related Polypeptide VRRP-1

A Genbank database search using VR1 revealed a number of human and mouse EST sequences similar VR1. Alignment of these EST sequences suggested that all of them, except one (see below) encode identical or very similar genes, suggesting that they represent fragments of the human and mouse versions of the VR1 gene. Over all regions analyzed, the predicted sequences of the encoded human and mouse proteins were highly identical to one another, but only about 50% identical to the rat VR1. Because mouse VR1 protein is more similar to the rat VR1 protein than 50%, we concluded that these EST sequences must encode human and mouse versions of a related protein, which we have termed VRRP-1. VRRP-1 is an example of the capsaicin receptor-related polypeptides encompassed by the present invention.

Portions of the VRRP-1 genes from mouse brain, rat brain, and human CCRF-CEM cells were cloned using PCR primers (GAC CAG CM GTA CCT CAC (SEQ ID NO:12) and C TCC CAT GCA GCC CAG TTT ACT TCC TCC ACC CTG MG CAC CAG CGC TCA (SEQ ID NO:13))), which were based on the consensus of human and mouse EST sequences. A full-length rat VRRP-1 cDNA was isolated from a rat brain cDNA library using the rat PCR product as a radiolabeled probe. The rat VRRP-1 cDNA (SEQ ID NO:3; amino acid sequence SEQ ID NO:4)) is approximately 49% identical to rat VR1 at the amino acid level (SEQ ID NOS:2 (rat VR1) and 4 (rat VRRP-1)) and 59% identical at the nucleotide level (SEQ ID NOS:1 (rat VR1) and 3 (rat VRRP-1)).

VRRP-1 does not appear to be activated by capsaicin or heat. Preliminary evidence suggests VRRP-1 may interact with VR1.

Example 13

Identification Of Human Capsaicin Receptor VR1

Figure 18:
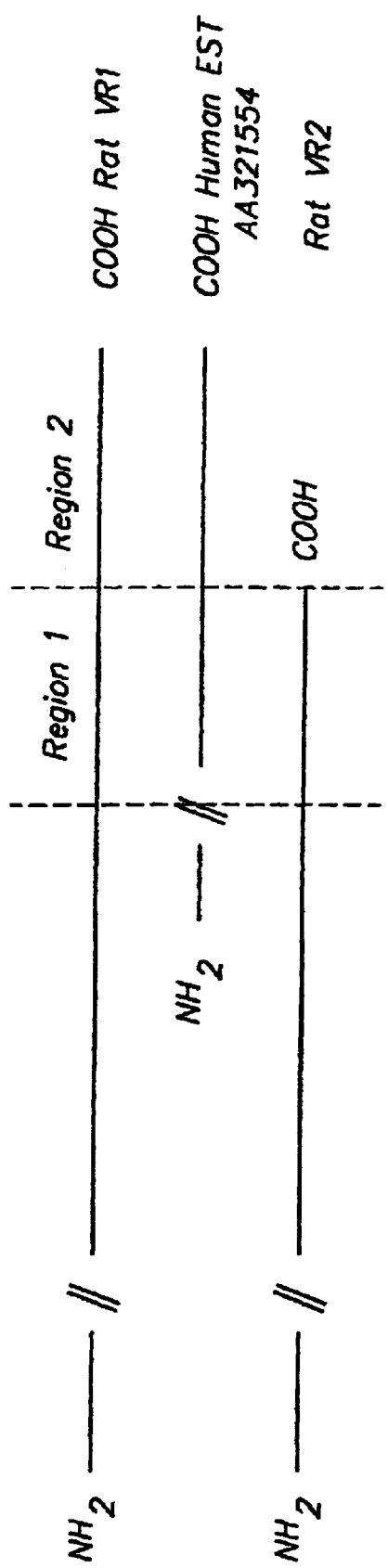
FIG. 18 is a schematic illustrating the relationship between rat VR1, rat VRRP-1, and the human EST sequence AA321554.

Comparison of VR1 with VRRP-1 and other sequences in the Genbank database suggested that VR1 and VRRP-1 are much more closely related to one another than any other cloned sequences, with one exception. A single human EST sequence (accession number M321554; SEQ ID NO:8) obtained from human CCRF-CEM lymphoid cells encodes an amino acid sequence (SEQ ID NO:9) that is at least 71% identical and at least 80% similar to the predicted extreme carboxy terminal domain of the rat VR1 (amino acid residues 774 to 838 of SEQ ID NO:2; see Region 2 of the schematic in FIG. 18). Moreover, rat VR1 (SEQ ID NO:1) and the human ES AA321554 (SEQ ID NO:8) are 75% identical at the nucleotide level. In addition, EST AA321554 contains a stop codon in the same position as the stop codon in rat VR1. In contrast, although there is homology between a portion of EST AA321554 and the carboxy terminus of rat VRRP-1 (see Region 1 in FIG. 18), the rat VRRP-1 polypeptide is shorter than the rat VR1 polypeptide and the protein from which EST AA321554 appears to be derived. Moreover, even with in Region 1, there is greater homology between rat VR1 and EST M321554 than between either rat VR1 and rat VRRP-1 or than between rat VRRP-1 and EST AA321554. Therefore, the human EST sequence AA321554 represents the human version (ortholog) of rat VR1.

PCR primers based upon the human sequence were designed to amplify this fragment from cDNA isolated from CCRF-CEM cells or from human sensory ganglion cDNA. The resulting fragment is used as a probe to screen a human genomic DNA library to obtain a full-length human VR1 cDNA sequence from CCRF-CEM cell or human sensory ganglion cDNA. Using the resulting human VR1 genomic fragment, the chromosomal localization of the VR1 gene is confirmed by FISH. The function of the polypeptide encoded by the human VR1 gene is confirmed using the functional assays described above.

Example 14

Identification Of Human Capsaicin Receptor-Related Polypeptide VRRP-1

Rat VRRP-1 sequences were used to screen the Genbank-database to identify capsaicin receptor-related polypeptides from other organisms. The screen identified several human and mouse EST sequences having homology to three separate regions of rat VRRP-1, which regions are termed Regions A, B, and C. Regions A, B, and C represents portions of the VRRP-1 sequence within which the human and mouse VRRP-1-encoding ESTs are clustered, listed from 5' to 3' respectively. Region A encompasses from about residue 580 to about residue 850; Region B encompasses from about nucleotide residue 960 to about residue 1730; and Region C encompasses from about nucleotide residue 1820 to about residue 2505 in rat the VRRP-1 nucleotide sequence. A summary of the human and mouse EST sequences corresponding to each of these regions is provided in the table below.

TABLE

Human and Mouse EST Sequences Corresponding to Rat VRRP-1

|  | Rat VRRP-1 Region A (Genbank Accession Nos.) | Rat VRRP-1 Region B (Genbank Accession Nos.) | Rat VRRP-1 Region C (Genbank Accession Nos.) |
| --- | --- | --- | --- |
| Human ESTs | H20025, AA236416, H51393, AA236417, H27879, H50364, N21167, AA461295, N26729, H21490, H49060 | AA281349, W44731, N23395, W38665, AA357145, N24224 | W92895, T12251, AA304033, N35179, AA281348 |
| Mouse ESTs | W82502, W53556 | AA139413 | AA476107, AA015295, AA274980 |

These human and mouse EST sequences can be used to determine a consensus nucleotide sequence for each of Regions A, B, and C. The consensus nucleotide sequence for human VRRP-1 for Region A (SEQ ID NO:5), Region B (SEQ ID NO:6), and Region C (SEQ ID NO:7) are provided in the Sequence Listing below. The consensus sequences can be used to design PCR probes to isolate a fragment encoding the full-length VRRP-1 using methods that are well known in the art.

Example 15

Cloning and Sequencing of a Human VRRP-1

The rat VR1 nucleotide and protein sequences were used to search the genbank databases for related entities. A number of expressed sequence tag (EST) sequences were found that exhibited homology to the rat VR1. These were from human and mouse sources. These sequences were aligned with each other and with rat VR1 and found that all but one of the human sequences appeared to encode the same protein and that this protein was highly homologous to the protein encoded by the mouse sequences. The predicted sequences of these human and mouse proteins were about

Example 16

Cloning Chicken VR1 Homologues

Degenerate oligonucleotides were designed based on the amino acid sequence of rat VR1. The oligonucleotides ODJ3885 and ODJ3887 corresponding to VR1 amino acid residues 638–644 and 676–682, respectively, were used as primers for polymerase chain reactions (PCR) with chick genomic DNA as template.

```
ODJ3885 (SEQ ID NO:28)-  5' TT(TC)AA(AG)TT(TC)AC(GATC)AT(ATC)GG(GATC)ATG

ODJ3887 (SEQ ID NO:29)   5' CAT(GATC)A(GA) (GATC)GC(GAT)AT(GATC)A(GA)CAT(AG)TT
```

Products of approximately 130 bp resulted, which were isolated and ligated into the vector pT-Adv (Clontech). The inserts in several of these plasmid clones were sequenced. The products from chick genomic DNA fell into two classes: one also corresponding to a very close homologue, and another corresponding to a somewhat more divergent homologue.

```
CVR-PCR1 (SEQ ID NO:30)
TTCAAGTTCACGATTGGGATGGGTGACCTGGATTTTCATGAACATGCCAGATTCAGATACTTTGTCATGCTTCTGCTG
CTGCTTTTTGTGATCCTCACCTACATCCTTTTGCTCAACATGCTTATAGCCCTTATA

CVR-PCR2 (SEQ ID NO:31)
TTCAAGTTCACTATTGGGATGGGAGACCTGGAGTTTACAGAGAACTACAGGTTCAAGTCTGTGTTTGTCATCCTTTTG
GTTCTCTATGTCATCCTTACGTACATCCTCCTGCTCAATATGCTTATAGCCCTAATG
```

50% identical to the rat VR1 protein but much more highly related to one another.

Using the human and mouse EST sequences, PCR primers were designed that were then used on rat brain-derived cDNA to amplify a DNA fragment encoding most of this putative protein. This fragment was radiolabeled and used as a hybridization probe to isolate a full-length cDNA from a rat brain-derived cDNA library. The cDNA (rat VRRP-1) encodes a protein of 761 aa (SEQ ID NO:3) that is 49% identical to the rat VR1 protein and 74% identical to the human VRRP1 protein (SEQ ID NO:23) predicted from the available EST sequences. The rat VRRP-1 mRNA is expressed in sensory ganglia and in other tissues such as brain, spinal cord, spleen, lung, and large intestine.

The human and mouse EST sequences were used to design PCR primers that would allow amplification of the human VRRP-1 sequence from a human-derived cDNA source. Using cDNA derived from human CCRF-CEM cells, a fragment of the human VRRP-1 cDNA was amplified and sequenced, thereby confirming its identity with a subset of the reported EST sequences. Subsequently, PCR primers directed against the 5 prime and 3 prime ends of the predicted human VRRP-1 sequence were used to amplify from CCRF-CEM-derived cDNA a DNA band of approximately 2500 bp, which is the correct size for the human cDNA, as predicted by the alignment of the human EST sequences with the rat VRRP-1. The human cDNA was then sequenced using standard methods well known in the art. The DNA sequence of human VRRP-1 (VR2) is provided as SEQ ID NO:35, with the deduced amino acid sequence provided as SEQ ID NO:36.

A 150 bp EcoRI fragment containing CVR-PCR2 was used as a hybridization probe to screen clones from a cDNA library derived from RNA isolated from chick embryonic dorsal root ganglia (DRG). Several hybridizing plasmids were identified Two of these correspond to a probable chick orthologue of rat VR1. The insert of one of these pCVR2 was sequenced in its entirety (SEQ ID NO:24). The deduced protein sequence (SEQ ID NO:25) shows an amino acid identity to rat VR1 of 67%. Nucleotide alignment of the coding regions of rat and chick VR1 cDNAs also shows 67% identity. Electrophysiological and calcium-imaging analysis of HEK293 cells transfected with pCVR2 indicate that the encoded protein responds to protons and to high doses of the vanilloid, resiniferatoxin, but not to capsaicin and to heating protocols which activate rat VR1.

Example 17

Cloning of a Human Vanilloid Receptor

A PCR reaction using ODJ3885 and ODJ3887 with human genomic DNA as template produced a 130 bp product. This band was purified and cloned into pT-Adv. The inserts of several clones were sequenced, which showed them all to encode a very close homologue or othologue of rat VR1. The nucleotide sequence (SEQ ID NO:26) is 91% identical to the corresponding region of rat VR1. The deduced protein sequence over this 45 codon segement is identical to that of rat VR1. Using this new alignment, additional PCR primers were designed to allow amplification of larger segments of VR1-homologous sequences from human cDNA sources. Primers ODJ4018, corresponding to VR1 amino acid residues 423–429, and ODJ3767, which was derived from the sequence of human EST AA321554, were used in a PCR reaction using as template cDNA from human DRG.

ODJ4018 (SEQ ID NO:32) 5' TA(TC) TT(TC) AA(TC) TT(TC) TT(TC) GT(GATC) TA 3'

ODJ3767 (SEQ ID NO:33) 5' AAA AGG GGG ACC AGG GC 3'

The resulting products were separated by gel electrophoresis transferred to nylon membranes for hybridization with a 150 bp probe derived from the previous PCR analysis. A hybridizing fragment of about 1100 bp was thus identified. This is the size expected to be produced by the position of these primers in the rat VR1 sequence.

The fragment is cloned for sequence analysis. The resulting sequence data is used to design primers for cloning a full length human cDNA corresponding to this sequence. This will be accomplished using the RACE PCR cloning method [Frohman, M. A. (1993) Methods Enzymol, 218:340–358.]. This may also be carried out using primers derived from the sequence of the small PCR fragment HVR-PCR1.

Example 18

Cloning and Sequencing of a Human Vanilloid Receptor (VR1)

In order to obtain sequences corresponding to the human orthologue of rat VR1, a segment of human genomic DNA was identified which contained sequences present in hVR-PCR1. This genomic DNA was isolated from a library of BAC plasmid clones containing large segments of human genomic DNA (Shizuya, et al 1992, Proc Nat Acad of Sci USA, 89:8794–8797) by Genomic Systems Inc., using oligonucleotide PCR primers derived from the sequence determined for hVR-PCR1. PCR reactions using oligonucleotides ODJ4079 (GGCGACCTGGAGTTCACTGAG (SEQ ID NO:37)) and ODJ4080 (GAGCAGGAGGATGTAGGT-GAG (SEQ ID NO:38)) as primers, and human genomic DNA as template resulted in the expected 92 bp product. A product of the same size was also obtained using as template cDNA from CCRF-CEM, a human cell line from which the EST sequence #24046 was obtained. This EST sequence appeared to correspond to a close homologue or orthologue of rat VR1. Using these primers to screen a human BAC library by PCR, Genomes Systems provided two BAC plasmid clones, 20614 and 20615.

These two clones were further analyzed by restriction digestion and Southern blotting, using the VR1 hybridization probes described above. Inspection of the pattern of restriction fragments using several different restriction endonucleases indicated that these two clones were probably identical. In order to confirm that these plasmids, in fact, contained VR1-related sequences, Southern blots from these digests were hybridized incubated with different VR1 hybridization probes. The blots were first hybridized to a $^{32}$p labeled 150 bp EcoRI fragment from hVR-PCR1. A single fragment from each digest hybridized with this probe.

In the case of a PstI digest the hybridizing fragment was approximately 250 bp. The products of PstI digestion of this BAC plasmid were ligated into PstI-digested pBluescriptSK+. The resulting ligation products were used to transform cells of the E. coli strain DH5α. Resulting transformants were screened by hybridization with the same hVR-PCR1 probe. The insert of one of these clones, hVR1-P1 was sequenced. The results showed that it was highly similar to rat VR1 and corresponded to hVR-PCR1. Alignment of the exon portion of this insert with rVR1 cDNA is shown below.

```
hVR1-P1:     1 ctgcagcttccagatgttcttgctctcctgtgcgatcttgttgacagtctcacccatgag   (SEQ ID NO:39)
               |||||||||||||||||||||||||||| ||||| |||||||||| |||||||||||||||
rVR1:     2180 ctgcagcttccagatgttcttgctctcttgtgcaatcttgttgacggtctcacccatgag   (SEQ ID NO:40)

hVR1-P1:    61 ggcgatgagcatgttgagcaggaggatgtaggtgagaattacataggccagcagcaggat
               || |||||||||||||||||| |||||||||||||| ||||||||||||||| | ||||||
rVR1:     2120 agcaatgagcatgttgagcagaaggatgtaggtgagaatcacataggccagtaacaggat hVR1-P1:   121 gatgaagacagccttgaagtcatagttctcagtgaactccaggtcgcccatgccgatggt
               |||||||||||||||||||||| |||| ||||||||||||||||||||||||||||||||
rVR1:     2060 gatgaagacagccttgaagtcgtagttctcagtgaactccaggtcgcccatgccgatggt hVR1-P1:   181 gaacttgaacagctccaggcaggtggagtacaggctgttgtaggag
               ||||||||||||||||||| || ||||| |||||||||||||| |||
rVR1:     2000 gaacttgaacagctccagacatgtggaatacaggctgttgtaagag
```

In order to further localize VR1-related sequences on this BAC plasmid insert, Southern blots were performed using a 1008 bp NheI fragment from the rVR1 cDNA as a hybridization probe. This fragment includes almost the entire 5' portion of the rVR1 coding sequence. In this case each digest produced one or more fragments that hybridized strongly with this probe. In particular, HindIII digestion produced two hybridizing fragments of approximately 12 kbp and 18 kbp. The 18 kbp also hybridized with the hVR-PCR1 probe, indicating that the 12 kbp fragment probably contained the 5' end of the hVR1-coding region. These fragments were subcloned into pBluescriptSK+ for further analysis. Three resulting clones were obtained. The clones hVR1-H1 and hVR1-H2 contained the 12 kbp fragment inserted in opposite orientations. The clone hVR1-H3, contained a 18 kbp insert. Sequence reactions carried out using vector-derived primers resulted in no VR1-related sequences, indicating that these end segments corresponded to either introns or 5' or 3' flanking sequences. A sequencing reaction of hVR1-H3 using the primer CCRF2, which was derived from the EST24046 sequence was also carried out. The resulting sequence data showed that hVR1-H3 contained VR1-related sequence that appeared to be identical to that present in EST24046. An alignment of these two sequences is shown below.

All publications and patents mentioned in the above specification are herein incorporated by reference. Various modifications and variations of the described method and system of the invention will be apparent to those skilled in the art without departing from the scope and spirit of the

```
HVR1-H3:     1 aagacctcagcgtcctctggcttcagagaccctgnaaaactgtcgcagataaacttcctc  (SEQ ID NO:41)
               |||||||||||||||||||||||| |||||||||| |||||||||||||||||||||||
EST24046:  168 aagacctcagcgtcctctggctttagagaccctg-aaaactgtcgcagataaacttcctc  (SEQ ID NO:42)

HVR1-H3:    61 gggctgagcanactgcctatctcgagcacttgcctctcttaaaagggggaccagggcaaa
               |||||||||| ||||||||||| |||| ||||||||||||||||||||||||||||||||
EST24046:  109 gggctgagcagactgcctatntcgagnacttgcctctcttaaaagggggaccagggcaaa HVR1-R3:   121 gttcttccagtgtctgcctgaaact
               |||||||||||||||||||||||||
EST24046:   49 gttcttccagtgtctgcctgaaact
```

In order to identify sequences at the 5' end of the human VR1 coding region present in this genomic clone, a 1500 bp BamHI fragment was subcloned from hVR1-H1 into pBluescriptSK+. The insert in one of the resulting clones, hVR1-B2 was sequenced using vector-based primers (T3 and T7). Sequence from one end of this clone revealed VR1-related sequence as shown by the nucleotide alignment or by alignment of the deduced protein sequence of this clone with that of rVR1. Inspection of these alignments shown below indicated that the translational start of the hVR1 coding region is probably at position 14 of this sequence.

invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

Before the present nucleotide and polypeptide sequences are described, it is to be understood that this invention is not limited to the particular methodology, protocols, cell lines, vectors and reagents described as such may, of course, vary.

```
HVR1-B2:    55 cccactccaaaaggacacctgcccagacccctggatggagaccctaactccaggccacc  (SEQ ID NO:44)
               ||||| |||| || || ||||||| ||||| | || ||||||||||||| || ||||||
rVR1:      122 cccacccaagagaactcctgcctggaccctccagacagagaccctaactgcaagccacc  (SEQ ID NO:45)

HVR1-B2:   115 tccagccaagccccagctctccacggccaagagccgcaccggctctttgggaagggtga
               ||||| |||||||||  ||| |||  ||| ||| || |||||||| |||||||||||||
rVR1:      182 tccagtcaagccccacatcttcactaccaggagtcgtaccggcttttgggaagggtga HVR1-B2:   175 ctcggaggaggctttcccggtggattgccctcacgaggaaggtgagctggactcctgccc
               |||||||||||| |  || |||| |||||| | |||||||| | ||||| |||||||||
rVR1:      242 ctcggaggaggcctctcccctggactgcccttatgaggaaggcgggctggcttcctgccc HVR1-B2:   235 gaccatcacagtcagccctgttatcaccatccagaggcc                         273
               | |||||| |||||| ||||| | || |||||||||||
rVR1:      302 tatcatcactgtcagctctgttctaactatccagaggcc                         340

HVR1-B2:    14 MKKWSSTDLGAAADPLQKDTCPDPLDGDPNSRPPPAKPQLSTAKSRTRLFGKGDSEEAFP  (SEQ ID NO:45)
               M++ +S D   +  P Q+++C DP D DPN +PPP KP + T +SRTRLFGKGDSEEA P
rVR1:        1 MEQRASLDSEESESPPQENSCLDPPDRDPNCKPPPVKPHIFTTRSRTRLFGKGDSEEASP  (SEQ ID NO:46)

HVR1-B2:   194 VDCPHEEGELDSCPTITVSPVITIQRPRXRP                                 286
               +DCP+EEG L SCP ITVS V+TIQRP    P
rVR1:       61 LDCPYEEGGLASCPIITVSSVLTIQRPGDGP                                  91
```

Using this sequence information, two primers were designed to allow production of a human VR1 cDNA from using RT-PCR from polyA+ RNA isolated from the CCRF-CEM cell line. The two primers ODJ4157 (AGAAATGGAGCAGCACAGACTTGG (SEQ ID NO:47)) and ODJ4162 (TCACTTCTCCCCGGAAGC-GGCAG (SEQ ID NO:48)) were used as primers in a PCR reaction with CCRF-CEM cDNA as template. A product of about 2500 bp resulted from this reaction. Southern blot analysis of this product using a hVR-PCR1 hybridization probe, indicated that this product was, in fact, VR1-related. The product was purified by preparative agarose gel electrophoresis and subcloned into the vector pT-Adv (Clontech). Several clones were isolated and four of these were subjected to DNA sequence analysis. The resulting DNA sequence of human VR1 is provided as SEQ ID NO:33, with the deduced amino acid sequence provided as SEQ ID NO:34.

It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a host cell" includes a plurality of such host cells and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

What is claimed is:

1. A method of screening for an agent that modulates capsaicin receptor function, the method comprising:
   a) combining a candidate agent with a eukaryotic cell comprising a recombinant nucleic acid comprising a nucleotide sequence that encodes a biologically active capsaicin receptor polypeptide, which nucleotide sequence is operably linked to a promoter, wherein said capsaicin receptor is encoded by a polynucleotide that hybridizes under stringent hybridization conditions to the complement of a polynucleotide having the sequence set forth in SEQ ID) NO: 1, and wherein the capsaicin receptor polypeptide is expressed on the cell surface; and
   b) determining the effect of said agent on capsaicin receptor function.

2. The method of claim 1, wherein said determining is by measuring capsaicin receptor-mediated increase in intracellular concentration of a cation.

3. The method of claim 2, wherein the cation is selected from the group consisting of calcium, magnesium, potassium, cesium, and sodium.

4. The method of claim 2, wherein the cation is calcium.

5. The method of claim 1, wherein said determining is by measuring a capsaicin receptor-mediated electrophysiological response.

6. The method of claim 5, wherein the electrophysiological response is an inward cation-specific current.

7. The method of claim 5, wherein the response is measured using a fluorescent voltage-sensitive dye.

8. The method of claim 1, wherein said determining is by measuring blocking the activity of a capsaicin receptor antagonist.

9. The method of claim 8, wherein the capsaicin receptor antagonist is selected from the group consisting of capsazepine and ruthenium red.

10. The method of claim 1, wherein said determining is by measuring blocking the activity of a capsaicin receptor agonist.

11. The method of claim 10, wherein the capsaicin receptor agonist is selected from the group consisting of resiniferatoxin and capsaicin.

12. The method of claim 1, wherein said determining is by measuring capsaicin receptor-mediated apoptosis.

13. The method of claim 1, wherein said cell further comprises a reporter gene operably linked to a calcium inducible promoter, and wherein said determining is by measuring calcium-induced expression of the reporter gene.

14. The method of claim 1, wherein the cell is selected the group consisting of an amphibian oocyte, a mammalian cell line, and a cultured neuron.

15. The method of claim 1, wherein the capsaicia receptor is a mammalian capsaicin receptor.

* * * * *

UNITED STATES PATENT AND TRADEMARK OFFICE
CERTIFICATE OF CORRECTION

PATENT NO.    : 6,790,629 B2
DATED         : September 14, 2004
INVENTOR(S)   : Julius, David J. et al.

It is certified that error appears in the above-identified patent and that said Letters Patent is hereby corrected as shown below:

Column 1,
Line 19, please insert the following text:
-- GOVERNMENT SUPPORT
   The United States Government may have certain rights in this application pursuant to National Institutes of Health Grant Nos. DE08973 and GM44298. --

Signed and Sealed this

Twelfth Day of April, 2005

JON W. DUDAS
*Director of the United States Patent and Trademark Office*